United States Patent
Person et al.

(10) Patent No.: US 11,046,738 B2
(45) Date of Patent: Jun. 29, 2021

(54) WNT/SFRP COMPLEXES, WNT-CONTAINING COMPOSITIONS, WNT-EXPRESSING CELLS, AND METHODS OF MAKING, PURIFYING, AND USING SAME

(71) Applicant: BIO-TECHNE CORPORATION, Minneapolis, MN (US)

(72) Inventors: Anthony Person, Blaine, MN (US); Liwen Xiong, Woodbury, MN (US); Ming Bi, Woodbury, MN (US); Camrin Tracy, Arden Hills, MN (US)

(73) Assignee: BIO-TECHNE CORPORATION, Minneapolis, MN (US)

( * ) Notice: Subject to any disclaimer, the term of this patent is extended or adjusted under 35 U.S.C. 154(b) by 67 days.

(21) Appl. No.: 16/155,439

(22) Filed: Oct. 9, 2018

(65) Prior Publication Data

US 2019/0106468 A1    Apr. 11, 2019

Related U.S. Application Data

(60) Provisional application No. 62/569,748, filed on Oct. 9, 2017.

(51) Int. Cl.
| | | |
|---|---|---|
| C07K 14/47 | (2006.01) |
| C07K 14/71 | (2006.01) |
| C12Q 1/6897 | (2018.01) |
| C07K 14/475 | (2006.01) |
| C07K 19/00 | (2006.01) |
| C12N 5/071 | (2010.01) |

(52) U.S. Cl.
CPC ............ *C07K 14/47* (2013.01); *C07K 14/475* (2013.01); *C07K 14/71* (2013.01); *C07K 19/00* (2013.01); *C12Q 1/6897* (2013.01); *C12N 5/0686* (2013.01)

(58) Field of Classification Search
None
See application file for complete search history.

(56) References Cited

U.S. PATENT DOCUMENTS

| | | | | |
|---|---|---|---|---|
| 2007/0072239 A1* | 3/2007 | Bhat | ................ | C07K 14/71 435/7.1 |
| 2010/0068708 A1* | 3/2010 | Hood | ................ | G01N 33/5023 435/5 |
| 2012/0202749 A1* | 8/2012 | Rubin | ................ | C07K 14/47 514/19.2 |
| 2014/0171356 A1* | 6/2014 | Habib | ................ | A61K 38/16 514/1.1 |
| 2019/0100724 A1* | 4/2019 | Sato | ................ | C12N 5/00 |

FOREIGN PATENT DOCUMENTS

| | | | | |
|---|---|---|---|---|
| WO | WO 2014/194267 A2 | 12/2014 | | |
| WO | WO-2014194267 A2 * | 12/2014 | ......... | C07K 14/4702 |
| WO | WO 2018/027042 A1 | 2/2018 | | |

OTHER PUBLICATIONS

Agostino et al., J Biol Chem. Jul. 7, 2017;292(27):11218-11229 (Year: 2017).*
Alexandre et al., Patterning and growth control by membrane-tethered Wingless. *Nature* 505, 180-185 (2014).
Bafico et al., Interaction of frizzled related protein (FRP) with Wnt ligands and the frizzled receptor suggests alternative mechanisms for FRP inhibition of Wnt signaling. *J Biol Chem* 274, 16180-16187 (1999).
Burrus et al., Biochemical analysis of murine Wnt proteins reveals both shared and distinct properties. *Exp Cell Res* 220, 363-373 (1995).
Cruciat et al., Secreted and transmembrane wnt inhibitors and activators. *Cold Spring Harb Perspect Biol* 5, a015081 (2013).
Dennis et al., A secreted frizzled related protein, FrzA, selectively associates with Wnt-1 protein and regulates wnt-1 signaling. *J Cell Sci* 112 ( Pt 21), 3815-3820 (1999).
Farin et al., Visualization of a short-range Wnt gradient in the intestinal stem-cell niche. *Nature* 530, 340-343 (Feb. 18, 2016).
Green et al., Use of a molecular genetic platform technology to produce human Wnt proteins reveals distinct local and distal signaling abilities. *PLoS One* 8, e58395 (2013).
Holly et al., Sfrp1a and Sfrp5 function as positive regulators of Wnt and BMP signaling during early retinal development. *Dev Biol* 388, 192-204 (2014).
Janda et al., Structural basis of Wnt recognition by Frizzled. *Science* 337, 59-64 (2012).
Klein et al., A molecular mechanism for the effect of lithium on development. *Proc Natl Acad Sci U S A* 93, 8455-8459 (1996).
Korinek et al., Constitutive transcriptional activation by a beta-catenin-Tcf complex in APC-/- colon carcinoma. *Science* 275, 1784-1787 (1997).
Lam et al., Directed differentiation of pluripotent stem cells to kidney cells. *Semin Nephrol* 34, 445-461 (2014).
Leyns et al., Frzb-1 is a secreted antagonist of Wnt signaling expressed in the Spemann organizer. *Cell* 88, 747-756 (1997).
Lustig et al., Negative feedback loop of Wnt signaling through upregulation of conductin/axin2 in colorectal and liver tumors. *Mol Cell Biol* 22, 1184-1193 (2002).
Macdonald et al., Frizzled and LRP5/6 receptors for Wnt/beta-catenin signaling. *Cold Spring Harb Perspect Biol* 4, a007880 (2012).

(Continued)

*Primary Examiner* — Daniel C Gamett
(74) *Attorney, Agent, or Firm* — Mueting Raasch Group

(57) ABSTRACT

This disclosure describes isolated protein complexes including a Wnt and a sFRP; compositions including a Wnt; a cell overexpressing a Wnt and a sFRP; compositions including a cell overexpressing a Wnt and a cell overexpressing a sFRP; methods of making the protein complexes, compositions, and cells; and methods of using the isolated protein complexes, compositions, and cells. This disclosure further describes methods of forming a complex including a Wnt and a sFRP and methods for isolating a Wnt. Also described herein are methods that may be used to purify a Wnt without the use of a detergent.

15 Claims, 14 Drawing Sheets

Specification includes a Sequence Listing.

(56) References Cited

OTHER PUBLICATIONS

McMahon et al., Ectopic expression of the proto-oncogene int-1 in Xenopus embryos leads to duplication of the embryonic axis. *Cell* 58, 1075-1084 (1989).
Mii et al., Secreted Frizzled-related proteins enhance the diffusion of Wnt ligands and expand their signalling range. *Development* 136, 4083-4088 (2009).
Molenaar et al., XTcf-3 transcription factor mediates beta-catenin-induced axis formation in Xenopus embryos. *Cell* 86, 391-399 (1996).
Moon et al., Structurally related receptors and antagonists compete for secreted Wnt ligands. *Cell* 88, 725-728 (1997).
Murashov et al., Directed differentiation of embryonic stem cells into dorsal interneurons. *FASEB J* 19, 252-254 (2005).
Paige et al., Endogenous Wnt/beta-catenin signaling is required for cardiac differentiation in human embryonic stem cells. *PLoS One* 5, e11134 (2010).
R&D Systems, Catalog No. 9765-WN, Recombinant Mouse Wnt-1 / sFRP-1 Complex, Product Information Sheet, dated Apr. 11, 2018 (initially on sale Mar. 28, 2018).
Reya et al., A role for Wnt signalling in self-renewal of haematopoietic stem cells. *Nature* 423, 409-414 (2003).
Shimizu et al., Transformation by Wnt family proteins correlates with regulation of beta-catenin. *Cell Growth Differ* 8, 1349-1358 (1997).
Spence et al., Directed differentiation of human pluripotent stem cells into intestinal tissue in vitro. *Nature* 470, 105-109 (2011).
Steinhauer et al., Lipid-modified morphogens: functions of fats. *Curr Opin Genet Dev* 19, 308-314 (2009).
Tamai et al., A mechanism for Wnt coreceptor activation. *Mol Cell* 13, 149-156 (2004).
Tuysuz et al., Lipid-mediated Wnt protein stabilization enables serum-free culture of human organ stem cells. *Nat Commun* 8, 14578 (Mar. 6, 2017).
Van Noort et al., Wnt signaling controls the phosphorylation status of beta-catenin. *J Biol Chem* 277, 17901-17905 (2002).
Van Ooyen et al., The nucleotide sequence of the human int-1 mammary oncogene; evolutionary conservation of coding and non-coding sequences. *EMBO J* 4, 2905-2909 (1985).
Wang et al., Self-renewing diploid Axin2(+) cells fuel homeostatic renewal of the liver. *Nature* 524, 180-185 (2015).
Wang et al., Frzb, a secreted protein expressed in the Spemann organizer, binds and inhibits Wnt-8. *Cell* 88, 757-766 (1997).
Wang et al., Frzb-1, an antagonist of Wnt-1 and Wnt-8, does not block signaling by Wnts -3A, -5A, or -11. *Biochem Biophys Res Commun* 236, 502-504 (1997).
Willert et al., Wnt proteins are lipid-modified and can act as stem cell growth factors. *Nature* 423, 448-452 (2003).
Willert et al., Wnt proteins. *Cold Spring Harb Perspect Biol* 4, a007864 (2012).
Wong et al., Differential transformation of mammary epithelial cells by Wnt genes. *Mol Cell Biol* 14, 6278-6286 (1994).
PCT Application No. PCT/US2018/055001, filed Oct. 9, 2018; International Search Report dated Apr. Jan. 4, 2019; 4 pages.
PCT Application No. PCT/US2018/055001, filed Oct. 9, 2018; Written Opinion dated Jan. 4, 2019; 6 pages.
PCT Application No. PCT/US2018/055001, filed Oct. 9, 2018; International Preliminary Report on Patentability] dated Apr. 14, 2020; 7 pages.

\* cited by examiner

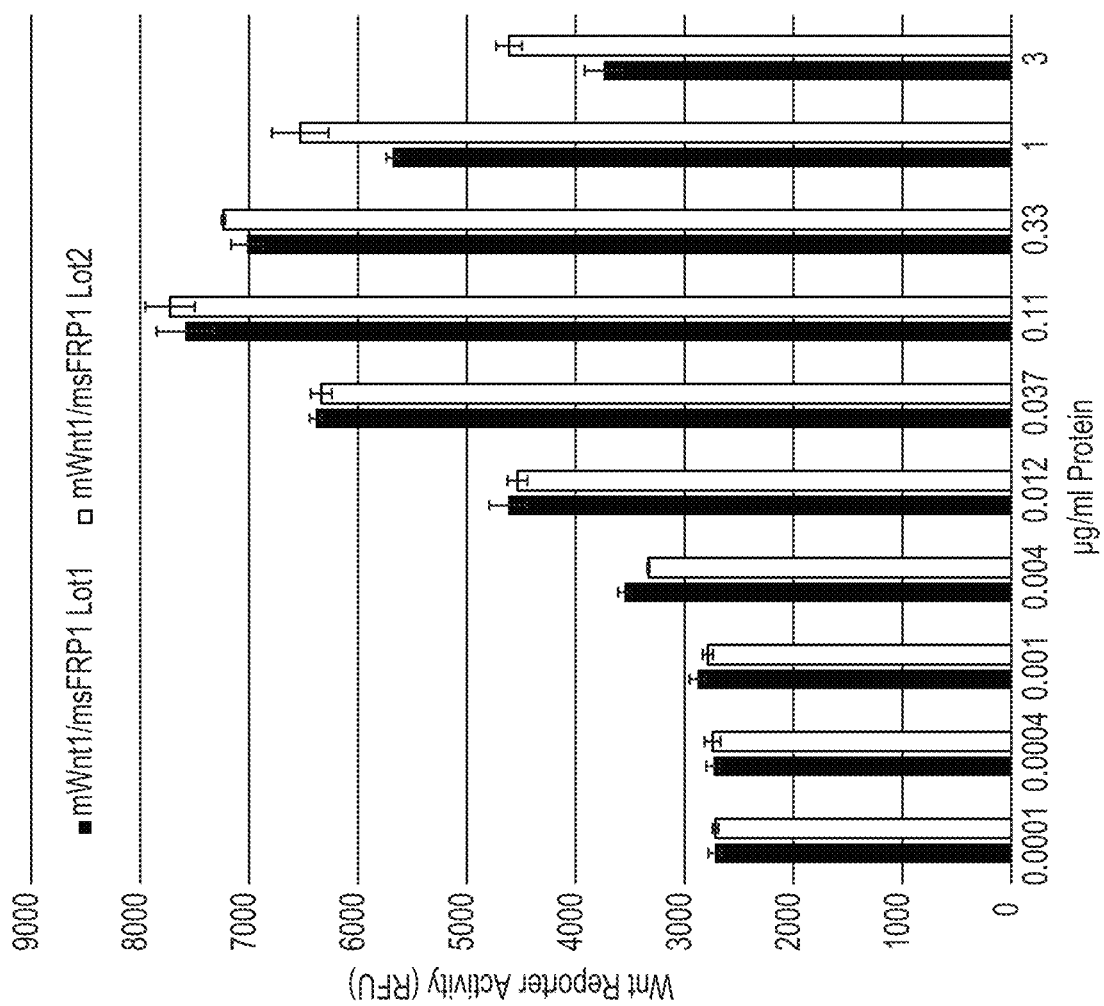

WNT/SFRP COMPLEXES, WNT-CONTAINING COMPOSITIONS, WNT-EXPRESSING CELLS, AND METHODS OF MAKING, PURIFYING, AND USING SAME

CONTINUING APPLICATION DATA

This application claims the benefit of U.S. Provisional Application Ser. No. 62/569,748, filed Oct. 9, 2017, which is incorporated by reference herein.

SEQUENCE LISTING

This application contains a Sequence Listing electronically submitted to the United States Patent and Trademark Office via EFS-Web as an ASCII text file entitled "541-00060101_ST25.txt" having a size of 84 kilobytes and created on Oct. 9, 2018. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY OF THE INVENTION

This disclosure describes an isolated protein complex that includes a Wingless/Integrated-1 protein (Wnt) and a secreted Frizzled-related protein (sFRP); a composition that includes a Wnt, wherein the composition is substantially free of a detergent; a cell overexpressing a Wnt and a sFRP; compositions including a cell overexpressing a Wnt and a cell overexpressing a sFRP; methods of making the protein complexes, compositions, and cells; and methods of using the protein complexes, compositions, and cells. In some embodiments, the Wnt preferably includes an active Wnt. In some embodiments, the compositions may be used as a media additive and may provide advantages versus compositions that include detergent.

In one aspect, this disclosure describes an isolated protein complex including a Wnt and a sFRP.

In another aspect, this disclosure describes a composition including a Wnt, wherein the composition is substantially free of a detergent.

In a further aspect, this disclosure describes a cell overexpressing a Wnt and a sFRP.

In an additional aspect, this disclosure describes a composition including a cell overexpressing a Wnt and a cell overexpressing a sFRP.

In yet another aspect, this disclosure describes a method including forming a complex including a Wnt and a sFRP and isolating the Wnt.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

BRIEF DESCRIPTION OF THE FIGURES

FIG. 1(A-B) shows co-expression of mouse sFRP1 (msFRP1) and mouse Wnt1 (mWnt1) in CHO cells results in higher levels of active mWnt1 protein in the supernatant (also referred to herein as conditioned media).

FIG. 4(A-F) shows Wnt-1 co-eluted with sFRP1 on a cation exchanger SP Sepharose column (FIG. 4(A-C)) and separation of sFRP1/Wnt-1 complex from free sFRP1 on a gel filtration column (FIG. 4(D-E)).

FIG. 6(A-D) shows a purified recombinant mWnt1/msFRP1 protein complex activates the Wnt signaling pathway in HEK293 Wnt reporter cells expressing both hFz4 and hLRP5. FIG. 6C. Recombinant mWnt1/msFRP1 protein complex purification is reproducible with multiple lots showing similar biological activity. Two different mWnt1/msFRP1 complexes were purified and compared against each other in the HEK293 hFz4/hLRP5 Wnt reporter assay and shown to both show similar activity. The maximal enhancement of Wnt reporter activity was detected at 110 ng/mL of the complexes; the activity of these mWnt1/msFRP1 complexes created a bell shaped curve with doses less than 110 ng/mL or greater than 110 ng/mL showing lower activity.

FIG. 7(A-C) shows sFRPs enhance exemplary Wnt (Wnt1, Wnt2b, and Wnt6) activity in a cell non-autonomous fashion.

DETAILED DESCRIPTION OF ILLUSTRATIVE EMBODIMENTS

Figure 1A:
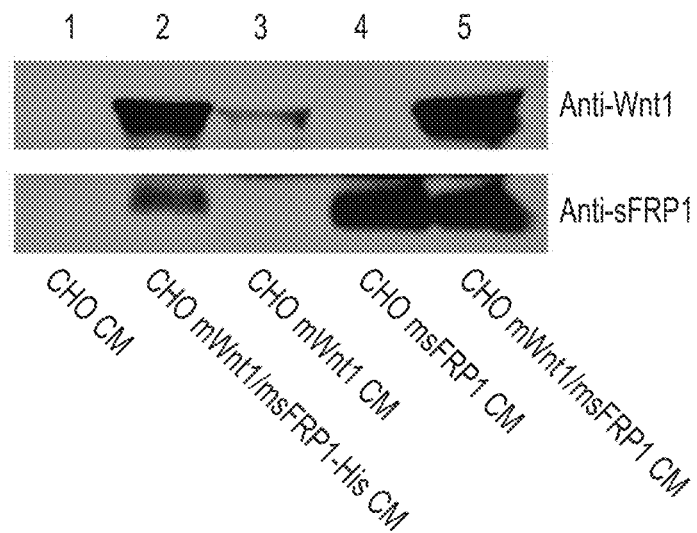
FIG. 1A. Western blots of equal amounts of conditioned media (CM) shows enhanced levels of mWnt1 in CHO cells expressing mWnt1/msFRP1-His (lane 2) and mWnt1/msFRP1 (lane 5) compared to mWnt1 levels in CHO control cell CM (lane 1), CHO mWnt1 CM (lane 3), and CHO msFRP1 (lane 4). msFRP1 Western blots show enhanced msFRP1 expression in CHO mWnt1/msFRP1-His CM (lane 2), CHO msFRP1 CM (lane 4), and CHO mWnt1/msFRP1 CM (lane 5) compared to CHO CM (lane 1) and CHO mWnt1 CM (lane 3).

This disclosure describes an isolated protein complex that includes a Wingless/Integrated-1 protein (Wnt) and a secreted Frizzled-related protein (sFRP); a composition that includes a Wnt, wherein the composition is substantially free of a detergent; a cell overexpressing a Wnt and a sFRP; compositions including a cell overexpressing a Wnt and a cell overexpressing a sFRP; methods of making the protein complexes, compositions, and cells; and methods of using the protein complexes, compositions, and cells. This disclosure further describes methods of forming a complex including a Wnt and a sFRP and isolating the Wnt. Also described herein are methods that may be used to purify a Wnt including, for example, a tethered Wnt, that could not be purified using Wnt purification protocols available at the time of the invention. This disclosure further describes methods that may be used to purify a Wnt, including, for example, a secreted Wnt, without the use of a detergent.

Wnt proteins are glycosylated and palmitoylated proteins that have proven extremely difficult to purify in an active state (Willert et al. Cold Spring Harbor Perspectives In Biology, 4:a007864 (2012)). A Wnt may include at least one of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.

Wnt family members are involved in regulating embryogenesis and control diverse processes later in life, including cell proliferation, survival, migration, polarity, specification of cell fate, and self-renewal in stem cells. Perturbation of the levels of Wnts, or altered activity of downstream effectors of Wnts may result in developmental defects and may contribute to disease etiology.

Due to the lipid modification of Wnt proteins, these growth factors may associate with the outer membrane of a Wnt-producing cell, resulting in limited secretion and signaling away from the Wnt-production source. In 2003, a procedure to purify palmitoylated Wnt proteins using (3-((3-cholamidopropyl) dimethylammonio)-1-propanesulfonate) (CHAPS) detergent was published; for this procedure, maintaining Wnts in a hydrophobic environment proved essential for retaining Wnt activity (Willert et al. Nature 423:448-452 (2003); Reya et al. Nature 423:409-414 (2003)). However, a Wnt3a protein purified with CHAPS rapidly loses activity in cell culture media due to its hydrophobic nature, and the presence of the detergent may interfere with normal cell function including, for example, stem cell self-renewal, or may prove toxic in cell culture (Tuysuz et al. Nature Communications 8:14578 (2017)).

Some Wnts can be detected in an active state in conditioned media (also referred to herein as the supernatant) of Chinese Hamster Ovary (CHO) cells overexpressing Wnts including, for example, Wnt3a, Wnt5a, Wnt5b, Wnt8a, and Wnt10a. These "secreted Wnts" are usually amenable to purification using the aforementioned CHAPS purification protocol. Other Wnts, or "tethered Wnts," including, for example, Wnt1, Wnt2b, Wnt6, Wnt7a, seem to be primarily associated with the cell membrane of cells producing these Wnts. Active Wnt protein is not detected in the conditioned media of cells making these tethered Wnts. The conditioned media from cells overexpressing tethered Wnts does not activate Wnt signaling in a paracrine manner, and only when cells making tethered Wnts are co-cultured with Wnt-responsive cells can Wnt activity be realized. Efforts to purify membrane associated proteins have proved extremely difficult, resulting in either purification of inactive proteins or low production yields that make the product economically unviable.

Secreted Frizzled-related proteins (sFRPs) are a family of secreted Wnt binding proteins that were originally described as antagonists of Wnt signaling. There are 5 sFRPs in the human and mouse genomes. sFRP1-5 all show structural similarity to the Wnt binding cysteine rich domain (CRD) of Frizzled 7-pass transmembrane receptors. Unlike 7-pass transmembrane Frizzled receptors, sFRPs are secreted proteins that contain a netrin-like domain downstream of the CRD and this netrin-like domain is not present in Frizzled receptors.

Although sFRPs were originally described as secreted proteins that bind to and inhibit Wnt activity, subsequent studies demonstrated that sFRPs may also enhance Wnt activity including, for example, when expressed at biologically relevant levels (Mii and Taira, Development 136:4083-4088 (2009); Holly et al., Developmental Biology 388:192-204 (2014).

Described herein are experimental results showing that a sFRP expressed in a Wnt-producing cell can bind to and liberate a tethered Wnt from the cell surface. Overexpression of sFRP1 or sFRP5 in Wnt1-expressing cells results in detection of active Wnt1/sFRP complexes in the conditioned media. This Wnt1/sFRP1 complex can be subsequently purified in an aqueous purification procedure that does not require the use of detergents, like CHAPS.

This disclosure also provides experimental results demonstrating that sFRP-expressing cells, or sFRP recombinant proteins, can liberate an active Wnt1/sFRP complex from the membrane of Wnt1 expressing cells in both a cell autonomous and non-cell autonomous fashion. For example, the data summarized in Table 1 suggest mouse sFRP1 (msFRP1) may bind to and liberate mouse Wnt 1 (mWnt1) from the cell membrane. Only when the secreted proteins sFRP1 or sFRP5 have contact with mWnt1 on the surface of a mWnt1 expressing cell can mWnt1 activity be detected in conditioned media. Thus, sFRPs binding to Wnts at the cell surface may allow a Wnt protein to act as a "secreted" morphogen.

Experimental results provided herein also show that sFRPs can also liberate other Wnts (including, for example, Wnt2b and Wnt6) from the outer plasma membrane of Wnt-expressing cells, resulting in Wnt2b/sFRP and Wnt6/sFRP complexes in the conditioned media of cells expressing Wnt2b or Wnt6. These data demonstrate that a sFRP can act as a Wnt binding partner. However, a biphasic response of sFRPs in the context of Wnt signaling was observed in, for example, FIG. 3, FIG. 6C.

Without wishing to be bound by theory, it is believed that a sFRP may bind to the palmitoylated moiety on a Wnt, shielding this lipid modification from the aqueous environment and, therefore, allowing tethered Wnts to be purified in an active Wnt/sFRP complex. Again, without wishing to be bound by theory, it is believed that sFRPs bind to and enhance Wnt signaling up to an amount of sFRP that saturates Wnt binding (see FIG. 3, FIG. 6C). However, once all of the available Wnt protein is complexed with a sFRP, sFRP proteins may inhibit Wnt signaling by interacting with other non-Wnt components of the Wnt pathway including, for example, Frizzled receptors (Bafico et al. The Journal of Biological Chemistry 274, 16180-16187 (1999)). For example, excess sFRP may inhibit Wnt proteins from activating Frizzled receptors.

Wnt

A Wnt may include any Wnt protein or combination of Wnt proteins. A Wnt protein may include at least one of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16. In some embodiments, the Wnt includes a secreted Wnt and/or a tethered Wnt. In some embodiments, a secreted Wnt may include at least one of Wnt3a, Wnt5a, Wnt5b, Wnt8a, and Wnt10a.

In some embodiments, the Wnt includes a eukaryotic Wnt. The Wnt may be a Wnt from any suitable eukaryote including, for example, a mammal, an amphibian (e.g., Xenopus), a bird (e.g., a chicken), or a fish (e.g., a zebrafish). In some embodiments, the Wnt preferably includes a mammalian Wnt. A mammalian Wnt may include, for example, a human Wnt, a mouse Wnt, a rat Wnt, an equine Wnt, a canine Wnt, a caprine Wnt, a bovine Wnt, etc.

In some embodiments, the Wnt includes a tagged Wnt. The Wnt may be tagged with any suitable protein tag including, for example, a histidine (His) tag, a FLAG tag, a hemagglutinin (HA) tag, an Fc tag, a glutathione S-transferase (GST) tag, a fluorescent tag (including, for example, a GFP tag, a YFP tag, a BFP tag), etc. In some embodiments, the tag may be C-terminal; in some embodiments, the tag may be N-terminal.

In some embodiments, the Wnt includes an active Wnt. As used herein, an "active Wnt" is a Wnt that activates canonical β-catenin signaling.

sFRP

A sFRP may include any sFRP protein or combination of sFRP proteins. A sFRP may include, for example, at least one of sFRP1, sFRP2, sFRP3, sFRP4, and sFRP5.

In some embodiments, the sFRP includes a eukaryotic sFRP. The sFRP may be a sFRP from any suitable eukaryote including, for example, a mammal, an amphibian (e.g., Xenopus), a bird (e.g., a chicken), or a fish (e.g., a zebrafish). In some embodiments, the sFRP preferably includes a mammalian sFRP. A mammalian sFRP may include, for example, a human sFRP, a mouse sFRP, a rat sFRP, an equine sFRP, a canine sFRP, a caprine sFRP, a bovine sFRP, etc.

In some embodiments, the sFRP includes a tagged sFRP. The sFRP may be tagged with any suitable protein tag including, for example, a histidine (His) tag, a FLAG tag, a hemagglutinin (HA) tag, an Fc tag, a glutathione S-transferase (GST) tag, a fluorescent tag (including, for example, a GFP tag, a YFP tag, a BFP tag), etc. In some embodiments, the tag may be C-terminal; in some embodiments, the tag may be N-terminal.

Isolated Protein Complexes and Compositions

In some aspects, this disclosure describes an isolated protein complex including a Wnt and a sFRP. In some embodiments, an "isolated protein complex" means a protein complex present in a composition or environment that is different from that found in nature, that is, from that found in a native or original cellular or body environment. An "isolated protein complex" may be separated from at least 50%, at least 75%, at least 90%, or at least 95% of other naturally co-existing cellular or tissue components. An "isolated protein complex" may include a naturally existing protein complex in an artificial preparation and/or in a non-native host cell. In some embodiments, an "isolated Wnt/sFRP protein complex" may include a Wnt/sFRP complex isolated from a cell engineered to express unnaturally high levels of recombinant Wnt and sFRP. In some embodiments, the cell may include a non-native host cell and/or the cell may include non-native DNA integrated into the genome of the cell.

In some embodiments, the isolated protein complex is preferably substantially free of a detergent. An isolated protein complex that is "substantially free of" a detergent does not include enough detergent to materially affect the activity or action of the Wnt in the isolated protein complex. In some embodiments "substantially free of a detergent" means containing less than 2% weight/volume (w/v), less than 1% (w/v), less than 0.5% (w/v), less than 0.1% (w/v), or less than 0.01% (w/v) of a detergent. In some embodiments, the detergent includes a zwitterionic and/or amphoteric detergent. In some embodiments, the detergent includes at least one of CHAPS (also referred to as 3-[(3-cholamidopropyl)dimethylammonio]-1-propanesulfonate), CHAPSO (also referred to as 3-([3-Cholamidopropyl]dimethylammonio)-2-hydroxy-1-propanesulfonate), Triton-X-100, Tween 20, Tween 80, SDS, deoxycholate, cholate, sarkosyl, DDM, digitonin, and urea. In some embodiments, the detergent includes CHAPS.

In another aspect, this disclosure describes a composition including a Wnt. The composition is preferably substantially free of a detergent. A composition that is "substantially free of" a detergent does not include enough detergent to materially affect the activity or action of the Wnt in the composition.

In some embodiments, the Wnt of the isolated protein complex or composition preferably includes active Wnt. As used herein, an "active Wnt" is a Wnt that activates canonical β-catenin signaling.

Canonical β-catenin signaling may be measured using any method known to a person having skill in the art. For example, canonical β-catenin signaling may be measured by assaying for Wnt mediated phosphorylation of β-catenin, LRP5, LRP6, GSK3B, Axin, and/or Dishevelled. Phosphorylation may be measured using Western blot. Autocrine and paracrine C57MG cells, cell transformation assays, and duplication of the embryonic axis in Xenopus laevis, or zebrafish, are also established assays to test for Wnt-mediated canonical β-catenin activity. (See, e.g., Shimizu et al., Cell Growth Differ. 1997, 8(12):1349-58; Wong et al., Mol. Cell. Biol. 1994, 14(9):6278-86; McMahon and Moon, Cell. 1989, 58(6):1075-1084; Lustig et al., Mol. Cell. Biol. 2002, 22(4):1184-93; Tamai et al., Mol. Cell. 2004, 13(1):149-156; Van Noort et al., J Biol Chem. 2002, 277(20):17901-17905; Molenaar et al., Cell. 1996, 86(3):391-399; Klein and Melton, Proc Natl Acad Sci USA 1996, 93(16):8455-8459.)

In some embodiments, canonical β-catenin signaling may be measured using a secreted alkaline phosphatase (SEAP) reporter assay including the HEK293 TCF9-SEAP hFz4/hLRP5 Wnt Reporter assay described in Example 1. In some embodiments, a protein complex including an active Wnt has a 2-fold or greater Wnt reporter activity than a complex not including a Wnt, as measured using the SEAP reporter assay. In some embodiments, a composition including an active Wnt has a 2-fold or greater Wnt reporter activity than a composition not including a Wnt, as measured using the SEAP reporter assay.

In some embodiments, an active Wnt or an isolated protein complex exhibits an effective dose of 50 percent ($ED_{50}$) of less than 1000 ng/mL, less than 500 ng/mL, less than 100 ng/mL, less than 50 ng/mL, less than 40 ng/mL, less than 30 ng/mL, less than 20 ng/mL, less than 15 ng/mL, less than 10 ng/mL, less than 8 ng/mL, less than 5 ng/mL, less than 4 ng/mL, less than 3 ng/mL, or less than 2 ng/mL, as measured using, for example, a HEK293 TCF9-SEAP hFz4/hLRP5 Wnt Reporter assay, as described herein.

In some embodiments, an active Wnt or an isolated protein complex exhibits an effective dose of 50 percent ($ED_{50}$) of at least 2 ng/mL, at least 3 ng/mL, at least 4 ng/mL, at least 5 ng/mL, at least 8 ng/mL, at last 10 ng/mL, at least 15 ng/mL, at least 20 ng/mL, at least 30 ng/mL, at least 40 ng/mL, at least 50 ng/mL, at least 100 ng/mL, or at least 500 ng/mL, as measured using, for example, a HEK293 TCF9-SEAP hFz4/hLRP5 Wnt Reporter assay, as described herein.

In some embodiments, the isolated protein complex or composition may include a Wnt-sFRP fusion protein. In some embodiments, the Wnt may be fused to the sFRP1 via a linker including, for example, a peptide linker. Any suitable linker may be used. In some embodiments, a peptide linker may include at least one of GGGS (SEQ ID NO:1), GGGGS (SEQ ID NO:2), GSGSG (SEQ ID NO:3), GGGGG (SEQ ID NO:4), and GSGSGGSGSG (SEQ ID NO:5). In some embodiments, the peptide linker may include multiple repeats of one or more of the peptide linkers described above including, for example, $(GGGS)_X$ (SEQ ID NO:6), $(GGGGS)_X$ (SEQ ID NO:7); $(GSGSG)_X$ (SEQ ID NO:8), $(GSGSGGSGSG)_X$ (SEQ ID NO:9), and/or $G_X$, where X=1-400.

In some embodiments, the isolated protein complex or composition may include a member of the R-Spondin family including, for example, at least one of R-Spondin 1, R-Spondin 2, R-Spondin 3, and R-Spondin 4.

In some embodiments, the R-Spondin may be fused to the sFRP1 and/or the Wnt, forming a fusion protein. In some embodiments, the R-Spondin may be fused to the sFRP1 and/or the Wnt via a linker including, for example, a peptide linker. Any suitable linker may be used. In some embodiments, a peptide linker may include at least one of GGGS (SEQ ID NO:1), GGGGS (SEQ ID NO:2), GSGSG (SEQ ID NO:3), GGGGG (SEQ ID NO:4), and GSGSGGSGSG (SEQ ID NO:5). In some embodiments, the peptide linker may include multiple repeats of one or more of the peptide linkers described above including, for example, $(GGGS)_X$ (SEQ ID NO:6), $(GGGGS)_X$ (SEQ ID NO:7); $(GSGSG)_X$ (SEQ ID NO:8), $(GSGSGGSGSG)_X$ (SEQ ID NO:9), and/or $G_X$, where X=1-400.

In some embodiments, the isolated protein complex or composition may include Lipocalin7. In some embodiments, the isolated protein complex or composition may include WIF1.

Methods of Making

In a further aspect, this disclosure describes a method that includes forming a complex including a Wnt and a sFRP and isolating the Wnt. In some embodiments, the Wnt may be isolated before forming a complex including a Wnt and a sFRP. In some embodiments, the Wnt may be isolated from a complex including a Wnt and a sFRP. In some embodiments, including when the Wnt is isolated from a complex including a Wnt and a sFRP, the Wnt may preferably be isolated without using a detergent.

In some embodiments, including, for example, when the Wnt is isolated before forming a complex including a Wnt and a sFRP, isolating the Wnt may include using a detergent. The detergent may include, for example, CHAPS. In some embodiments, the method may further include removing the detergent from the complex including the Wnt and the sFRP.

In some embodiments, isolating the Wnt may include an aqueous purification procedure. In some embodiments, isolating the Wnt may include chromatographic separation. Chromatographic separation may include, for example, separation using a SEPHAROSE column.

In some embodiments, the method may include producing and/or expressing at least one of the Wnt and the sFRP. In some embodiments, the Wnt and/or the sFRP may be overexpressed. The Wnt and/or the sFRP may be expressed in mammalian cells, yeast, bacteria, insect cells (S2, Sf9, Sf21), or other cells under the control of appropriate promoters. Cell-free translation systems may also be employed to produce the Wnt and/or the sFRP using RNAs. Appropriate cloning and expression vectors for use with prokaryotic and eukaryotic hosts are described by, for example, Sambrook, et al., Molecular Cloning: A Laboratory Manual, Second Edition, Cold Spring Harbor, N.Y. (1989).

In some embodiments, forming a complex including a Wnt and a sFRP may include co-culturing a Wnt-expressing cell with a sFRP expressing cell. In some embodiments, forming a complex including a Wnt and a sFRP may include co-culturing a Wnt-expressing cell with a sFRP-expressing cell.

In some embodiments, the method may include isolating conditioned media from a cell expressing the Wnt and the sFRP or from a co-culture of a Wnt-expressing cell with a sFRP expressing cell. In some embodiments, the method may further include isolating a complex including a Wnt and a sFRP from the conditioned media.

Methods of Using

In another aspect, this disclosure describes methods of using an isolated protein complex, as described herein. For example, the isolated protein complexes, isolated Wnt, and/or compositions described herein could be used as a media additive. In some embodiments, the media additive could be used in cell culture including, for example, a stem cell culture or an organoid culture. In some embodiments, the isolated protein complexes, isolated Wnt, and/or compositions described herein could be used in a disease model. In some embodiments, the isolated protein complexes, isolated Wnt, and/or compositions described herein could be used to direct differentiation of cells including, for example, embryonic stem cells or induced pluripotent stem cells. A cell may be differentiated to any desirable cell type including, for example, a neuron, neuroectoderm, a cardiac myocyte, a mesenchymal stem cell, and/or a mesendoderm derivative (see, e.g., Lam et al., 2014, Semin Nephrol, 34(4):445-461; Spence et al., 2011, Nature, 470:105-109; Paige et al., 2010, PLoS One 5(6):e11134. doi: 10.1371/journal.pone.0011134; Murashov et al., 2004 FASEB 19(2):252-4).

EXEMPLARY EMBODIMENTS

Isolated Protein Complex Embodiments
1. An isolated protein complex comprising a Wnt and a sFRP.
2. The isolated protein complex of Embodiment 1, wherein the Wnt comprises at least one of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.
3. The isolated protein complex of any one of the previous Embodiments, wherein the Wnt comprises at least one of Wnt3a, Wnt5a, Wnt5b, Wnt8a, and Wnt10a.
4. The isolated protein complex of any one of the previous Embodiments, wherein the sFRP comprises at least one of sFRP1, sFRP2, sFRP3, sFRP4, and sFRP5.
5. The isolated protein complex of any one of the previous Embodiments, wherein the Wnt comprises an active Wnt.
6. The isolated protein complex of Embodiment 5, wherein the active Wnt comprises Wnt that activates β-catenin signaling.
7. The isolated protein complex of Embodiment 5 or 6, wherein the active Wnt comprises Wnt having Wnt reporter activity as measured using a secreted alkaline phosphatase (SEAP) reporter assay.
8. The isolated protein complex of Embodiment 7, wherein the isolated protein complex has a 2-fold or greater Wnt reporter activity than an isolated protein complex that does not comprise a Wnt, as measured using the SEAP reporter assay.
9. The isolated protein complex of any one of the previous Embodiments, wherein the protein complex is substantially free of a detergent.
10. The isolated protein complex of any one of the previous Embodiments, wherein the protein complex exhibits an effective dose of 50 percent ($ED_{50}$) of less than 1000 ng/mL, less than 500 ng/mL, or less than 100 ng/mL as measured using a HEK293 TCF9-SEAP hFz4/hLRP5 Wnt Reporter assay.
11. The isolated protein complex of any one of the previous Embodiments, wherein the Wnt comprises a mammalian Wnt.
12. The isolated protein complex of any one of the previous Embodiments, wherein the Wnt comprises human Wnt or mouse Wnt.
13. The isolated protein complex of any one of the previous Embodiments, wherein the sFRP comprises a mammalian sFRP.
14. The isolated protein complex of any one of the previous Embodiments, wherein the sFRP comprises human sFRP or mouse sFRP.
15. The isolated protein complex of any one of the previous Embodiments, wherein the sFRP comprises a tagged sFRP.
16. The isolated protein complex of Embodiment 15, wherein the tagged sFRP comprises histidine-tagged sFRP.
17. The isolated protein complex of Embodiment 15 or 16, wherein the tagged sFRP comprises a C-terminal-tagged sFRP.
18. The isolated protein complex of any one of the previous Embodiments, wherein the Wnt comprises a tagged Wnt.
19. The isolated protein complex of Embodiment 18, wherein the tagged Wnt comprises a histidine-tagged Wnt.
20. The isolated protein complex of Embodiment 18 or 19, wherein the tagged Wnt comprises a C-terminal-tagged Wnt.
21. The isolated protein complex of any one of the previous Embodiments, wherein the complex comprises a Wnt-sFRP fusion protein.
22. The isolated protein complex of Embodiment 21, wherein the Wnt-sFRP fusion protein comprises a linker.
23. The isolated protein complex of Embodiment 22, wherein the linker comprises a peptide linker.
24. The isolated protein complex of any one of the previous Embodiments, the isolated protein complex further comprises at least one of R-Spondin 1, R-Spondin 2, R-Spondin 3, and R-Spondin 4.
25. The isolated protein complex of Embodiment 24, wherein the at least one of R-Spondin 1, R-Spondin 2, R-Spondin 3, and R-Spondin 4 is fused to the sFRP1, forming a fusion protein.
26. The isolated protein complex of Embodiment 25, wherein the at least one of R-Spondin 1, R-Spondin 2, R-Spondin 3, and R-Spondin 4 is fused the sFRP1 via a linker.
27. The isolated protein complex of Embodiment 26, wherein the linker comprises a peptide linker.
28. The isolated protein complex of any one of Embodiments 25 to 27, the fusion protein further comprising the Wnt.
29. The isolated protein complex of Embodiment 24 or Embodiment 28, wherein the at least one of R-Spondin 1, R-Spondin 2, R-Spondin 3, and R-Spondin 4 is fused to the Wnt, forming a fusion protein.

30. The isolated protein complex of Embodiment 29, wherein the at least one of R-Spondin 1, R-Spondin 2, R-Spondin 3, and R-Spondin 4 is fused the Wnt via a linker.
31. The isolated protein complex of Embodiment 30, wherein the linker comprises a peptide linker.
32. The isolated protein complex of any one of Embodiments 23, 27, or 31, wherein the peptide linker comprises at least one of GGGS (SEQ ID NO:1), GGGGS (SEQ ID NO:2), (SEQ ID NO:3), GGGGG (SEQ ID NO:4), and GSGSGGSGSG (SEQ ID NO:5).
33. The isolated protein complex of any one of the previous Embodiments, the isolated protein complex further comprising Lipocalin7.
34. The isolated protein complex of any one of the previous Embodiments, the isolated protein complex further comprising WIF1.
35. A method of using the isolated protein complex of any one of the previous Embodiments.

Wnt Composition Embodiments

1. A composition comprising a Wnt, wherein the composition is substantially free of a detergent.
2. The composition of Embodiment 1, wherein the Wnt comprises active Wnt.
3. A composition comprising a Wnt, wherein the Wnt comprises active Wnt.
4. The composition of either of Embodiments 2 or 3, wherein the active Wnt comprises Wnt that activates canonical β-catenin signaling.
5. The composition of either of Embodiments 2 or 3, wherein the active Wnt comprises Wnt having Wnt reporter activity as measured using a secreted alkaline phosphatase (SEAP) reporter assay.
6. The composition of Embodiment 5, wherein the composition has a 2-fold or greater Wnt reporter activity than a composition that does not comprise Wnt, as measured using the SEAP reporter assay.
7. The composition of any one of Embodiments 2 to 6, wherein the active Wnt exhibits an effective dose of 50 percent ($ED_{50}$) of less than 1000 ng/mL, less than 500 ng/mL, or less than 100 ng/mL as measured using a HEK293 TCF9-SEAP hFz4/hLRP5 Wnt Reporter assay.
8. The composition of any one of the previous Embodiments, wherein the Wnt comprises at least one of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.
9. The composition of any one of the previous Embodiments, wherein the Wnt comprises at least one of Wnt3a, Wnt5a, Wnt5b, Wnt8a, and Wnt10a.
10. The composition of any one of the previous Embodiments, wherein the Wnt comprises a mammalian Wnt.
11. The composition of any one of the previous Embodiments, wherein the Wnt comprises human Wnt or mouse Wnt.
12. The composition of any one of the previous Embodiments, the composition further comprising a sFRP.
13. The composition of Embodiment 12, wherein the sFRP comprises at least one of sFRP1, sFRP2, sFRP3, sFRP4, and sFRP5.
14. The composition of either of Embodiments 12 or 13, wherein the composition comprises a Wnt-sFRP fusion protein.
15. The composition of Embodiment 14, wherein the Wnt-sFRP fusion protein comprises a linker.
16. The composition of Embodiment 15, wherein the linker comprises a peptide linker.
17. The composition of any one of Embodiments 12 to 15 wherein the sFRP comprises a mammalian sFRP.
18. The composition of any one of Embodiments 12 to 17, wherein the sFRP comprises human sFRP or mouse sFRP.
19. The composition of any one of Embodiments 12 to 18, wherein the sFRP comprises tagged sFRP.
20. The composition of Embodiment 19, wherein the tagged sFRP comprises histidine-tagged sFRP.
21. The composition of Embodiment 20 or 21, wherein the tagged sFRP comprises a C-terminal-tagged sFRP.
22. The composition of any one of the previous Embodiments, wherein the Wnt comprises tagged Wnt.
23. The composition of Embodiment 22, wherein the tagged Wnt comprises histidine-tagged Wnt.
24. The composition of Embodiment 22 or 23, wherein the tagged Wnt comprises a C-terminal tagged Wnt.
25. The composition of any one of the previous Embodiments, the composition further comprising at least one of R-Spondin 1, R-Spondin 2, R-Spondin 3, and R-Spondin 4.
26. The composition of Embodiment 25, wherein the at least one of R-Spondin 1, R-Spondin 2, R-Spondin 3, and R-Spondin 4 is fused to the Wnt, forming a fusion protein.
27. The composition of Embodiment 23, wherein the at least one of R-Spondin 1, R-Spondin 2, R-Spondin 3, and R-Spondin 4 is fused the Wnt via a peptide linker.
28. The composition of any one of Embodiments 25 to 27, the composition comprising a sFRP, and wherein the at least one of the Wnt, R-Spondin 1, R-Spondin 2, R-Spondin 3, and R-Spondin 4 is fused to the sFRP, forming a fusion protein.
29. The composition of Embodiment 28, wherein the at least one of the Wnt, R-Spondin 1, R-Spondin 2, R-Spondin 3, and R-Spondin 4 is fused the sFRP via a peptide linker.
30. The composition of Embodiment 16, 27, or 29, wherein the peptide linker comprises at least one of GGGS (SEQ ID NO:1), GGGGS (SEQ ID NO:2), (SEQ ID NO:3), GGGGG (SEQ ID NO:4), and GSGSGGSGSG (SEQ ID NO:5).
31. The composition of any one of the previous Embodiments, the composition further comprising Lipocalin7.
32. The composition of any one of the previous Embodiments, the composition further comprising WIF1.
33. A method of using the composition of any one of the previous Embodiments.

Cell Embodiments

1. A cell overexpressing a Wnt and a sFRP.
2. The cell of Embodiment 1, wherein the Wnt comprises at least one of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.
3. The cell of any one of the previous Embodiments, wherein the Wnt comprises at least one of Wnt3a, Wnt5a, Wnt5b, Wnt8a, and Wnt10a.
4. The cell of any one of the previous Embodiments, wherein the sFRP comprises at least one of sFRP1, sFRP2, sFRP3, sFRP4, and sFRP5.
5. The cell of any one of the previous Embodiments, wherein the Wnt comprises an active Wnt.
6. The cell of Embodiment 5, wherein the active Wnt comprises Wnt that activates β-catenin signaling.

7. The cell of any one of the previous Embodiments, wherein the Wnt exhibits an effective dose of 50 percent ($ED_{50}$) of less than 1000 ng/mL, less than 500 ng/mL, or less than 100 ng/mL as measured using a HEK293 TCF9-SEAP hFz4/hLRP5 Wnt Reporter assay.
8. The cell of any one of the previous Embodiments, wherein the Wnt comprises a mammalian Wnt.
9. The cell of any one of the previous Embodiments, wherein the Wnt comprises human Wnt or mouse Wnt.
10. The cell of any one of the previous Embodiments, wherein the sFRP comprises a mammalian sFRP.
11. The cell of any one of the previous Embodiments, wherein the sFRP comprises human sFRP or mouse sFRP.
12. The cell of any one of the previous Embodiments, wherein the sFRP comprises tagged sFRP.
13. The cell of Embodiment 12, wherein the tagged sFRP comprises histidine-tagged sFRP.
14. The cell of Embodiment 12 or 13, wherein the tagged sFRP comprises C-terminal-tagged sFRP.
15. The cell of any one of the previous Embodiments, wherein the Wnt comprises tagged Wnt.
16. The cell of Embodiment 15, wherein the tagged Wnt comprises histidine-tagged Wnt.
17. The cell of Embodiment 15 or 16, wherein the tagged Wnt comprises C-terminal-tagged Wnt.
18. The cell of any one of the previous Embodiments, wherein the cell expresses a Wnt-sFRP fusion protein.
19. The cell of Embodiment 18, wherein the Wnt-sFRP fusion protein comprises a linker.
20. The cell of Embodiment 19, wherein the linker comprises a peptide linker.
21. The cell of any one of the previous Embodiments, the cell further expressing at least one of R-Spondin 1, R-Spondin 2, R-Spondin 3, and R-Spondin 4.
22. The cell of Embodiment 21, wherein the at least one of R-Spondin 1, R-Spondin 2, R-Spondin 3, and R-Spondin 4 is fused to the sFRP1, forming a fusion protein.
23. The cell of Embodiment 22, wherein the at least one of R-Spondin 1, R-Spondin 2, R-Spondin 3, and R-Spondin 4 is fused the sFRP1 via a linker.
24. The cell of Embodiment 23, wherein the linker comprises a peptide linker.
25. The cell of any one of Embodiments 22 to 27, the fusion protein further comprising the Wnt.
26. The cell of Embodiment 21 or Embodiment 25, wherein the at least one of R-Spondin 1, R-Spondin 2, R-Spondin 3, and R-Spondin 4 is fused to the Wnt, forming a fusion protein.
27. The cell of Embodiment 26, wherein the at least one of R-Spondin 1, R-Spondin 2, R-Spondin 3, and R-Spondin 4 is fused the Wnt via a linker.
28. The cell of Embodiment 27, wherein the linker comprises a peptide linker.
29. The cell of any one of Embodiments 20, 24, or 28, wherein the peptide linker comprises at least one of GGGS (SEQ ID NO:1), GGGGS (SEQ ID NO:2), (SEQ ID NO:3), GGGGG (SEQ ID NO:4), and GSGSGGSGSG (SEQ ID NO:5).
30. A method of using the cell of any one of the previous Embodiments.

Cell Composition Embodiments
1. A composition comprising:
   a cell overexpressing a Wnt; and
   a cell overexpressing a sFRP.
2. The composition of Embodiment 1, wherein the Wnt comprises at least one of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.
3. The composition of any one of the previous Embodiments, wherein the Wnt comprises at least one of Wnt3a, Wnt5a, Wnt5b, Wnt8a, and Wnt10a.
4. The composition of any one of the previous Embodiments, wherein the sFRP comprises at least one of sFRP1, sFRP2, sFRP3, sFRP4, and sFRP5.
5. The composition of any one of the previous Embodiments, wherein the Wnt comprises an active Wnt.
6. The composition of Embodiment 5, wherein the active Wnt comprises Wnt that activates β-catenin signaling.
7. The composition of any one of the previous Embodiments, wherein the Wnt exhibits an effective dose of 50 percent ($ED_{50}$) of less than 1000 ng/mL, less than 500 ng/mL, or less than 100 ng/mL as measured using a HEK293 TCF9-SEAP hFz4/hLRP5 Wnt Reporter assay.
8. The composition of any one of the previous Embodiments, wherein the Wnt comprises a mammalian Wnt.
9. The composition of any one of the previous Embodiments, wherein the Wnt comprises human Wnt or mouse Wnt.
10. The composition of any one of the previous Embodiments, wherein the sFRP comprises a mammalian sFRP.
11. The composition of any one of the previous Embodiments, wherein the sFRP comprises human sFRP or mouse sFRP.
12. The composition of any one of the previous Embodiments, wherein the sFRP comprises tagged sFRP.
13. The composition of Embodiment 12, wherein the tagged sFRP comprises histidine-tagged sFRP.
14. The composition of Embodiment 12 or 13, wherein the tagged sFRP comprises C-terminal-tagged sFRP.
15. The composition of any one of the previous Embodiments, wherein the Wnt comprises tagged Wnt.
16. The composition of Embodiment 15, wherein the tagged Wnt comprises histidine-tagged Wnt.
17. The composition of Embodiment 15 or 16, wherein the tagged Wnt comprises C-terminal-tagged Wnt.
18. The composition of any one of the previous Embodiments, the composition further comprising a cell expressing at least one of R-Spondin 1, R-Spondin 2, R-Spondin 3, and R-Spondin 4.
19. The composition of Embodiment 18, wherein the at least one of R-Spondin 1, R-Spondin 2, R-Spondin 3, and R-Spondin 4 is fused to the sFRP1, forming a fusion protein.
20. The composition of Embodiment 19, wherein the at least one of R-Spondin 1, R-Spondin 2, R-Spondin 3, and R-Spondin 4 is fused the sFRP1 via a linker.
21. The composition of Embodiment 20, wherein the linker comprises a peptide linker.
22. The composition of Embodiment 18, wherein the at least one of R-Spondin 1, R-Spondin 2, R-Spondin 3, and R-Spondin 4 is fused to the Wnt, forming a fusion protein.
23. The composition of Embodiment 22, wherein the at least one of R-Spondin 1, R-Spondin 2, R-Spondin 3, and R-Spondin 4 is fused the Wnt via a linker.
24. The composition of Embodiment 23, wherein the linker comprises a peptide linker.

25. The composition of Embodiments 21 or 24, wherein the peptide linker comprises at least one of GGGS (SEQ ID NO:1), GGGGS (SEQ ID NO:2), (SEQ ID NO:3), GGGGG (SEQ ID NO:4), and GSGSGGSGSG (SEQ ID NO:5).

26. The composition of any one of the previous Embodiments, wherein at least one of the cell overexpressing a Wnt and the cell overexpressing a sFRP is transfected with a plasmid.

27. A method of using the composition of any one of the previous Embodiments.

Method Embodiments

1. A method comprising:
   forming a complex comprising a Wnt and a sFRP; and isolating the Wnt.

2. The method of any one of the previous Embodiments, wherein isolating the Wnt comprises an aqueous purification procedure.

3. The method of any one of the previous Embodiments, wherein isolating the Wnt comprises chromatographic separation.

4. The method of any one of the previous Embodiments, the method further comprising overexpressing the Wnt.

5. The method of any one of the previous Embodiments, the method further comprising overexpressing the sFRP.

6. The method of any one of the previous Embodiments, wherein forming a complex comprising a Wnt and a sFRP comprises co-culturing a Wnt-expressing cell with a sFRP expressing cell.

7. The method of any one of the previous Embodiments, wherein the complex comprising a Wnt and a sFRP is formed after isolating the Wnt, 8. The method of any one of the previous Embodiments, wherein isolating the Wnt comprises using a detergent.

9. The method of any one Embodiments 1 to 7, wherein the complex comprising a Wnt and a sFRP is formed before isolating the Wnt.

10. The method of any one of Embodiment 1 to 7 or 9, wherein isolating the Wnt does not comprise using a detergent.

11. The method of any one of the previous Embodiments, wherein the Wnt comprises at least one of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.

12. The method of any one of the previous Embodiments, wherein the Wnt comprises at least one of Wnt3a, Wnt5a, Wnt5b, Wnt8a, and Wnt10a.

13. The method of any one of the previous Embodiments, wherein the sFRP comprises at least one of sFRP1, sFRP2, sFRP3, sFRP4, and sFRP5.

14. The method of any one of the previous Embodiments, wherein the Wnt comprises a mammalian Wnt.

15. The method of any one of the previous Embodiments, wherein the Wnt comprises human Wnt or mouse Wnt.

16. The method of any one of the previous Embodiments, wherein the sFRP comprises a mammalian sFRP.

17. The method of any one of the previous Embodiments, wherein the sFRP comprises human sFRP or mouse sFRP.

18. The method of any one of the previous Embodiments, wherein the sFRP comprises tagged sFRP.

19. The method of Embodiment 18, wherein the tagged sFRP comprises histidine-tagged sFRP.

20. The method of Embodiment 18 or 19, wherein the tagged sFRP comprises C-terminal-tagged sFRP.

21. The method of any one of the previous Embodiments, wherein the Wnt comprises a tagged Wnt.

22. The method of Embodiment 21, wherein the tagged Wnt comprises a histidine-tagged Wnt.

23. The method of Embodiment 21 or 22, wherein the tagged Wnt comprises a C-terminal-tagged Wnt.

24. The method of any one of the previous Embodiments, wherein the complex further comprises at least one of R-Spondin 1, R-Spondin 2, R-Spondin 3, R-Spondin 4, Lipocaline7, and WIF1.

25. The method of any one of the previous Embodiments, the method comprising culturing a cell expressing the Wnt.

26. The method of any one of the previous Embodiments, the method comprising culturing a cell expressing the sFRP.

27. The method of claim 26, wherein the cell overexpressing the Wnt and the cell expressing the sFRP are co-cultured.

28. The method of any one of the previous Embodiments, the method comprising culturing a cell expressing the Wnt and the sFRP.

29. The method of any one of Embodiments 25 to 28, the method further comprising isolating the conditioned media.

30. The method of Embodiment 29, the method comprising isolating the complex comprising the Wnt and the sFRP from the conditioned media.

31. The method of any one of the previous Embodiments, the method further comprising removing a detergent from the complex comprising the Wnt and the sFRP.

32. The method of any one of the previous Embodiments, the method further comprising using the complex as a media additive.

33. The method of any one of the previous Embodiments, the method further comprising adding the complex to a stem cell culture or an organoid culture.

The present invention is illustrated by the following examples. It is to be understood that the particular examples, materials, amounts, and procedures are to be interpreted broadly in accordance with the scope and spirit of the invention as set forth herein.

EXAMPLES

Example 1

This Example describes a method of purifying Wnt proteins that eliminates the use of detergents but maintains the activity of recombinant Wnt proteins. The method includes co-expressing sFRPs that bind to Wnts. Without wishing to be bound by theory, it is believed that the sFRPs protect the lipid modification of the Wnt proteins from the aqueous environment. The data presented herein also demonstrate that sFRPs may be used to complex with and enhance the amount of active Wnt in the conditioned media of cells producing Wnts.

Methods

Cell Culture and Cell Transfection

All cell lines, including CHO, CHO mWnt-1, CHO msFRP-1, CHO mWnt-1/msFRP-1 and CHO mWnt-1/msFRP-1-His, were cultured in IMDM (ThermoFisher Scientific, Waltham, Mass.), 5% FBS (Corning, Corning, N.Y.) with 2 millimolar (mM) L-Glutamine-Penicillin-Streptomycin (Sigma), as well as appropriate selection antibiotics (Puromycin, G418, and/or Hygromycin; all from ThermoFisher Scientific, Waltham, Mass.). Cells were transfected with expression plasmids using Lipofectamine 2000 reagent according to the instructions of the manufacture (ThermoFisher Scientific, Waltham, Mass.).

To obtain conditioned media for a HEK293 TCF9-SEAP hFz4/hLRP5 Wnt Reporter assay and Western blots, $5\times10^4$ cells were seeded in a 12-well dish and incubated at 37° C., 5% $CO_2$ in an incubator for four days. The conditioned media (that is the supernatants) were collected and the cell debris was removed by centrifugation.

HEK293 TCF9-SEAP hFz4/hLRP5 Wnt Reporter Assay

Clonal HEK293 cells expressing full length human LRP5, full length human FZ4, and 9×T-Cell Factor DNA binding sites (TCF9) upstream of secreted alkaline phosphatase (SEAP) were seeded in 96-well plate and incubated overnight at 37° C.+5% $CO_2$. Then the cells were treated with either conditioned media or protein for 18 hours. After heat inactivation of endogenous alkaline phosphatase, 10 microliters (μL) of conditioned medium from each well was mixed with 50 μL SEAP Reporter Assay Buffer/Substrate (0.1 M Tris-HCl, pH 9.0, 0.1 mM DiFMUP (ThermoFisher Scientific, Waltham, Mass.)) and incubated in dark at room temperature for 15 minutes to 30 minutes. SEAP activity was measured with excitation at 350 nanometers (nm), emission at 450 nm, and 435 nm cut-off on a microplate reader (Spectra Max Gemini EM, Molecular Devices, LLC, Sunnyvale, Calif.).

Western Blot Analysis

Conditioned media or recombinant proteins were lysed in 2× reducing sample buffer (20 mM dithiothreitol, 6% SDS, 0.25 molar (M) Tris, pH 6.8, 10% glycerol, 10 mM NaF and bromophenyl blue) denatured at 95° C. for 3 minutes and resolved on 4-20% SDS-PAGE gels. The gels were transferred to PVDF membranes (Millipore, Billerica, Mass.) and incubated with primary antibody in blocking buffer (25 mM Tris, pH 7.4, 0.15 M NaCl, 0.1% Tween-20) containing 5% nonfat dry milk at 4° C. overnight. After extensive washings, the membranes were incubated with secondary antibody in blocking buffer at room temperature for 1 hour. The immunolabeling was revealed by a chemiluminescence reaction using the SuperSignal West Pico Chemiluminescent Substrate (ThermoFisher Scientific, Waltham, Mass.). Antibodies used for Western blotting were as follows; GtxmWnt-1, 1 μg/mL (Catalog No. AF1620, Bio-Techne, Minneapolis, Minn.). GtxhsFRP-1, 1 μg/mL (Catalog No. AF1384, Bio-Techne, Minneapolis, Minn.). DkxGt IgG, HRP, 1:1000 dilution (Catalog No. HAF109, Bio-Techne, Minneapolis, Minn.).

Immunoprecipitation of mWnt1 and msFRP1

$5\times10^4$ of CHO mWnt-1/msFRP1 cells were seeded in a 12-well dish and incubated at 37° C., 5% $CO_2$ in an incubator for four days. The conditioned media were collected and the cell debris removed by centrifugation. 500 μL of conditioned media were first incubated with immunoprecipitation antibody for 2 hours to 4 hours at 4° C., and then 50 μL of protein G-agarose beads (Pierce Protein Biology/ThermoFisher Scientific, Waltham, Mass.) was added and incubated for 2 hours. The bound immune complexes were recovered and washed three times in Dulbecco's phosphate-buffered saline (DPBS). Proteins were resolved by SDS-PAGE, transferred to PVDF membrane for Western blot analysis. Antibodies used for immunoprecipitations and Western blotting were as follows; GtxmWnt-1, 1 μg/mL (Catalog No. AF1620, Bio-Techne, Minneapolis, Minn.). MsxHis, 1 μg/mL (Catalog No. MAB050R, Bio-Techne, Minneapolis, Minn.). DkxGt IgG, HRP, 1:1000 dilution (Catalog No. HAF109, Bio-Techne, Minneapolis, Minn.). GtxMs IgG, HRP (Catalog No. HAF007, Bio-Techne, Minneapolis, Minn.).

Immunoprecipitation of CHO mWnt2b/msFRP1 Conditioned Media $5\times10^4$ of CHO mWnt2b/msFRP1 cells were seeded in the 12-well dish and incubated at 37° C., 5% $CO_2$ in an incubator for four days. The conditioned media were collected and the cell debris removed by centrifugation. 500 μL of conditioned media were first incubated with immunoprecipitation antibody for 2 hours to 4 hours at 4° C., and then 50 μL of protein G-agarose beads (Pierce Protein Biology/ThermoFisher Scientific, Waltham, Mass.) was added and incubated for 2 hours. The bound immune complexes were recovered and washed three times in DPBS. Proteins were resolved by SDS-PAGE, transferred to PVDF membrane for Western blot analysis. Antibodies used for immunoprecipitations and Western blotting were as follows; GtxmWnt2b, 1 μg/mL (Catalog No. AF3900, Bio-Techne, Minneapolis, Minn.). GtxhsFRP-1, 1 μg/mL (Catalog No. AF1384 Bio-Techne, Minneapolis, Minn.). DkxGt IgG, HRP, 1:1000 dilution (Catalog No. HAF109, Bio-Techne, Minneapolis, Minn.).

Co-Culture of Wnt Expressing Cells with msFRP Expressing Cells $5\times10^4$ Wnt expressing cells were seeded in a 12-well dish and incubated at 37° C., 5% $CO_2$ incubator for three days. $2\times10^5$ of msFRP expressing cells were added to the Wnt expressing cells and co-cultured for one day. The conditioned media were collected and applied to HEK293 Wnt reporter cells.

CHO mWnt-1 Cell Treatment with sFRP-1 Protein

A 12-well plate was seeded with $4\times10^5$ CHO mWnt-1 cells in 0.6 milliliter (mL) culture media. The cells were incubated at 37° C. for 1 hour and then added msFRP-1 protein treatment, starting from 50 μg/mL and serial diluted at 1:2. After 24 hours the conditioned media was collected by being centrifuged for 5 minutes to remove cell debris before being added the reporter cells.

Purification of Mouse Wnt-1/Mouse sFRP Complex

The conditioned media from CHO cells that co-expressed mouse Wnt-1 and mouse sFRP1 were loaded onto a SP sepharose Fast Flow column (GE Healthcare, Chicago, Ill.) equilibrated with 20 mM MOPS, 0.1 M NaCl, pH 6.8. A linear gradient of high salt buffer (20 mM MOPS, 1.6 M NaCl, pH 6.8) was applied to elute the bound proteins. The SDS-PAGE with silver staining was used to monitor elution of mouse sFRP1 (~37 kDa), while the Western blot probed with anti-mouse Wnt-1 was used to monitor elution of mouse Wnt-1 (~40 kDa). The protein peak that included both Wnt-1 and sFRP1 was collected. After concentrating, the pooled peak was loaded onto a Superdex-200 column (GE Healthcare, Chicago, Ill.) to separate Wnt-1/sFRP1 complex from free sFRP1, monitored by both SDS-PAGE silver staining and Western blot as in the previous step.

Wnt3a/sFRP ELISA Binding Assays

A 96-well tissue culture plate was blocked with 1% BSA in PBS and used as an in-solution binding plate. 120 μL of total volume containing 100 ng/mL recombinant mouse (rm) Wnt3a biotinylated protein and sFRPs (1:3 serial dilution) were incubated overnight at 4° C. in the binding plate. Then 100 μL of binding solution was transferred to streptavidin coated 96-well ELISA plate, incubating overnight at 4° C. followed by the HRP detection. The mouse sFRP1 was detected with a goat anti-mouse sFRP1 antibody, mouse sFRP2 and mouse sFRP3 were His-tagged and were detected with a mouse anti-His antibody, mouse sFRP4 was detected with a sheep anti-mouse sFRP4 antibody, and the HA-tagged mouse sFRP5 was detected with a mouse anti-HA peptide. Anti-HRP secondary antibodies were used to detect the primary antibodies followed by colorimetric readouts.

Results

To determine if expressing mouse sFRP1 (msFRP1) or mouse sFRP1-His (msFRP1-His) would enhance the amount of mouse Wnt1 (mWnt1) in the conditioned media (CM) of CHO cells, stable, clonal lines expressing mWnt1, msFRP1, mWnt1 and msFRP1, and mWnt1 and msFRP1-His were made. Western blot analysis of conditioned media demonstrated that co-expression of mWnt1 along with msFRP1 or msFRP1-His resulted in significantly higher levels of mWnt1 in the conditioned media compared to CHO, CHO mWnt1 or CHO msFRP1 conditioned media (FIG. 1A). CHO cells overexpressing msFRP1 also clearly showed higher levels of msFRP1 compared to msFRP1 levels in CHO, or CHO mWnt1 conditioned media (FIG. 1A).

Figure 1B:
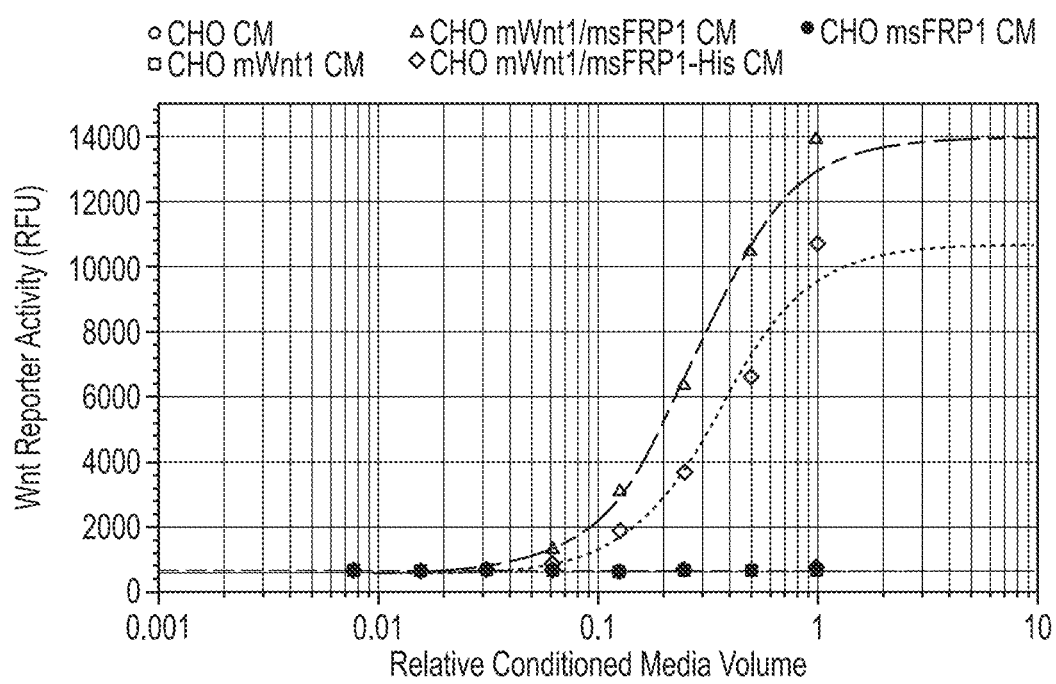
FIG. 1B. Conditioned media from CHO cells (blue circles), CHO mWnt1 (red squares), CHO mWnt1/msFRP1 (green triangles), CHO mWnt1/msFRP1-His (orange diamonds) and CHO msFRP1 (red circles) were added to HEK293 TCF9-SEAP hFz4/hLRP5 Wnt Reporter cells starting at the highest concentration of media and diluting 1:2. Only when CHO cells expressed mWnt1 and msFRP1 or msFRP1-His together was Wnt1 activity detected in the conditioned media. The conditioned media from CHO-s mWnt1/msFRP1 cells (green triangles) resulted in a 22-fold induction while the CHO mWnt1/msFRP-His (orange diamonds) resulted in a 17-fold induction above background in this HEK293 TCF9-SEAP hFz4/hLRP5 Wnt Reporter assay. Conditioned media from the other CHO lines did not induce activity in the HEK293 TCF9-SEAP hFz4/hLRP5 Wnt Reporter cell line.

The same conditioned media used in Western blot analysis of FIG. 1A was also tested in a HEK293 Wnt Reporter line that expresses human Frizzled4 (hFz4) and human LRP5 (hLRP5) (also referred to herein as conducting an HEK293 hFz4/hLRP5 Wnt reporter assay). Conditioned media from CHO cells resulted in Wnt reporter activation only when mWnt1 was co-expressed with msFRP1 or msFRP1-His (FIG. 1B). Wild type CHO, CHO mWnt1, and CHO msFRP1 conditioned media did not activate the Wnt reporter at a level beyond background. These data are consistent with msFRP1 or msFRP1-His overexpression resulting in higher levels of active mWnt1 in the conditioned media of cells expressing both mWnt1 and msFRP1 or msFRP1-His (FIG. 1).

Figure 2A:
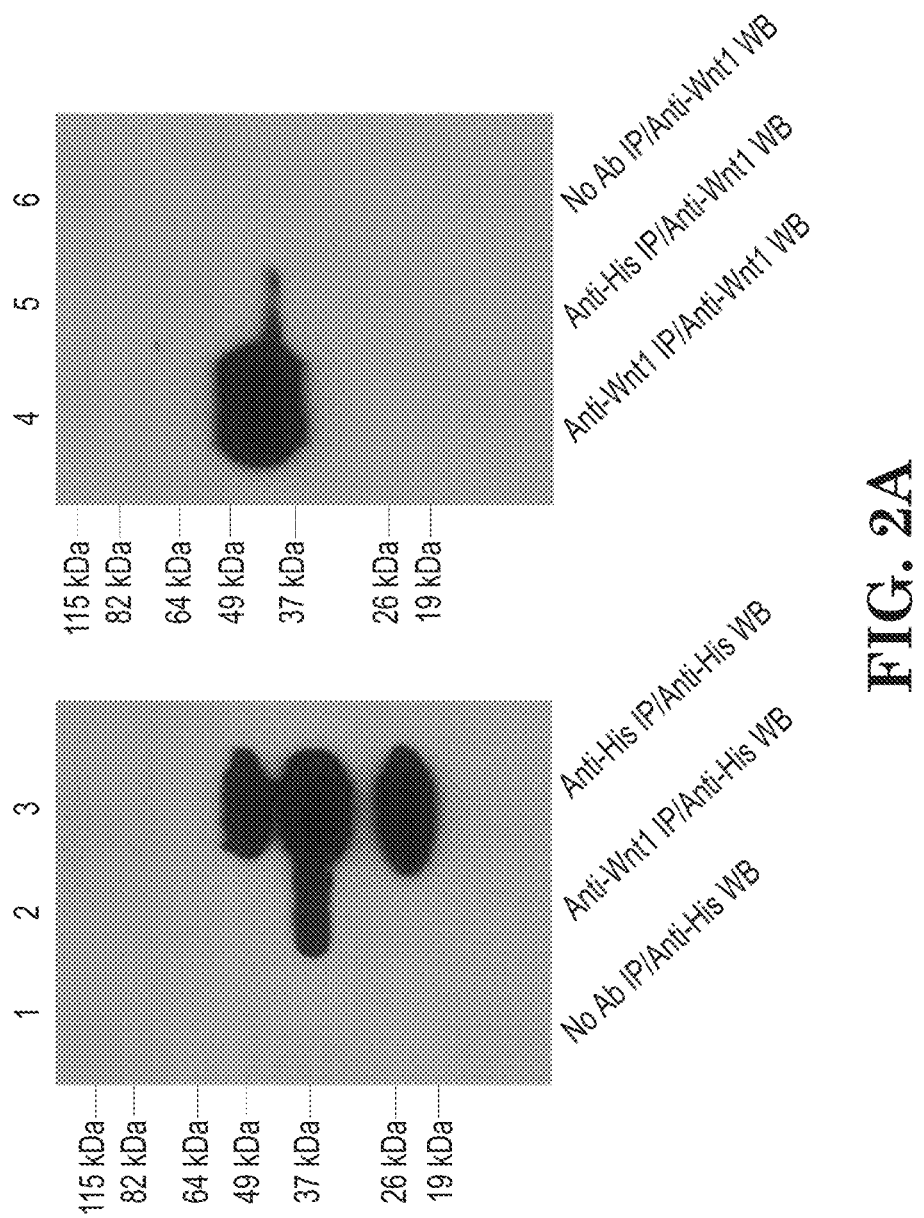
FIG. 2A shows msFRP1-His binds to mWnt1 in CHO conditioned media expressing both mWnt1 and msFRP1-His. Immunoprecipitation experiments were performed by adding anti-Wnt1 antibody (lane 2, lane 4), anti-His antibody (lane 3, lane 5), or no antibody control (lane 1, lane 6) to equal amounts of CHO cell conditioned media overexpressing both mWnt1 and msFRP1-His. The antibody/conditioned media mixtures were complexed to protein G agarose beads and immunoprecipitation experiments were performed. When no antibody was added to the CHO mWnt1/msFRP/His expressing conditioned media, msFRP1 and mWnt1 were not detected in Western blots (lanes 1 and 6 respectively). When an anti-mWnt1 antibody was used to immunoprecipitate, the His tagged msFRP1/His protein was detected at around 37 kilodaltons (kDa) when blotted with an anti-His antibody (lane 2). When an anti-His antibody was used to immunoprecipitate, the anti-mWnt1 antibody detected a mWnt1 band at around 42 kDa (lane 5). The bands at 50 kDa and 25 kDa in lane 3 are heavy and light chain IgGs being recognized by the anti-His antibody.

To test if a Wnt and a sFRP could bind to each other in a complex, the interaction of mWnt1 and msFRP1 was tested. Immunoprecipitation experiments demonstrated that mWnt1 and msFRP1-His are bound in a complex (FIG. 2). Immunoprecipitation with an anti-Wnt1 antibody and blotting with an anti-His antibody resulted in the detection of a band of 37 kDa, the expected size of msFRP1-His (FIG. 2, lane 2). Immunoprecipitation with an anti-His antibody and blotting with an anti-Wnt1 antibody resulted in the detection of a band of 42 kDa, the expected size of mWnt1 (FIG. 2, lane 5). These data suggest that mWnt1 and msFRP1 are bound to each other in a complex in the conditioned media of CHO cells expressing both mWnt1 and msFRP1.

Figures 2B, 2C:
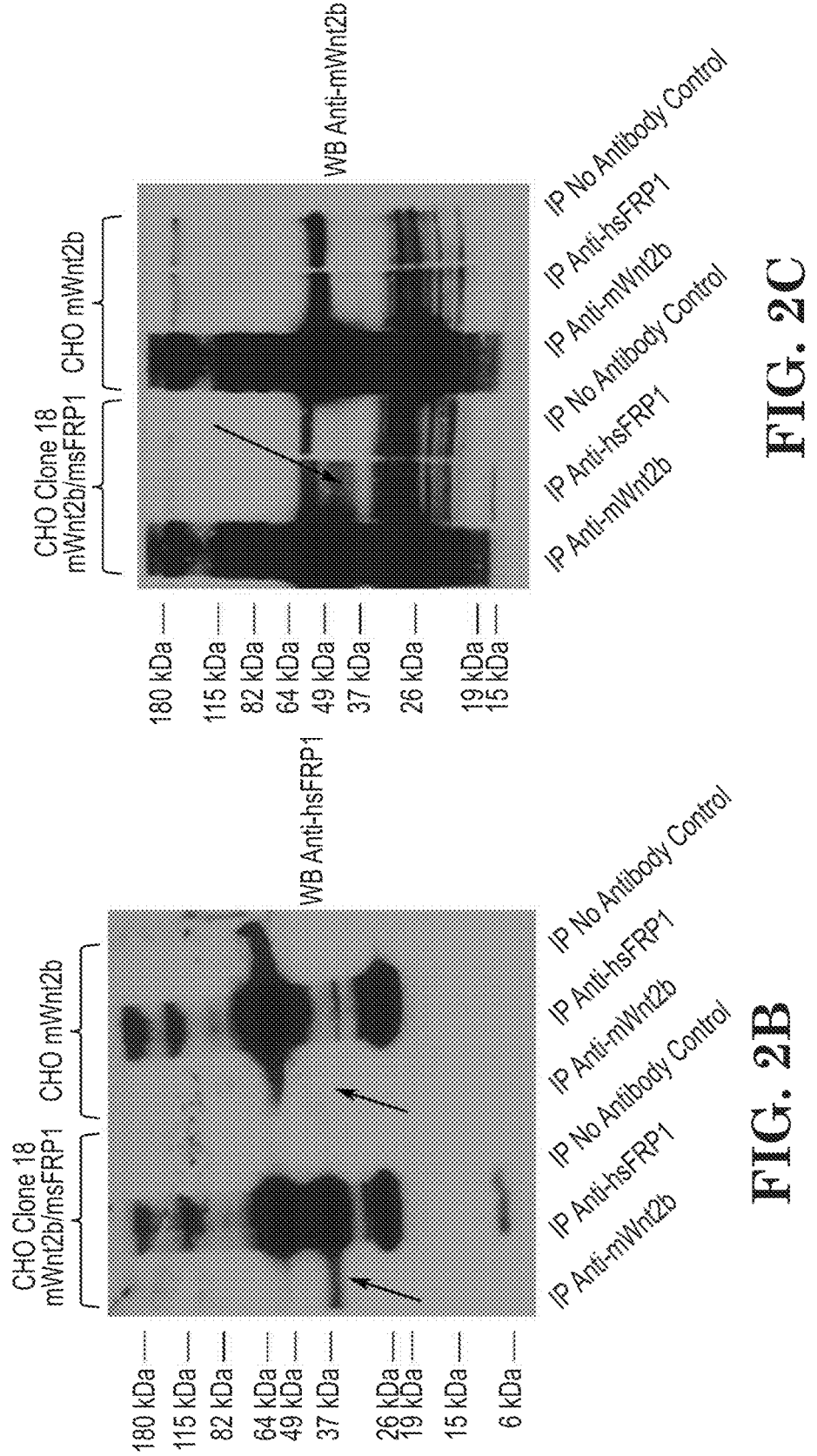
FIG. 2B shows msFRP1 binds to mWnt2b in CHO conditioned media expressing both mWnt2b and msFRP1. Immunoprecipitation experiments were performed by adding anti-mouse Wnt2b, anti-human sFRP1, or no antibody control to equal amounts of CHO cell conditioned media overexpressing mWnt2b alone or mWnt2b and msFRP1 (Clone 18). Immunoprecipitation with anti-mWnt2b antibodies followed by blotting with anti-hsFRP1 antibodies resulted in the detection of sFRP1 protein at around 35 kDa (indicated by black arrows), demonstrating that mWnt2b and msFRP1 are physically interacting in the conditioned media of CHO cells expressing both mWnt2b and msFRP1. This 35 kDa band was not detected in the conditioned media of CHO cells expressing only mWnt1 when immunoprecipitations were performed with anti-mWnt2b and blotted with anti-hsFRP1.
FIG. 2C shows msFRP1 binds to mWnt2b in CHO conditioned media expressing both mWnt2b and msFRP1. Immunoprecipitation experiments were performed by adding anti-Wnt2b, anti-hsFRP1, or no antibody control to equal amounts of CHO cell conditioned media overexpressing mWnt2b alone or mWnt2b and msFRP1 (Clone 18). Immunoprecipitation with anti-hsFRP1 antibodies followed by blotting with anti-mWnt2b antibodies resulted in the detection of mWnt2b protein at around 42 kDa (indicated by black arrow), demonstrating that mWnt2b and msFRP1 are physically interacting in the conditioned media of CHO cells expressing both mWnt2b and msFRP1. This 42 kDa mWnt1 band was not detected in the conditioned media of CHO cells expressing only mWnt1 when immunoprecipitations were performed with anti-hsFRP1 and blotted with anti-mWnt1.

To test if mouse sFRP1 (msFRP1) binds to mWnt2b in CHO conditioned media expressing both mouse Wnt2b (mWnt2b) and msFRP1. Immunoprecipitation experiments were performed by adding anti-Wnt2b, anti-hsFRP1, or no antibody control to equal amounts of CHO cell conditioned media overexpressing mWnt2b alone or mWnt2b and msFRP1 (Clone 18). FIG. 2B shows that immunoprecipitation with anti-mWnt2b antibodies followed by blotting with anti-hsFRP1 antibodies resulted in the detection of sFRP1 protein at around 35 kDa (arrows in FIG. 2B), demonstrating that mWnt2b and msFRP1 are physically interacting in the conditioned media of CHO cells expressing both mWnt2b and msFRP1. This 35 kDa band was not detected in the conditioned media of CHO cells expressing only mWnt1 when immunoprecipitations were performed with anti-mWnt2b and blotted with anti-hsFRP1.

Further immunoprecipitation experimentation demonstrates that msFRP1 does bind to mWnt2b in CHO conditioned media expressing both mWnt2b and msFRP1. Immunoprecipitation experiments were performed by adding anti-Wnt2b, anti-hsFRP1, or no antibody control to equal amounts of CHO cell conditioned media overexpressing mWnt2b alone or mWnt2b and msFRP1 (Clone 18). FIG. 2C shows that immunoprecipitation with anti-hsFRP1 antibodies followed by blotting with anti-mWnt2b antibodies resulted in the detection of mWnt2b protein at around 42 kDa (arrow in FIG. 2C), demonstrating that mWnt2b and msFRP1 are physically interacting in the conditioned media of CHO cells expressing both mWnt2b and msFRP1. This 42 kDa mWnt1 band was not detected in the conditioned media of CHO cells expressing only mWnt1 when immunoprecipitations were performed with anti-hsFRP1 and blotted with anti-mWnt1.

Further experiments were designed to understand why an increase in levels of active mWnt1 was observed in the conditioned media of cells expressing both mWnt1 and msFRP1. When CHO cells expressing only mWnt1 were co-cultured with HEK293 hFz4/hLRP5 Wnt reporter cells (also referred to herein as HEK293 Wnt reporter cells), robust activation of Wnt reporter activity is detected, demonstrating that CHO cells expressing mWnt1 make active mWnt1 protein (Table 1, row 3). When the conditioned media from CHO mWnt1 cells is added to HEK293 Wnt reporter cells, no Wnt reporter activation is detected (Table 1, row 4). These data suggest that the active mWnt1 protein is not in the conditioned media, but rather is localized on the cell surface of the CHO mWnt1 cells. When CHO cells expressing msFRP1 or msFRP5 alone are co-cultured with HEK293 Wnt reporter cells, no activity was detected (Table 1, row 5). In addition, when the conditioned media from CHO cells expressing msFRP1 or msFRP5 was added to HEK293 Wnt reporter cells, no activity was detected (Table 1, row 6), suggesting that sFRP1 or sFRP5 are not capable of enhancing Wnt signaling without co-expression of mWnt1. When the conditioned media of CHO mWnt1 and the conditioned media of CHO msFRP1 or msFRP5 were combined together before adding to the HEK293 Wnt reporter, no activity was detected (Table 1, row 7). When the conditioned media of CHO mWnt1 cells was added to CHO msFRP1 or msFRP5 expressing cells and cultured overnight prior to adding the conditioned media to HEK293 Wnt reporter cells, no activity was detected (Table 1, row 8). When CHO msFRP1 or msFRP5 conditioned media was added to CHO mWnt1 expressing cells overnight followed by adding this conditioned media to HEK293 Wnt reporter cells, reporter activity was detected (Table 1, row 9). When recombinant hsFRP1 or hsFRP5 protein was added to CHO mWnt1 expressing cells overnight, followed by adding this conditioned media to HEK293 Wnt reporter cells, activation of the Wnt reporter was observed (Table 1, row 11). Finally, if both mWnt1 and msFRP1 or msFRP5 were co-expressed in the same CHO cells, the conditioned media activated the HEK293 Wnt reporter (Table 1, row 10).

TABLE 1

| | Treatment | Reporter Activity |
|---|---|---|
| 1 | CHO cells (co-cultured with reporter cells) | − |
| 2 | CHO cell conditioned media (CM) | − |
| 3 | CHO mWnt1 cells | + |
| 4 | CHO mWnt1 cell CM | − |
| 5 | CHO mFRP1 or msFRP5 cells | − |
| 6 | CHO mFRP1 or msFRP5 cell CM | − |
| 7 | CHO mWnt1 CM + CHO sFRP1/5 CM | − |

TABLE 1-continued

Figure 3:
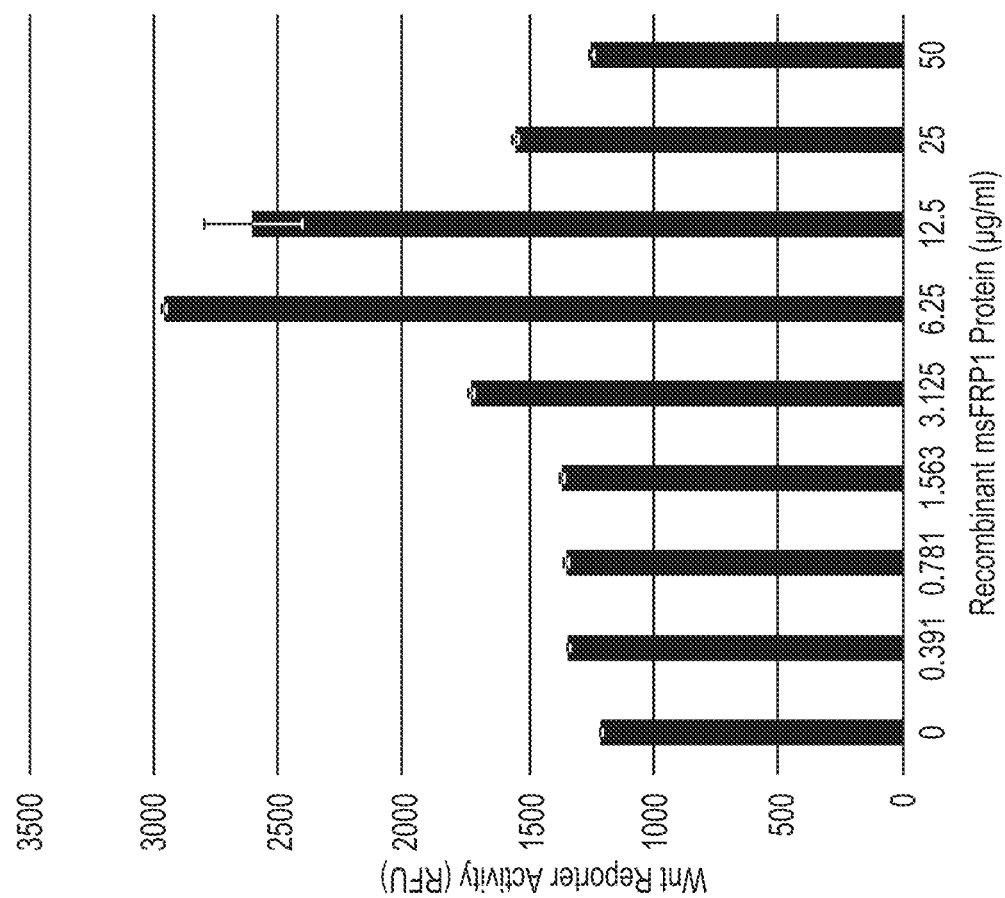
FIG. 3 shows mouse sFRP1 (msFRP1) both enhances and inhibits mouse Wnt1 (mWnt1) activity. Recombinant msFRP1 protein was added to CHO mWnt1-expressing cells for 24 hours prior to adding the conditioned media to HEK293 hFz4/hLRP5 Wnt reporter cells. sFRP1 protein showed a maximal enhancement of mWnt1 activity at 6.25 micrograms per milliliter (μg/mL) of protein added with doses of 25 μg/mL and 50 μg/mL resulting in reduction of the mWnt1 activity down to baseline levels.

| | Treatment | Reporter Activity |
|---|---|---|
| 8 | CHO mWnt1 CM + CHO sFRP1/5 Cell | − |
| 9 | CHO mWnt1 cell cultured with CHO sFRP1/5 CM overnight, then adding this CM to the Wnt reporter cells | + |
| 10 | CHO mWnt1/sFRP1/5 CM (Stable line expressing both mWnt1 and sFRP1 or sFRP5 in the same cell) | + |
| 11 | Adding sFRP1/5 protein to CHO mWnt1 expressing cells overnight and then adding this CM to Wnt reporter cells. | + | sFRPs have been observed to act both as positive and negative regulators of Wnt activity. Initially, several publications demonstrated sFRP inhibition of Wnt activity (Leyns et al. Cell 88:747-756 (1997); Wang et al. Cell 88:757-766 (1997)), but later studies showed that sFRPs can potentiate Wnt signaling at physiological doses of sFRPs (Mii et al. Development 136:4083-4088 (2009); Holly et al. Dev. Biol. 388:192-204 (2014)). To test for this biphasic activity of sFRPs, a dose series of recombinant sFRP1 protein were added to CHO mWnt1 expressing cells for 24 hours followed by removal of this conditioned media to treat HEK293 Wnt reporter cells. A bell-shaped curve was observed with relatively lower doses of sFRP resulting in enhancement of mWnt1 activity and higher concentrations of sFRP1 resulting in a return of Wnt signaling back to baseline levels (FIG. 3).

Figure 4F:
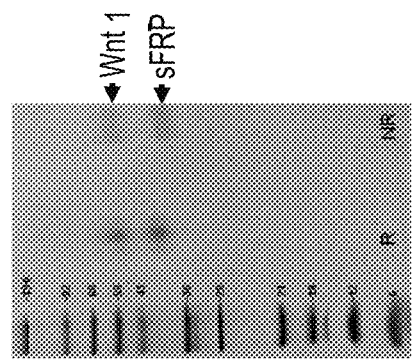
FIG. 4F. sFRP1/Wnt-1 complex purified from a gel filtration column was loaded onto a 15% SDS-PAGE gel and stained with Coomassie blue. Two bands, at 37 kDa and 52 kDa, were observed, with a roughly 1:1 molar ratio.
Figure 4D:
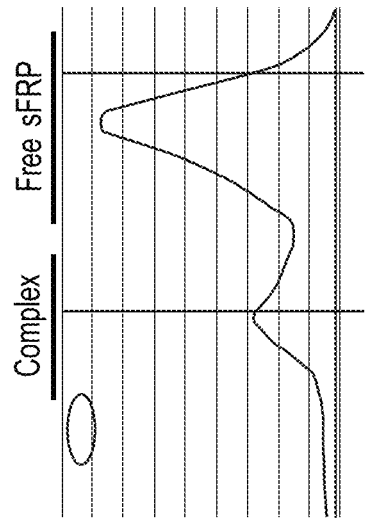
FIG. 4D. Pool from a SP Sepharose column was loaded and eluted from a gel filtration (Superdex 200) column. The earlier-eluted peak contained the sFRP1/Wnt-1 complex, while the later-eluted peak contained the free sFRP.
Figure 4E:
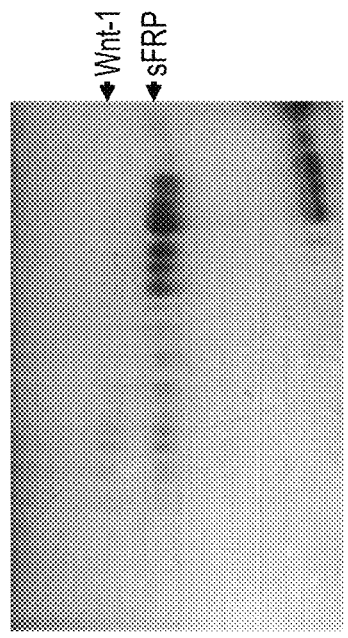
FIG. 4E. Fractions collected from gel filtration elution were loaded onto a 15% SDS-PAGE gel and stained with Coomassie blue. The lower band (37 kDa) represents sFRP1 and the upper band (52 kDa) represents Wnt-1.
Figure 4A:
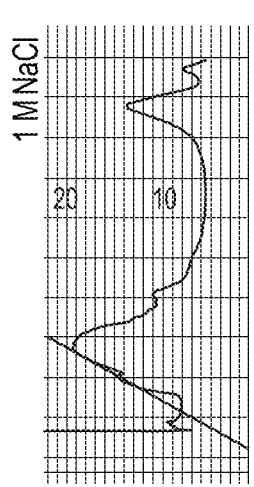
FIG. 4A. Conditioned media from CHO cells co-expressing msFRP1 and mWnt-1 were loaded onto SP Sepharose column, and bound proteins were eluted with a linear gradient of high salt buffer. The distinct late elution peak was the position that sFRP was usually eluted.
Figure 4B:
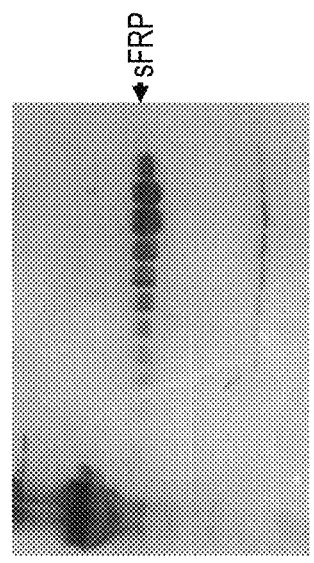
FIG. 4B. Fractions collected from SP elution were loaded onto 15 percent (%) SDS-PAGE and stained with silver. The 37 kDa bands represent sFRP1.
Figure 4C:
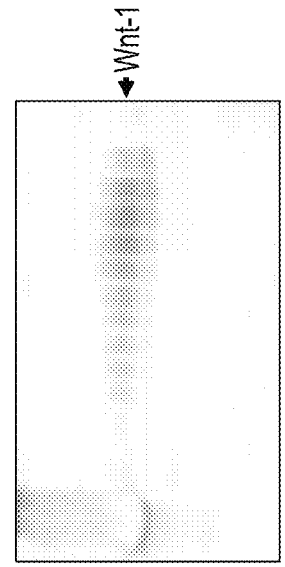
FIG. 4C. The same fractions of FIG. 4B were subjected to Western blot probed with antibody against mWnt-1. mWnt-1 was detected as a ~52 kDa band that is present in the same fractions where sFRP1 was detected.
Figure 5:
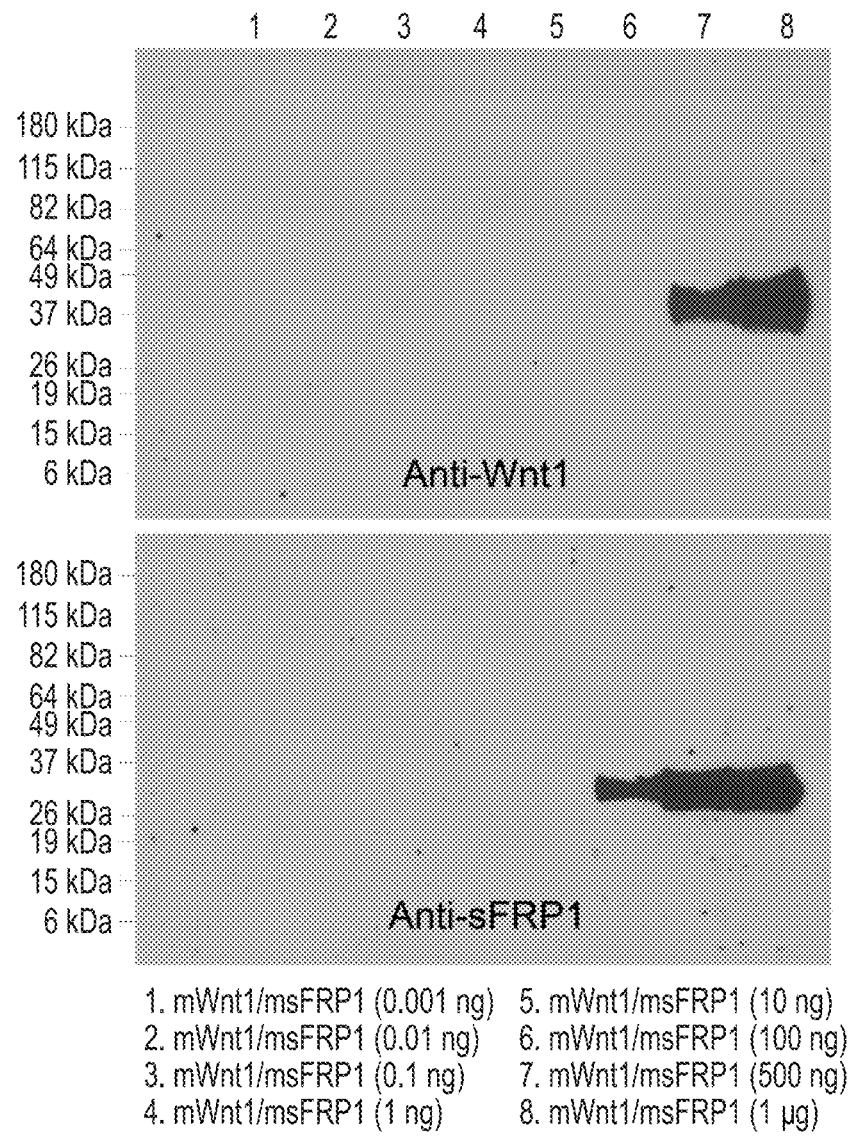
FIG. 5 shows both mWnt1 and msFRP1 Proteins were detected by Western Blot when the purified recombinant mWnt1/msFRP1 complex was run on an SDS-PAGE gel. 0.001 nanograms per milliliter (ng/mL) of mWnt1/msFRP1 (lane 1), 0.01 ng/mL of mWnt1/msFRP1 (lane 2), 0.1 ng/mL of mWnt1/msFRP1 (lane 3), 1 ng/mL of mWnt1/msFRP1 (lane 4), 10 ng/mL of mWnt1/msFRP1 (lane 5), 100 ng/mL of mWnt1/msFRP1 (lane 6), 500 ng/mL of mWnt1/msFRP1 (lane 7), and 1 microgram per milliliter (μg/mL) of mWnt1/msFRP1 (lane 8) were run on a 4-20% acrylamide gel under reducing conditions and then transferred to PVDF membrane. Western Blotting was performed with a goat anti-Wnt-1 antibody (1 μg/mL) and a goat anti-msFRP1 antibody (1 μg/mL). A secondary antibody (donkey anti-goat HRP antibody) was used at 1 μg/mL for detection.

CHO mWnt1/msFRP1 expressing cells were used to purify a mWnt1/msFRP1 protein complex. CHO mWnt1/msFRP1 expressing cells were transitioned from 5% FBS containing media to 2% FBS containing media so they could be grown in suspension. After 9 days in culture, the CHO mWnt1/msFRP1 conditioned media was isolated and the mWnt1/msFRP1 complex was purified by an ion exchange chromatography (FIG. 4 A-C) followed by gel filtration chromatography (FIG. 4 D-E). sFRP1 tightly binds to a cation exchanger SP sepharose column, and a NaCl concentration of greater than 1 molar (M) is required to elute the protein, while Wnt-1 is usually eluted with NaCl concentration less than 0.3 M. If sFRP and Wnt1 did not form a complex, sFRP1 and Wnt-1 should be eluted at different peaks. However, the Western blot probed with anti-Wnt-1 antibody (FIG. 4B) showed that Wnt-1 was co-eluted with sFRP1 (FIG. 4C) in a later peak from SP sepharose column (FIG. 4A), suggesting complex formation between sFRP1 and Wnt-1. sFRP1 was detected with Silver staining, but Wnt-1 was hardly visible, indicating a large amount of free sFRP1 was present. Because of the size difference between sFPR1/Wnt-1 complex and free sFRP, gel filtration chromatography successfully separated these two different populations. The sFRP1/Wnt-1 complex was eluted in the earlier peak, while the free sFRP1 was eluted in the later peak (FIG. 4D). Both sFRP1 and Wnt-1 were detected in the complex (earlier) peak with Coomassie blue staining on SDS-PAGE (FIG. 4E). The purified sFRP1/Wnt-1 complex was loaded onto SDS-PAGE and stained with Coomassie Blue. Two bands, at 37 kDa and 52 kDa, were observed, with roughly 1:1 molar ratio based on densitometry analysis (FIG. 4F). Characterization of the protein complex by Western blotting detected both mWnt1 and msFRP1 in the purified complex sample (FIG. 5). N-terminal sequencing of purified complex identified both mouse Wnt-1 and mouse sFRP-1 sequence without any other protein sequence detected. Binding of mWnt1 and msFRP1 in conditioned media suggests that mWnt1 and msFRP1 are likely associated in a complex when purified.

Figure 6A:
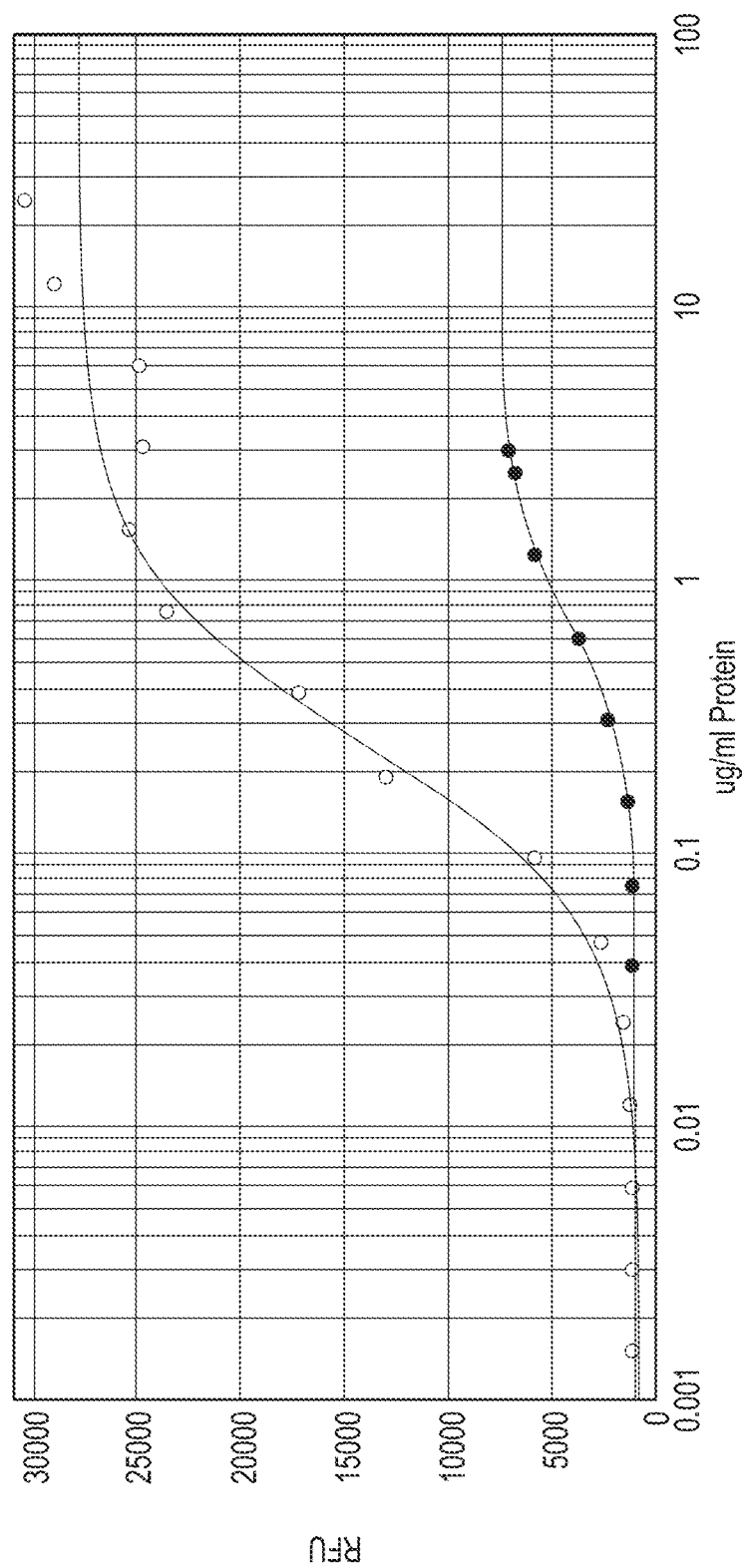
FIG. 6A, A mWnt1/msFRP1 protein complex was tested in HEK293 Wnt reporter cells expressing hFz4/Hlrp5 and shown to be more active compared to recombinant mouse Wnt10B protein.
Figure 6B:
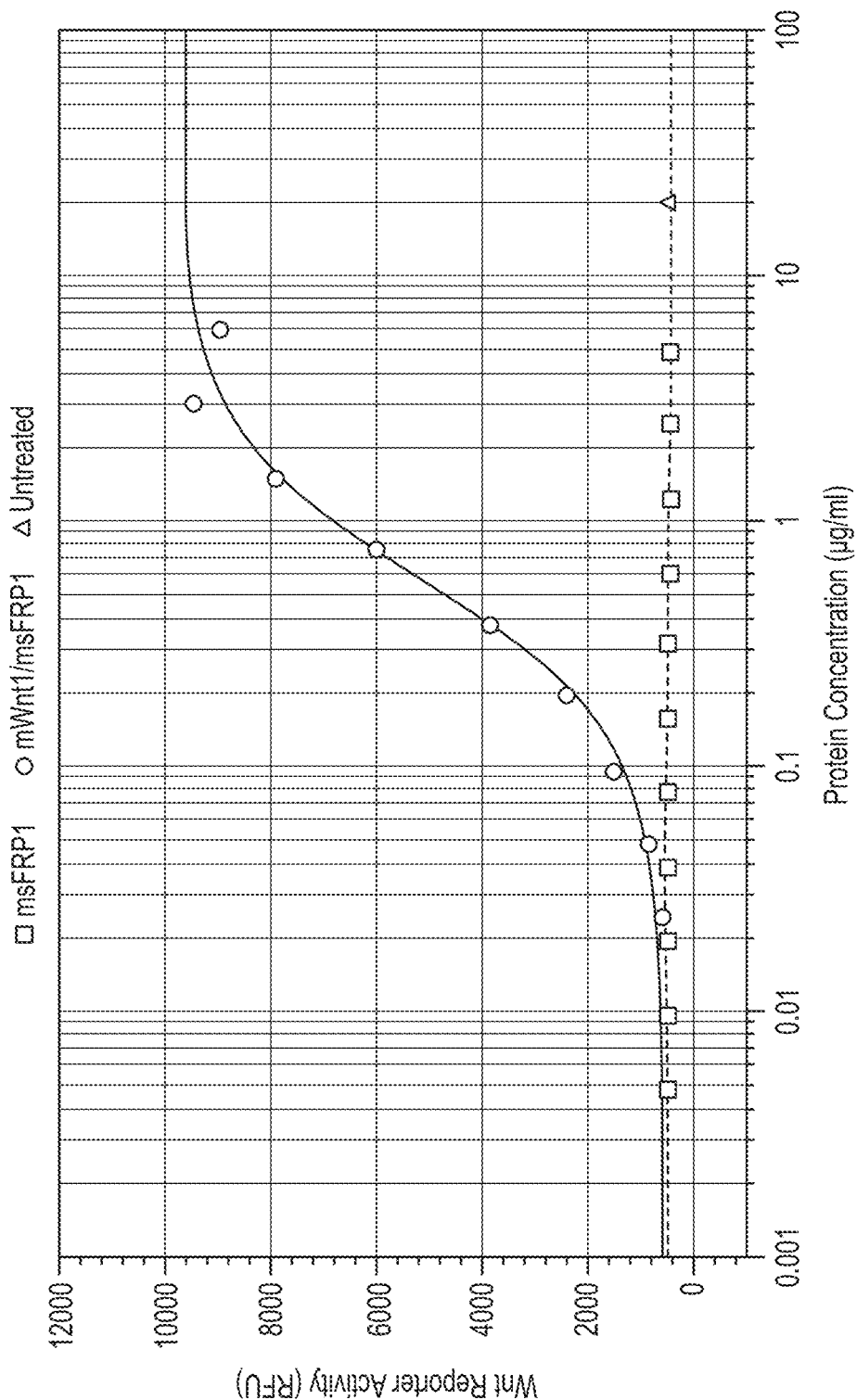
FIG. 6B. HEK293 Wnt Reporter cells expressing human Fz4 and human LRP5 were treated with either recombinant mouse sFRP1 protein (blue squares) or recombinant mouse Wnt1/sFRP1 (mWnt1/msFRP1) protein complex (red circles). The mWnt1/msFRP1 complex demonstrated clear induction of the HEK293 Wnt reporter cells in a dose responsive fashion, while the msFRP1 protein did not demonstrate activity alone.
Figure 6D:
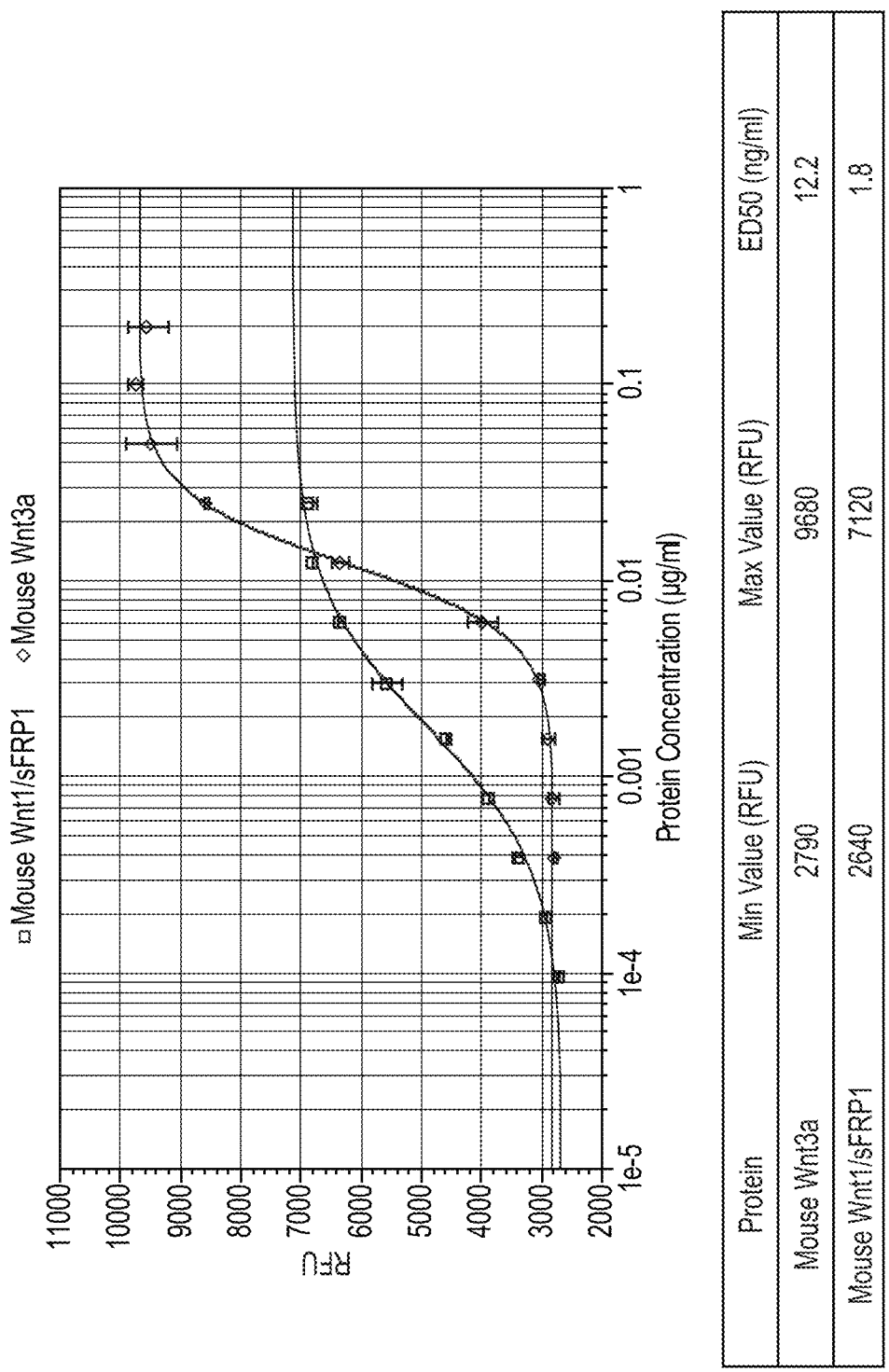
FIG. 6D. Mouse Wnt1/sFRP1 complexes, purified as described in FIG. 4, are highly potent and demonstrate better potency in HEK293 Wnt reporter assays compared to the most active Wnt (recombinant mouse Wnt3a) purified and stored in CHAPS buffer. The observed effective dose of 50 percent ($ED_{50}$) for mWnt1/msFRP1 was 1.8 ng/mL while the observed $ED_{50}$ for Recombinant mouse Wnt3a was 12.2 ng/mL.

The recombinant mWnt1/msFRP1 purified protein was tested for activity in a HEK293 Wnt reporter assay. Treatment of HEK293 Wnt reporter cells with recombinant msFRP1 protein did not result in activation of the Wnt reporter above untreated background levels (FIG. 6B). Treatment of HEK293 Wnt reporter cells with the mWnt1/msFRP1 protein complex did result in a robust activation of the Wnt reporter (FIG. 6A, FIG. 6B). As additional purification steps were added to the mWnt1/msFRP1 purification procedure (FIG. 4), a mWnt1/msFRP1 complex that was even more potent compared to the currently available most potent purified Wnt in CHAPS buffer (Wnt3a) was obtained (FIG. 6D).

These data demonstrate that sFRPs can increase the amount of active mWnt1 protein in conditioned media when sFRPs interact with CHO cells making mWnt1. To address whether sFRP-induced liberation of Wnt was specific for mWnt1 or whether could sFRPs could work in a similar fashion with other Wnt family members, additional sFRP co-culture experiments were performed with mWnt1, mWnt2b, and human Wnt6 (hWnt6).

Figure 7A:
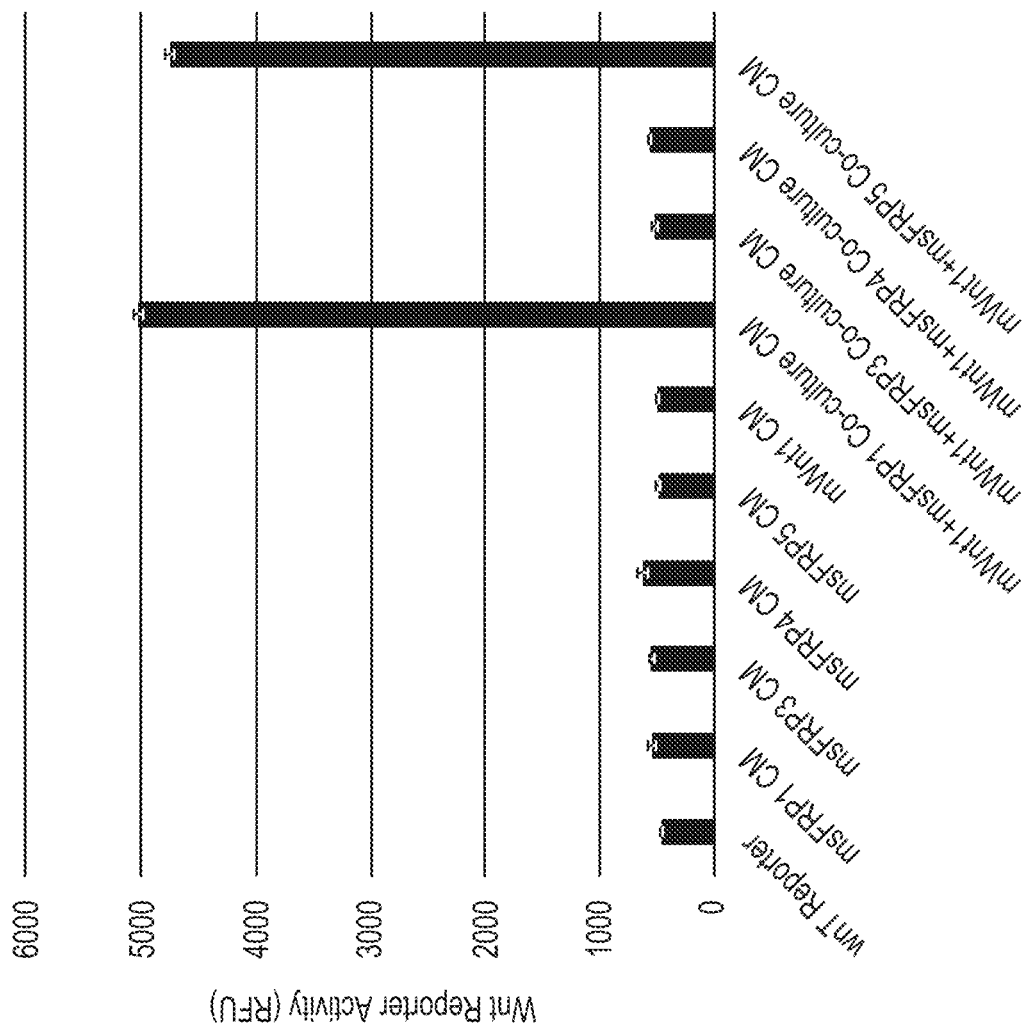
FIG. 7A. Conditioned media from cells expressing msFRP1, msFRP3, msFRP4, and msFRP5 was added to HEK293 Wnt reporter cells and did not induce Wnt reporter activity above HEK293 Wnt reporter activity alone. When cells expressing mWnt1 were cultured together with cells expressing msFRP1 and msFRP5 for 24 hours, this co-cultured conditioned media induced Wnt pathway activity when added to HEK293 Wnt reporter cells.
Figure 7B:
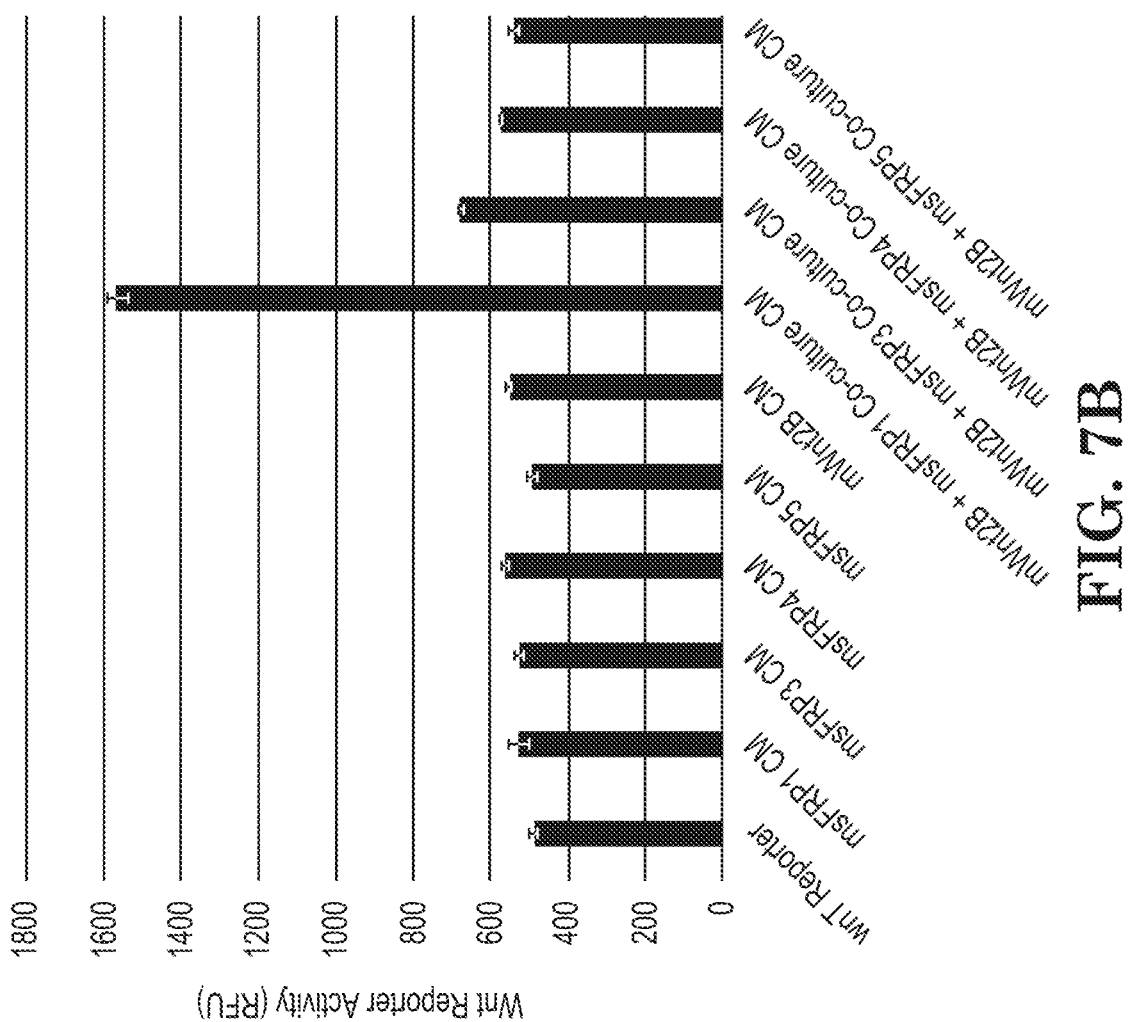
FIG. 7B. Similar experiments show that conditioned media from co-cultures of cells expressing mouse Wnt2b along with msFRP1 also resulted in Wnt pathway activation.
Figure 7C:
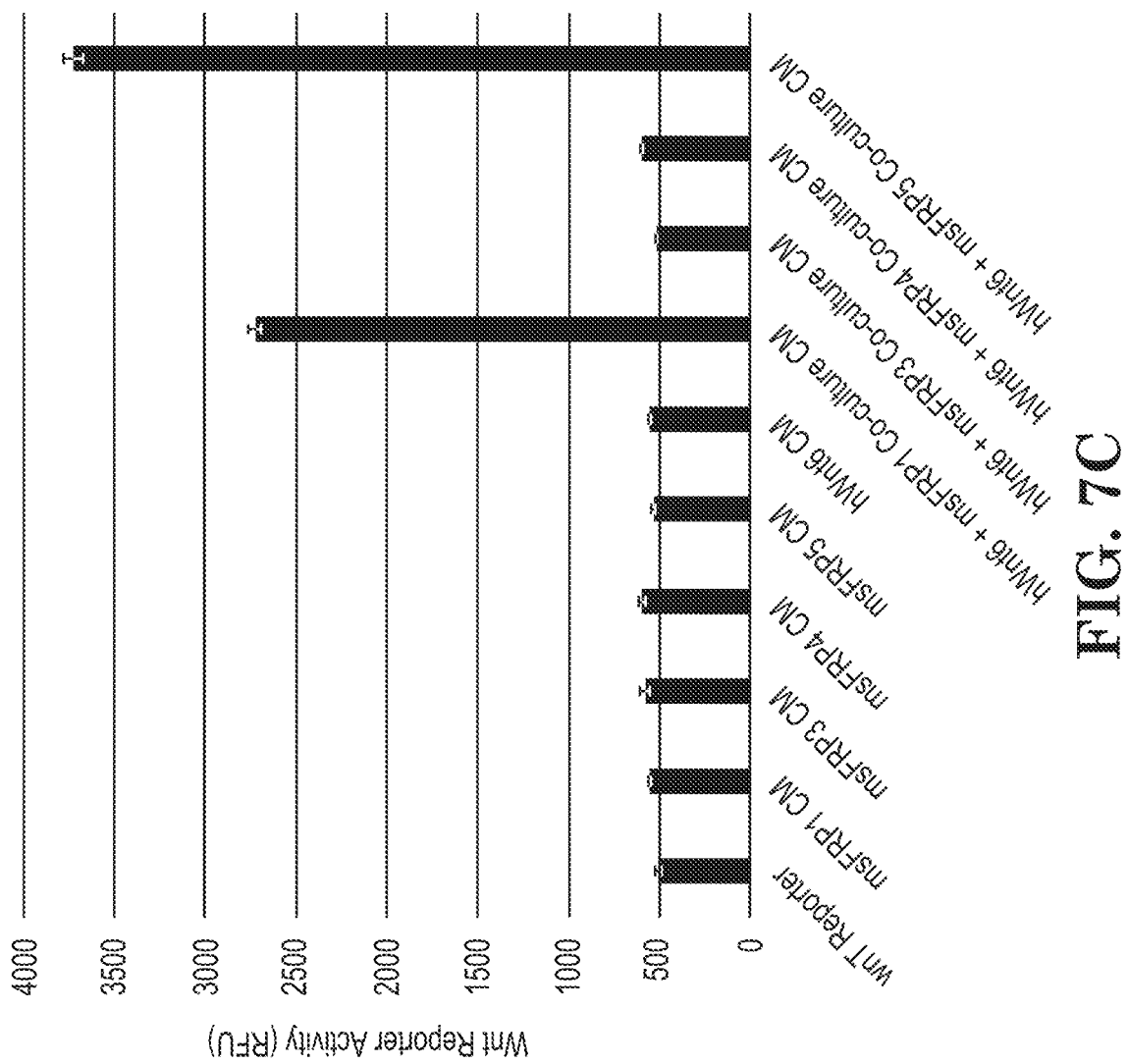
FIG. 7C. Conditioned media from human Wnt6 expressing cells co-cultured with msFRP1 or msFRP5 expressing cells also resulted in a significant increase in Wnt reporter activity.
Figure 8:
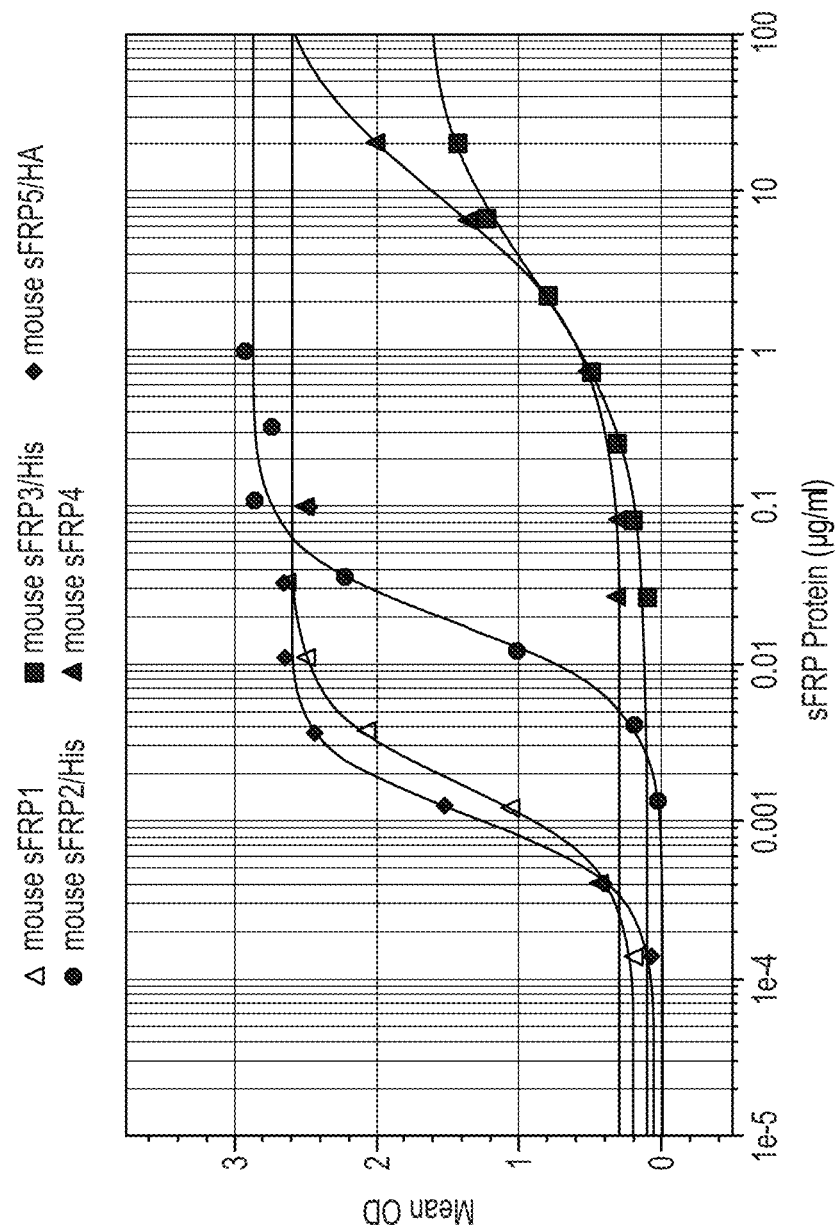
FIG. 8 shows that secreted Wnt proteins (e.g., Wnt3a) bind sFRP homologs, indicating that secreted Wnt proteins may, like tethered Wnts (e.g., Wnt1, Wnt2b and Wnt6), also be overexpressed with sFRP proteins and purified in an active state without (3-((3-cholamidopropyl) dimethylammonio)-1-propanesulfonate) (CHAPS). Purified recombinant mouse sFRP proteins were tested in ELISA binding assays with a biotinylated mouse Wnt3a protein. (Because different tags were used for the different sFRP proteins, the relative binding affinity cannot be compared using these data.) The msFRP1 and msFRP4 were detected with goat anti-sFRP1 and sheep anti-sFRP4 antibody, respectively. His tagged-mouse sFRP2 and His tagged-mouse sFRP3 were detected with a mouse anti-His antibody. HA tagged-mouse sFRP5 was detected with a mouse anti-HA antibody.

When CHO cells expressing msFRP1 were co-cultured with CHO cells expressing mWnt2b and the resulting conditioned media was added to HEK293 Wnt reporter cells, activation of the Wnt reporter was detected (FIG. 7B). Interestingly, co-cultures of CHO mWnt2b cells with CHO msFRP5 did not result in Wnt activity in the conditioned media (FIG. 7B) similar to the conditioned media from co-cultures of CHO mWnt1 and CHO msFRP5 cells (FIG. 7A). Conditioned media from HEK293 expressing hWnt6 co-cultured with CHO msFRP1 and msFRP5 activated HEK293 Wnt reporter cells (FIG. 7C) similar to what was seen with CHO mWnt1 co-culture experiments with CHO sFRP1 and sFRP5 (FIG. 7A). These data demonstrate that sFRPs can enhance the liberation of not only mWnt1 from the cell surface of mWnt1 expressing cells, but sFRPs can also liberate mWnt2b and hWnt6 from the cell surface of cells expressing mWnt2b or hWnt6. These data also suggest that sFRPs can be used to free many, if not all, Wnt proteins bound to the cell membrane to facilitate the purification active Wnt/sFRP complexes.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An isolated protein complex comprising a Wnt and a sFRP, wherein the protein complex exhibits an effective dose of 50 percent ($ED_{50}$) of less than 500 ng/mL, as measured using a HEK293 TCF9-secreted alkaline phosphatase (SEAP) hFz4/hLRP5 Wnt Reporter assay.

2. The isolated protein complex of claim 1, wherein the Wnt comprises Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, or Wnt16, or a combination thereof.

3. The isolated protein complex of claim 1, wherein the sFRP comprises sFRP1, sFRP2, sFRP3, sFRP4, or sFRP5, or a combination thereof.

4. The isolated protein complex of claim 1, wherein the protein complex is substantially free of a detergent.

5. The isolated protein complex of claim 1, wherein the Wnt comprises a mouse Wnt and the sFRP comprises a mouse sFRP.

6. The isolated protein complex of claim 1, wherein the Wnt comprises a mouse Wnt1 and the sFRP comprises a mouse sFRP1.

7. A composition comprising a Wnt and a sFRP, wherein the Wnt comprises active Wnt, and wherein the composition is substantially free of a detergent.

8. The composition of claim 7, wherein the Wnt comprises Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, or Wnt16, or a combination thereof.

9. The composition of claim 7, wherein the active Wnt comprises Wnt having Wnt Reporter activity as measured using a secreted alkaline phosphatase (SEAP) Reporter assay.

10. The composition of claim 7, wherein the sFRP comprises sFRP1, sFRP2, sFRP3, sFRP4, or sFRP5, or a combination thereof.

11. The composition of claim 7, wherein the Wnt comprises a mouse Wnt and the sFRP comprises a mouse sFRP.

12. The composition of claim 7, wherein the Wnt comprises a mouse Wnt1 and the sFRP comprises a mouse sFRP1.

13. The composition of claim 7, wherein the Wnt exhibits an effective dose of 50 percent ($ED_{50}$) of less than 100 ng/mL, as measured using a HEK293 TCF9-SEAP hFz4/hLRP5 Wnt Reporter assay.

14. The composition of claim 7, the composition further comprising R-Spondin 1, R-Spondin 2, R-Spondin 3, R-Spondin 4, Lipocalin7, or WIF1, or a combination thereof.

15. A method comprising:
overexpressing a Wnt1 and an sFRP1;
forming a complex comprising the Wnt1 and the sFRP1, wherein the Wnt comprises an active Wnt; and
isolating the active Wnt1, wherein isolating the active Wnt1 comprises an aqueous purification procedure, and wherein isolating the Wnt does not comprise using a detergent.

* * * * *

SEQUENCE LISTING

<160> NUMBER OF SEQ ID NOS: 9

<210> SEQ ID NO 1
<211> LENGTH: 4
<212> TYPE: PRT
<213> ORGANISM: artificial
<220> FEATURE:
<223> OTHER INFORMATION: peptide linker

<400> SEQUENCE: 1

Gly Gly Gly Ser
1

<210> SEQ ID NO 2
<211> LENGTH: 5
<212> TYPE: PRT
<213> ORGANISM: artificial
<220> FEATURE:
<223> OTHER INFORMATION: peptide linker

<400> SEQUENCE: 2

Gly Gly Gly Gly Ser
1               5

<210> SEQ ID NO 3
<211> LENGTH: 5
<212> TYPE: PRT
<213> ORGANISM: artificial
<220> FEATURE:
<223> OTHER INFORMATION: peptide linker

<400> SEQUENCE: 3

Gly Ser Gly Ser Gly
1               5

<210> SEQ ID NO 4
<211> LENGTH: 5
<212> TYPE: PRT
<213> ORGANISM: artificial
<220> FEATURE:
<223> OTHER INFORMATION: peptide linker

<400> SEQUENCE: 4

Gly Gly Gly Gly Gly
1               5

<210> SEQ ID NO 5
<211> LENGTH: 10
<212> TYPE: PRT
<213> ORGANISM: artificial
<220> FEATURE:
<223> OTHER INFORMATION: peptide linker

<400> SEQUENCE: 5

Gly Ser Gly Ser Gly Gly Ser Gly Ser Gly
1               5                   10

<210> SEQ ID NO 6
<211> LENGTH: 1600
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (5)..(1600)
<223> OTHER INFORMATION: these nucleotides may be absent -continued

<400> SEQUENCE: 6

```
Gly Gly Gly Ser Gly Gly Gly Ser Gly Gly Gly Ser Gly Gly Gly Ser
1               5                   10                  15
Gly Gly Gly Ser Gly Gly Gly Ser Gly Gly Gly Ser Gly Gly Gly Ser
            20                  25                  30
Gly Gly Gly Ser Gly Gly Gly Ser Gly Gly Gly Ser Gly Gly Gly Ser
        35                  40                  45
Gly Gly Gly Ser Gly Gly Gly Ser Gly Gly Gly Ser Gly Gly Gly Ser
    50                  55                  60
Gly Gly Gly Ser Gly Gly Gly Ser Gly Gly Gly Ser Gly Gly Gly Ser
65                  70                  75                  80
Gly Gly Gly Ser Gly Gly Gly Ser Gly Gly Gly Ser Gly Gly Gly Ser
            85                  90                  95
Gly Gly Gly Ser Gly Gly Gly Ser Gly Gly Gly Ser Gly Gly Gly Ser
        100                 105                 110
Gly Gly Gly Ser Gly Gly Gly Ser Gly Gly Gly Ser Gly Gly Gly Ser
    115                 120                 125
Gly Gly Gly Ser Gly Gly Gly Ser Gly Gly Gly Ser Gly Gly Gly Ser
130                 135                 140
Gly Gly Gly Ser Gly Gly Gly Ser Gly Gly Gly Ser Gly Gly Gly Ser
145                 150                 155                 160
Gly Gly Gly Ser Gly Gly Gly Ser Gly Gly Gly Ser Gly Gly Gly Ser
            165                 170                 175
Gly Gly Gly Ser Gly Gly Gly Ser Gly Gly Gly Ser Gly Gly Gly Ser
        180                 185                 190
Gly Gly Gly Ser Gly Gly Gly Ser Gly Gly Gly Ser Gly Gly Gly Ser
    195                 200                 205
Gly Gly Gly Ser Gly Gly Gly Ser Gly Gly Gly Ser Gly Gly Gly Ser
210                 215                 220
Gly Gly Gly Ser Gly Gly Gly Ser Gly Gly Gly Ser Gly Gly Gly Ser
225                 230                 235                 240
Gly Gly Gly Ser Gly Gly Gly Ser Gly Gly Gly Ser Gly Gly Gly Ser
            245                 250                 255
Gly Gly Gly Ser Gly Gly Gly Ser Gly Gly Gly Ser Gly Gly Gly Ser
        260                 265                 270
Gly Gly Gly Ser Gly Gly Gly Ser Gly Gly Gly Ser Gly Gly Gly Ser
    275                 280                 285
Gly Gly Gly Ser Gly Gly Gly Ser Gly Gly Gly Ser Gly Gly Gly Ser
290                 295                 300
Gly Gly Gly Ser Gly Gly Gly Ser Gly Gly Gly Ser Gly Gly Gly Ser
305                 310                 315                 320
Gly Gly Gly Ser Gly Gly Gly Ser Gly Gly Gly Ser Gly Gly Gly Ser
            325                 330                 335
Gly Gly Gly Ser Gly Gly Gly Ser Gly Gly Gly Ser Gly Gly Gly Ser
        340                 345                 350
Gly Gly Gly Ser Gly Gly Gly Ser Gly Gly Gly Ser Gly Gly Gly Ser
    355                 360                 365
Gly Gly Gly Ser Gly Gly Gly Ser Gly Gly Gly Ser Gly Gly Gly Ser
370                 375                 380
Gly Gly Gly Ser Gly Gly Gly Ser Gly Gly Gly Ser Gly Gly Gly Ser
385                 390                 395                 400
Gly Gly Gly Ser Gly Gly Gly Ser Gly Gly Gly Ser Gly Gly Gly Ser
            405                 410                 415
```

Gly Gly Gly Ser Gly Gly Gly Ser Gly Gly Gly Ser Gly Gly Gly Ser
            420                 425                 430

Gly Gly Gly Ser Gly Gly Gly Ser Gly Gly Gly Ser Gly Gly Gly Ser
            435                 440                 445

Gly Gly Gly Ser Gly Gly Gly Ser Gly Gly Gly Ser Gly Gly Gly Ser
            450                 455                 460

Gly Gly Gly Ser Gly Gly Gly Ser Gly Gly Gly Ser Gly Gly Gly Ser
465                 470                 475                 480

Gly Gly Gly Ser Gly Gly Gly Ser Gly Gly Gly Ser Gly Gly Gly Ser
            485                 490                 495

Gly Gly Gly Ser Gly Gly Gly Ser Gly Gly Gly Ser Gly Gly Gly Ser
            500                 505                 510

Gly Gly Gly Ser Gly Gly Gly Ser Gly Gly Gly Ser Gly Gly Gly Ser
            515                 520                 525

Gly Gly Gly Ser Gly Gly Gly Ser Gly Gly Gly Ser Gly Gly Gly Ser
            530                 535                 540

Gly Gly Gly Ser Gly Gly Gly Ser Gly Gly Gly Ser Gly Gly Gly Ser
545                 550                 555                 560

Gly Gly Gly Ser Gly Gly Gly Ser Gly Gly Gly Ser Gly Gly Gly Ser
            565                 570                 575

Gly Gly Gly Ser Gly Gly Gly Ser Gly Gly Gly Ser Gly Gly Gly Ser
            580                 585                 590

Gly Gly Gly Ser Gly Gly Gly Ser Gly Gly Gly Ser Gly Gly Gly Ser
            595                 600                 605

Gly Gly Gly Ser Gly Gly Gly Ser Gly Gly Gly Ser Gly Gly Gly Ser
            610                 615                 620

Gly Gly Gly Ser Gly Gly Gly Ser Gly Gly Gly Ser Gly Gly Gly Ser
625                 630                 635                 640

Gly Gly Gly Ser Gly Gly Gly Ser Gly Gly Gly Ser Gly Gly Gly Ser
            645                 650                 655

Gly Gly Gly Ser Gly Gly Gly Ser Gly Gly Gly Ser Gly Gly Gly Ser
            660                 665                 670

Gly Gly Gly Ser Gly Gly Gly Ser Gly Gly Gly Ser Gly Gly Gly Ser
            675                 680                 685

Gly Gly Gly Ser Gly Gly Gly Ser Gly Gly Gly Ser Gly Gly Gly Ser
            690                 695                 700

Gly Gly Gly Ser Gly Gly Gly Ser Gly Gly Gly Ser Gly Gly Gly Ser
705                 710                 715                 720

Gly Gly Gly Ser Gly Gly Gly Ser Gly Gly Gly Ser Gly Gly Gly Ser
            725                 730                 735

Gly Gly Gly Ser Gly Gly Gly Ser Gly Gly Gly Ser Gly Gly Gly Ser
            740                 745                 750

Gly Gly Gly Ser Gly Gly Gly Ser Gly Gly Gly Ser Gly Gly Gly Ser
            755                 760                 765

Gly Gly Gly Ser Gly Gly Gly Ser Gly Gly Gly Ser Gly Gly Gly Ser
            770                 775                 780

Gly Gly Gly Ser Gly Gly Gly Ser Gly Gly Gly Ser Gly Gly Gly Ser
785                 790                 795                 800

Gly Gly Gly Ser Gly Gly Gly Ser Gly Gly Gly Ser Gly Gly Gly Ser
            805                 810                 815

Gly Gly Gly Ser Gly Gly Gly Ser Gly Gly Gly Ser Gly Gly Gly Ser
            820                 825                 830

-continued

Gly Gly Gly Ser Gly Gly Gly Ser Gly Gly Gly Ser
        835             840             845

Gly Gly Gly Ser Gly Gly Gly Ser Gly Gly Gly Ser
850             855             860

Gly Gly Gly Ser Gly Gly Gly Ser Gly Gly Gly Ser
865             870             875             880

Gly Gly Gly Ser Gly Gly Gly Ser Gly Gly Gly Ser
        885             890             895

Gly Gly Gly Ser Gly Gly Gly Ser Gly Gly Gly Ser
        900             905             910

Gly Gly Gly Ser Gly Gly Gly Ser Gly Gly Gly Ser
        915             920             925

Gly Gly Gly Ser Gly Gly Gly Ser Gly Gly Gly Ser
        930             935             940

Gly Gly Gly Ser Gly Gly Gly Ser Gly Gly Gly Ser
945             950             955             960

Gly Gly Gly Ser Gly Gly Gly Ser Gly Gly Gly Ser
        965             970             975

Gly Gly Gly Ser Gly Gly Gly Ser Gly Gly Gly Ser
        980             985             990

Gly Gly Gly Ser Gly Gly Gly Ser  Gly Gly Gly Ser Gly  Gly Gly Ser
        995             1000             1005

Gly Gly  Gly Ser Gly Gly Gly  Ser Gly Gly Gly Ser  Gly Gly Gly
    1010             1015             1020

Ser Gly  Gly Gly Ser Gly Gly  Gly Ser Gly Gly Gly  Ser Gly Gly
    1025             1030             1035

Gly Ser  Gly Gly Gly Ser Gly  Gly Gly Ser Gly Gly  Gly Ser Gly
    1040             1045             1050

Gly Gly  Ser Gly Gly Gly Ser  Gly Gly Gly Ser Gly  Gly Gly Ser
    1055             1060             1065

Gly Gly  Gly Ser Gly Gly Gly  Ser Gly Gly Gly Ser  Gly Gly Gly
    1070             1075             1080

Ser Gly  Gly Gly Ser Gly Gly  Gly Ser Gly Gly Gly  Ser Gly Gly
    1085             1090             1095

Gly Ser  Gly Gly Gly Ser Gly  Gly Gly Ser Gly Gly  Gly Ser Gly
    1100             1105             1110

Gly Gly  Ser Gly Gly Gly Ser  Gly Gly Gly Ser Gly  Gly Gly Ser
    1115             1120             1125

Gly Gly  Gly Ser Gly Gly Gly  Ser Gly Gly Gly Ser  Gly Gly Gly
    1130             1135             1140

Ser Gly  Gly Gly Ser Gly Gly  Gly Ser Gly Gly Gly  Ser Gly Gly
    1145             1150             1155

Gly Ser  Gly Gly Gly Ser Gly  Gly Gly Ser Gly Gly  Gly Ser Gly
    1160             1165             1170

Gly Gly  Ser Gly Gly Gly Ser  Gly Gly Gly Ser Gly  Gly Gly Ser
    1175             1180             1185

Gly Gly  Gly Ser Gly Gly Gly  Ser Gly Gly Gly Ser  Gly Gly Gly
    1190             1195             1200

Ser Gly  Gly Gly Ser Gly Gly  Gly Ser Gly Gly Gly  Ser Gly Gly
    1205             1210             1215

Gly Ser  Gly Gly Gly Ser Gly  Gly Gly Ser Gly Gly  Gly Ser Gly
    1220             1225             1230

Gly Gly  Ser Gly Gly Gly Ser  Gly Gly Gly Ser Gly  Gly Gly Ser

Gly Gly Gly Ser Gly Gly Gly   Ser Gly Gly Ser   Gly Gly Gly
            1250                1255               1260

Ser Gly Gly Gly Ser Gly Gly   Gly Ser Gly Gly   Ser Gly Gly
            1265                1270               1275

Gly Ser Gly Gly Gly Ser Gly   Gly Gly Ser Gly   Gly Gly Ser Gly
            1280                1285               1290

Gly Gly Ser Gly Gly Gly Ser   Gly Gly Gly Ser   Gly Gly Gly Ser
            1295                1300               1305

Gly Gly Gly Ser Gly Gly Gly   Ser Gly Gly Gly   Ser Gly Gly Gly
            1310                1315               1320

Ser Gly Gly Gly Ser Gly Gly   Gly Ser Gly Gly   Gly Ser Gly Gly
            1325                1330               1335

Gly Ser Gly Gly Gly Ser Gly   Gly Gly Ser Gly   Gly Gly Ser Gly
            1340                1345               1350

Gly Gly Ser Gly Gly Gly Ser   Gly Gly Gly Ser   Gly Gly Gly Ser
            1355                1360               1365

Gly Gly Gly Ser Gly Gly Gly   Ser Gly Gly Gly   Ser Gly Gly Gly
            1370                1375               1380

Ser Gly Gly Gly Ser Gly Gly   Gly Ser Gly Gly   Gly Ser Gly Gly
            1385                1390               1395

Gly Ser Gly Gly Gly Ser Gly   Gly Gly Ser Gly   Gly Gly Ser Gly
            1400                1405               1410

Gly Gly Ser Gly Gly Gly Ser   Gly Gly Gly Ser   Gly Gly Gly Ser
            1415                1420               1425

Gly Gly Gly Ser Gly Gly Gly   Ser Gly Gly Gly   Ser Gly Gly Gly
            1430                1435               1440

Ser Gly Gly Gly Ser Gly Gly   Gly Ser Gly Gly   Gly Ser Gly Gly
            1445                1450               1455

Gly Ser Gly Gly Gly Ser Gly   Gly Gly Ser Gly   Gly Gly Ser Gly
            1460                1465               1470

Gly Gly Ser Gly Gly Gly Ser   Gly Gly Gly Ser   Gly Gly Gly Ser
            1475                1480               1485

Gly Gly Gly Ser Gly Gly Gly   Ser Gly Gly Gly   Ser Gly Gly Gly
            1490                1495               1500

Ser Gly Gly Gly Ser Gly Gly   Gly Ser Gly Gly   Gly Ser Gly Gly
            1505                1510               1515

Gly Ser Gly Gly Gly Ser Gly   Gly Gly Ser Gly   Gly Gly Ser Gly
            1520                1525               1530

Gly Gly Ser Gly Gly Gly Ser   Gly Gly Gly Ser   Gly Gly Gly Ser
            1535                1540               1545

Gly Gly Gly Ser Gly Gly Gly   Ser Gly Gly Gly   Ser Gly Gly Gly
            1550                1555               1560

Ser Gly Gly Gly Ser Gly Gly   Gly Ser Gly Gly   Gly Ser Gly Gly
            1565                1570               1575

Gly Ser Gly Gly Gly Ser Gly   Gly Gly Ser Gly   Gly Gly Ser Gly
            1580                1585               1590

Gly Gly Ser Gly Gly Gly Ser
            1595                1600

<210> SEQ ID NO 7
<211> LENGTH: 2000
<212> TYPE: PRT
<213> ORGANISM: artificial

<220> FEATURE:
<223> OTHER INFORMATION: peptide linker
<220> FEATURE:
<221> NAME/KEY: MISC_FEATURE
<222> LOCATION: (6)..(2000)
<223> OTHER INFORMATION: these nucleotides may be absent

<400> SEQUENCE: 7

```
Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser Gly Gly Gly Gly Ser Gly Gly Gly Gly Ser Gly Gly Gly Gly
        50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser Gly Gly Gly Gly Ser Gly Gly Gly Gly Ser Gly Gly
                100                 105                 110

Gly Gly Ser Gly Gly Gly Gly Ser Gly Gly Gly Gly Ser Gly Gly Gly
            115                 120                 125

Gly Ser Gly Gly Gly Gly Ser Gly Gly Gly Gly Ser Gly Gly Gly Gly
        130                 135                 140

Ser Gly Gly Gly Gly Ser Gly Gly Gly Gly Ser Gly Gly Gly Gly Ser
145                 150                 155                 160

Gly Gly Gly Gly Ser Gly Gly Gly Gly Ser Gly Gly Gly Gly Ser Gly
                165                 170                 175

Gly Gly Gly Ser Gly Gly Gly Gly Ser Gly Gly Gly Gly Ser Gly Gly
                180                 185                 190

Gly Gly Ser Gly Gly Gly Gly Ser Gly Gly Gly Gly Ser Gly Gly Gly
            195                 200                 205

Gly Ser Gly Gly Gly Gly Ser Gly Gly Gly Gly Ser Gly Gly Gly Gly
        210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gly Gly Ser Gly Gly Gly Gly Ser Gly
                245                 250                 255

Gly Gly Gly Ser Gly Gly Gly Gly Ser Gly Gly Gly Gly Ser Gly Gly
                260                 265                 270

Gly Gly Ser Gly Gly Gly Gly Ser Gly Gly Gly Gly Ser Gly Gly Gly
            275                 280                 285

Gly Ser Gly Gly Gly Gly Ser Gly Gly Gly Gly Ser Gly Gly Gly Gly
        290                 295                 300

Ser Gly Gly Gly Gly Ser Gly Gly Gly Gly Ser Gly Gly Gly Gly Ser
305                 310                 315                 320

Gly Gly Gly Gly Ser Gly Gly Gly Gly Ser Gly Gly Gly Gly Ser Gly
                325                 330                 335

Gly Gly Gly Ser Gly Gly Gly Gly Ser Gly Gly Gly Gly Ser Gly Gly
                340                 345                 350

Gly Gly Ser Gly Gly Gly Gly Ser Gly Gly Gly Gly Ser Gly Gly Gly
            355                 360                 365

Gly Ser Gly Gly Gly Gly Ser Gly Gly Gly Gly Ser Gly Gly Gly Gly
```

-continued

```
            370                 375                 380
Ser Gly Gly Gly Gly Ser Gly Gly Gly Ser Gly Gly Gly Ser
385                 390                 395                 400

Gly Gly Gly Gly Ser Gly Gly Gly Ser Gly Gly Gly Ser Gly
                405                 410                 415

Gly Gly Gly Ser Gly Gly Gly Gly Ser Gly Gly Gly Ser Gly
            420                 425                 430

Gly Gly Ser Gly Gly Gly Gly Ser Gly Gly Gly Ser Gly Gly
        435                 440                 445

Gly Ser Gly Gly Gly Gly Ser Gly Gly Gly Ser Gly Gly Gly
    450                 455                 460

Ser Gly Gly Gly Gly Ser Gly Gly Gly Ser Gly Gly Gly Ser
465                 470                 475                 480

Gly Gly Gly Gly Ser Gly Gly Gly Ser Gly Gly Gly Ser Gly
                485                 490                 495

Gly Gly Gly Ser Gly Gly Gly Ser Gly Gly Gly Ser Gly Gly
            500                 505                 510

Gly Gly Ser Gly Gly Gly Ser Gly Gly Gly Ser Gly Gly Gly
        515                 520                 525

Gly Ser Gly Gly Gly Ser Gly Gly Gly Ser Gly Gly Gly Gly
    530                 535                 540

Ser Gly Gly Gly Ser Gly Gly Gly Ser Gly Gly Gly Gly Ser
545                 550                 555                 560

Gly Gly Gly Ser Gly Gly Gly Ser Gly Gly Gly Gly Ser Gly
                565                 570                 575

Gly Gly Ser Gly Gly Gly Ser Gly Gly Gly Gly Ser Gly Gly
            580                 585                 590

Gly Gly Ser Gly Gly Gly Ser Gly Gly Gly Gly Ser Gly Gly
        595                 600                 605

Gly Ser Gly Gly Gly Ser Gly Gly Gly Gly Ser Gly Gly Gly
    610                 615                 620

Ser Gly Gly Gly Gly Ser Gly Gly Gly Ser Gly Gly Gly Ser
625                 630                 635                 640

Gly Gly Gly Gly Ser Gly Gly Gly Ser Gly Gly Gly Ser Gly
                645                 650                 655

Gly Gly Gly Ser Gly Gly Gly Ser Gly Gly Gly Ser Gly Gly
            660                 665                 670

Gly Gly Ser Gly Gly Gly Gly Ser Gly Gly Gly Ser Gly Gly
        675                 680                 685

Gly Ser Gly Gly Gly Gly Ser Gly Gly Gly Ser Gly Gly Gly
    690                 695                 700

Ser Gly Gly Gly Gly Ser Gly Gly Gly Ser Gly Gly Gly Ser
705                 710                 715                 720

Gly Gly Gly Gly Ser Gly Gly Gly Ser Gly Gly Gly Ser Gly
                725                 730                 735

Gly Gly Gly Ser Gly Gly Gly Ser Gly Gly Gly Ser Gly Gly
            740                 745                 750

Gly Gly Ser Gly Gly Gly Ser Gly Gly Gly Ser Gly Gly Gly
        755                 760                 765

Gly Ser Gly Gly Gly Ser Gly Gly Gly Ser Gly Gly Gly Gly
    770                 775                 780

Ser Gly Gly Gly Gly Ser Gly Gly Gly Ser Gly Gly Gly Ser
785                 790                 795                 800
```

-continued

Gly Gly Gly Gly Ser Gly Gly Gly Ser Gly Gly Gly Ser Gly
              805                 810                 815

Gly Gly Gly Ser Gly Gly Gly Gly Ser Gly Gly Gly Ser Gly Gly
              820                 825                 830

Gly Gly Ser Gly Gly Gly Gly Ser Gly Gly Gly Gly Ser Gly Gly Gly
          835                 840                 845

Gly Ser Gly Gly Gly Gly Ser Gly Gly Gly Ser Gly Gly Gly Gly
      850                 855                 860

Ser Gly Gly Gly Gly Ser Gly Gly Gly Gly Ser Gly Gly Gly Ser
865                 870                 875                 880

Gly Gly Gly Gly Ser Gly Gly Gly Gly Ser Gly Gly Gly Ser Gly
              885                 890                 895

Gly Gly Gly Ser Gly Gly Gly Gly Ser Gly Gly Gly Ser Gly Gly
              900                 905                 910

Gly Gly Ser Gly Gly Gly Gly Ser Gly Gly Gly Ser Gly Gly Gly
          915                 920                 925

Gly Ser Gly Gly Gly Gly Ser Gly Gly Gly Ser Gly Gly Gly Gly
      930                 935                 940

Ser Gly Gly Gly Gly Ser Gly Gly Gly Ser Gly Gly Gly Gly Ser
945                 950                 955                 960

Gly Gly Gly Gly Ser Gly Gly Gly Ser Gly Gly Gly Gly Ser Gly
              965                 970                 975

Gly Gly Ser Gly Gly Gly Gly Ser Gly Gly Gly Ser Gly Gly Gly
          980                 985                 990

Gly Gly Ser Gly Gly Gly Gly Ser  Gly Gly Gly Gly Ser  Gly Gly Gly
          995                 1000                1005

Gly Ser  Gly Gly Gly Gly Ser  Gly Gly Gly Gly Ser  Gly Gly Gly
    1010                1015                1020

Gly Ser  Gly Gly Gly Gly Ser  Gly Gly Gly Gly Ser  Gly Gly Gly
    1025                1030                1035

Gly Ser  Gly Gly Gly Gly Ser  Gly Gly Gly Gly Ser  Gly Gly Gly
    1040                1045                1050

Gly Ser  Gly Gly Gly Gly Ser  Gly Gly Gly Gly Ser  Gly Gly Gly
    1055                1060                1065

Gly Ser  Gly Gly Gly Gly Ser  Gly Gly Gly Gly Ser  Gly Gly Gly
    1070                1075                1080

Gly Ser  Gly Gly Gly Gly Ser  Gly Gly Gly Gly Ser  Gly Gly Gly
    1085                1090                1095

Gly Ser  Gly Gly Gly Gly Ser  Gly Gly Gly Gly Ser  Gly Gly Gly
    1100                1105                1110

Gly Ser  Gly Gly Gly Gly Ser  Gly Gly Gly Gly Ser  Gly Gly Gly
    1115                1120                1125

Gly Ser  Gly Gly Gly Gly Ser  Gly Gly Gly Gly Ser  Gly Gly Gly
    1130                1135                1140

Gly Ser  Gly Gly Gly Gly Ser  Gly Gly Gly Gly Ser  Gly Gly Gly
    1145                1150                1155

Gly Ser  Gly Gly Gly Gly Ser  Gly Gly Gly Gly Ser  Gly Gly Gly
    1160                1165                1170

Gly Ser  Gly Gly Gly Gly Ser  Gly Gly Gly Gly Ser  Gly Gly Gly
    1175                1180                1185

Gly Ser  Gly Gly Gly Gly Ser  Gly Gly Gly Gly Ser  Gly Gly Gly
    1190                1195                1200

Gly Ser Gly Gly Gly Gly Ser Gly Gly Gly Gly Ser Gly Gly Gly
    1205                1210                1215

Gly Ser Gly Gly Gly Gly Ser Gly Gly Gly Gly Ser Gly Gly Gly
    1220                1225                1230

Gly Ser Gly Gly Gly Gly Ser Gly Gly Gly Gly Ser Gly Gly Gly
    1235                1240                1245

Gly Ser Gly Gly Gly Gly Ser Gly Gly Gly Gly Ser Gly Gly Gly
    1250                1255                1260

Gly Ser Gly Gly Gly Gly Ser Gly Gly Gly Gly Ser Gly Gly Gly
    1265                1270                1275

Gly Ser Gly Gly Gly Gly Ser Gly Gly Gly Gly Ser Gly Gly Gly
    1280                1285                1290

Gly Ser Gly Gly Gly Gly Ser Gly Gly Gly Gly Ser Gly Gly Gly
    1295                1300                1305

Gly Ser Gly Gly Gly Gly Ser Gly Gly Gly Gly Ser Gly Gly Gly
    1310                1315                1320

Gly Ser Gly Gly Gly Gly Ser Gly Gly Gly Gly Ser Gly Gly Gly
    1325                1330                1335

Gly Ser Gly Gly Gly Gly Ser Gly Gly Gly Gly Ser Gly Gly Gly
    1340                1345                1350

Gly Ser Gly Gly Gly Gly Ser Gly Gly Gly Gly Ser Gly Gly Gly
    1355                1360                1365

Gly Ser Gly Gly Gly Gly Ser Gly Gly Gly Gly Ser Gly Gly Gly
    1370                1375                1380

Gly Ser Gly Gly Gly Gly Ser Gly Gly Gly Gly Ser Gly Gly Gly
    1385                1390                1395

Gly Ser Gly Gly Gly Gly Ser Gly Gly Gly Gly Ser Gly Gly Gly
    1400                1405                1410

Gly Ser Gly Gly Gly Gly Ser Gly Gly Gly Gly Ser Gly Gly Gly
    1415                1420                1425

Gly Ser Gly Gly Gly Gly Ser Gly Gly Gly Gly Ser Gly Gly Gly
    1430                1435                1440

Gly Ser Gly Gly Gly Gly Ser Gly Gly Gly Gly Ser Gly Gly Gly
    1445                1450                1455

Gly Ser Gly Gly Gly Gly Ser Gly Gly Gly Gly Ser Gly Gly Gly
    1460                1465                1470

Gly Ser Gly Gly Gly Gly Ser Gly Gly Gly Gly Ser Gly Gly Gly
    1475                1480                1485

Gly Ser Gly Gly Gly Gly Ser Gly Gly Gly Gly Ser Gly Gly Gly
    1490                1495                1500

Gly Ser Gly Gly Gly Gly Ser Gly Gly Gly Gly Ser Gly Gly Gly
    1505                1510                1515

Gly Ser Gly Gly Gly Gly Ser Gly Gly Gly Gly Ser Gly Gly Gly
    1520                1525                1530

Gly Ser Gly Gly Gly Gly Ser Gly Gly Gly Gly Ser Gly Gly Gly
    1535                1540                1545

Gly Ser Gly Gly Gly Gly Ser Gly Gly Gly Gly Ser Gly Gly Gly
    1550                1555                1560

Gly Ser Gly Gly Gly Gly Ser Gly Gly Gly Gly Ser Gly Gly Gly
    1565                1570                1575

Gly Ser Gly Gly Gly Gly Ser Gly Gly Gly Gly Ser Gly Gly Gly
    1580                1585                1590

Gly Ser Gly Gly Gly Gly Ser Gly Gly Gly Gly Ser Gly Gly Gly

-continued

Gly Ser Gly Gly Gly Gly Ser Gly Gly Gly Gly Ser Gly Gly Gly
1610                1615                1620

Gly Ser Gly Gly Gly Gly Ser Gly Gly Gly Gly Ser Gly Gly Gly
1625                1630                1635

Gly Ser Gly Gly Gly Gly Ser Gly Gly Gly Gly Ser Gly Gly Gly
1640                1645                1650

Gly Ser Gly Gly Gly Gly Ser Gly Gly Gly Gly Ser Gly Gly Gly
1655                1660                1665

Gly Ser Gly Gly Gly Gly Ser Gly Gly Gly Gly Ser Gly Gly Gly
1670                1675                1680

Gly Ser Gly Gly Gly Gly Ser Gly Gly Gly Gly Ser Gly Gly Gly
1685                1690                1695

Gly Ser Gly Gly Gly Gly Ser Gly Gly Gly Gly Ser Gly Gly Gly
1700                1705                1710

Gly Ser Gly Gly Gly Gly Ser Gly Gly Gly Gly Ser Gly Gly Gly
1715                1720                1725

Gly Ser Gly Gly Gly Gly Ser Gly Gly Gly Gly Ser Gly Gly Gly
1730                1735                1740

Gly Ser Gly Gly Gly Gly Ser Gly Gly Gly Gly Ser Gly Gly Gly
1745                1750                1755

Gly Ser Gly Gly Gly Gly Ser Gly Gly Gly Gly Ser Gly Gly Gly
1760                1765                1770

Gly Ser Gly Gly Gly Gly Ser Gly Gly Gly Gly Ser Gly Gly Gly
1775                1780                1785

Gly Ser Gly Gly Gly Gly Ser Gly Gly Gly Gly Ser Gly Gly Gly
1790                1795                1800

Gly Ser Gly Gly Gly Gly Ser Gly Gly Gly Gly Ser Gly Gly Gly
1805                1810                1815

Gly Ser Gly Gly Gly Gly Ser Gly Gly Gly Gly Ser Gly Gly Gly
1820                1825                1830

Gly Ser Gly Gly Gly Gly Ser Gly Gly Gly Gly Ser Gly Gly Gly
1835                1840                1845

Gly Ser Gly Gly Gly Gly Ser Gly Gly Gly Gly Ser Gly Gly Gly
1850                1855                1860

Gly Ser Gly Gly Gly Gly Ser Gly Gly Gly Gly Ser Gly Gly Gly
1865                1870                1875

Gly Ser Gly Gly Gly Gly Ser Gly Gly Gly Gly Ser Gly Gly Gly
1880                1885                1890

Gly Ser Gly Gly Gly Gly Ser Gly Gly Gly Gly Ser Gly Gly Gly
1895                1900                1905

Gly Ser Gly Gly Gly Gly Ser Gly Gly Gly Gly Ser Gly Gly Gly
1910                1915                1920

Gly Ser Gly Gly Gly Gly Ser Gly Gly Gly Gly Ser Gly Gly Gly
1925                1930                1935

Gly Ser Gly Gly Gly Gly Ser Gly Gly Gly Gly Ser Gly Gly Gly
1940                1945                1950

Gly Ser Gly Gly Gly Gly Ser Gly Gly Gly Gly Ser Gly Gly Gly
1955                1960                1965

Gly Ser Gly Gly Gly Gly Ser Gly Gly Gly Gly Ser Gly Gly Gly
1970                1975                1980

Gly Ser Gly Gly Gly Gly Ser Gly Gly Gly Gly Ser Gly Gly Gly
1985                1990                1995

```
Gly Ser
    2000

<210> SEQ ID NO 8
<211> LENGTH: 2000
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (6)..(2000)
<223> OTHER INFORMATION: these nucleotides may be absent

<400> SEQUENCE: 8

Gly Ser Gly Ser Gly Gly Ser Gly Ser Gly Gly Ser Gly Ser Gly Gly
1               5                   10                  15

Ser Gly Ser Gly Gly Ser Gly Ser Gly Gly Ser Gly Ser Gly Gly Ser
                20                  25                  30

Gly Ser Gly Gly Ser Gly Ser Gly Gly Ser Gly Ser Gly Gly Ser Gly
            35                  40                  45

Ser Gly Gly Ser Gly Ser Gly Gly Ser Gly Ser Gly Gly Ser Gly Ser
        50                  55                  60

Gly Gly Ser Gly Ser Gly Gly Ser Gly Ser Gly Gly Ser Gly Ser Gly
65                  70                  75                  80

Gly Ser Gly Ser Gly Gly Ser Gly Ser Gly Gly Ser Gly Ser Gly Gly
                85                  90                  95

Ser Gly Ser Gly Gly Ser Gly Ser Gly Gly Ser Gly Ser Gly Gly Ser
                100                 105                 110

Gly Ser Gly Gly Ser Gly Ser Gly Gly Ser Gly Ser Gly Gly Ser Gly
            115                 120                 125

Ser Gly Gly Ser Gly Ser Gly Gly Ser Gly Ser Gly Gly Ser Gly Ser
        130                 135                 140

Gly Gly Ser Gly Ser Gly Gly Ser Gly Ser Gly Gly Ser Gly Ser Gly
145                 150                 155                 160

Gly Ser Gly Ser Gly Gly Ser Gly Ser Gly Gly Ser Gly Ser Gly Gly
                165                 170                 175

Ser Gly Ser Gly Gly Ser Gly Ser Gly Gly Ser Gly Ser Gly Gly Ser
                180                 185                 190

Gly Ser Gly Gly Ser Gly Ser Gly Gly Ser Gly Ser Gly Gly Ser Gly
            195                 200                 205

Ser Gly Gly Ser Gly Ser Gly Gly Ser Gly Ser Gly Gly Ser Gly Ser
        210                 215                 220

Gly Gly Ser Gly Ser Gly Gly Ser Gly Ser Gly Gly Ser Gly Ser Gly
225                 230                 235                 240

Gly Ser Gly Ser Gly Gly Ser Gly Ser Gly Gly Ser Gly Ser Gly Gly
                245                 250                 255

Ser Gly Ser Gly Gly Ser Gly Ser Gly Gly Ser Gly Ser Gly Gly Ser
                260                 265                 270

Gly Ser Gly Gly Ser Gly Ser Gly Gly Ser Gly Ser Gly Gly Ser Gly
            275                 280                 285

Ser Gly Gly Ser Gly Ser Gly Gly Ser Gly Ser Gly Gly Ser Gly Ser
        290                 295                 300

Gly Gly Ser Gly Ser Gly Gly Ser Gly Ser Gly Gly Ser Gly Ser Gly
305                 310                 315                 320

Gly Ser Gly Ser Gly Gly Ser Gly Ser Gly Gly Ser Gly Ser Gly Gly
```

```
            325                 330                 335
Ser Gly Ser Gly Gly Ser Gly Ser Gly Ser Gly Ser Gly Gly Ser
        340                 345                 350
Gly Ser Gly Gly Ser Gly Ser Gly Ser Gly Ser Gly Gly Ser Gly
        355                 360                 365
Ser Gly Gly Ser Gly Ser Gly Ser Gly Ser Gly Gly Ser Gly Ser
        370                 375                 380
Gly Gly Ser Gly Ser Gly Ser Gly Ser Gly Gly Ser Gly Ser Gly
385                 390                 395                 400
Gly Ser Gly Ser Gly Gly Ser Gly Ser Gly Ser Gly Ser Gly Gly
            405                 410                 415
Ser Gly Ser Gly Gly Ser Gly Ser Gly Ser Gly Ser Gly Gly Ser
        420                 425                 430
Gly Ser Gly Gly Ser Gly Ser Gly Ser Gly Ser Gly Gly Ser Gly
        435                 440                 445
Ser Gly Gly Ser Gly Ser Gly Ser Gly Ser Gly Gly Ser Gly Ser
        450                 455                 460
Gly Gly Ser Gly Ser Gly Ser Gly Ser Gly Gly Ser Gly Ser Gly
465                 470                 475                 480
Gly Ser Gly Ser Gly Gly Ser Gly Ser Gly Ser Gly Ser Gly Gly
            485                 490                 495
Ser Gly Ser Gly Gly Ser Gly Ser Gly Ser Gly Ser Gly Gly Ser
        500                 505                 510
Gly Ser Gly Gly Ser Gly Ser Gly Ser Gly Ser Gly Gly Ser Gly
        515                 520                 525
Ser Gly Gly Ser Gly Ser Gly Ser Gly Ser Gly Gly Ser Gly Ser
        530                 535                 540
Gly Gly Ser Gly Ser Gly Ser Gly Ser Gly Gly Ser Gly Ser Gly
545                 550                 555                 560
Gly Ser Gly Ser Gly Gly Ser Gly Ser Gly Ser Gly Ser Gly Gly
            565                 570                 575
Ser Gly Ser Gly Gly Ser Gly Ser Gly Ser Gly Ser Gly Gly Ser
        580                 585                 590
Gly Ser Gly Gly Ser Gly Ser Gly Ser Gly Ser Gly Gly Ser Gly
        595                 600                 605
Ser Gly Gly Ser Gly Ser Gly Ser Gly Ser Gly Gly Ser Gly Ser
        610                 615                 620
Gly Gly Ser Gly Ser Gly Ser Gly Ser Gly Gly Ser Gly Ser Gly
625                 630                 635                 640
Gly Ser Gly Ser Gly Gly Ser Gly Ser Gly Ser Gly Ser Gly Gly
            645                 650                 655
Ser Gly Ser Gly Gly Ser Gly Ser Gly Ser Gly Ser Gly Gly Ser
        660                 665                 670
Gly Ser Gly Gly Ser Gly Ser Gly Ser Gly Ser Gly Gly Ser Gly
        675                 680                 685
Ser Gly Gly Ser Gly Ser Gly Ser Gly Ser Gly Gly Ser Gly Ser
        690                 695                 700
Gly Gly Ser Gly Ser Gly Ser Gly Ser Gly Gly Ser Gly Ser Gly
705                 710                 715                 720
Gly Ser Gly Ser Gly Gly Ser Gly Ser Gly Ser Gly Ser Gly Gly
            725                 730                 735
Ser Gly Ser Gly Gly Ser Gly Ser Gly Ser Gly Ser Gly Gly Ser
        740                 745                 750
```

Gly Ser Gly Gly Ser Gly Ser Gly Gly Ser Gly Ser Gly Gly Ser Gly
        755                 760                 765

Ser Gly Gly Ser Gly Ser Gly Gly Ser Gly Ser Gly Gly Ser Gly Ser
        770                 775                 780

Gly Gly Ser Gly Ser Gly Gly Ser Gly Ser Gly Gly Ser Gly Ser Gly
785                 790                 795                 800

Gly Ser Gly Ser Gly Gly Ser Gly Ser Gly Gly Ser Gly Ser Gly Gly
            805                 810                 815

Ser Gly Ser Gly Gly Ser Gly Ser Gly Gly Ser Gly Ser Gly Gly Ser
        820                 825                 830

Gly Ser Gly Gly Ser Gly Ser Gly Gly Ser Gly Ser Gly Gly Ser Gly
        835                 840                 845

Ser Gly Gly Ser Gly Ser Gly Gly Ser Gly Ser Gly Gly Ser Gly Ser
        850                 855                 860

Gly Gly Ser Gly Ser Gly Gly Ser Gly Ser Gly Gly Ser Gly Ser Gly
865                 870                 875                 880

Gly Ser Gly Ser Gly Gly Ser Gly Ser Gly Gly Ser Gly Ser Gly Gly
            885                 890                 895

Ser Gly Ser Gly Gly Ser Gly Ser Gly Gly Ser Gly Ser Gly Gly Ser
        900                 905                 910

Gly Ser Gly Gly Ser Gly Ser Gly Gly Ser Gly Ser Gly Gly Ser Gly
        915                 920                 925

Ser Gly Gly Ser Gly Ser Gly Gly Ser Gly Ser Gly Gly Ser Gly Ser
        930                 935                 940

Gly Gly Ser Gly Ser Gly Gly Ser Gly Ser Gly Gly Ser Gly Ser Gly
945                 950                 955                 960

Gly Ser Gly Ser Gly Gly Ser Gly Ser Gly Gly Ser Gly Ser Gly Gly
            965                 970                 975

Ser Gly Ser Gly Gly Ser Gly Gly Ser Gly Ser Gly Gly Ser Gly Ser
        980                 985                 990

Gly Ser Gly Gly Ser Gly Ser Gly  Gly Ser Gly Ser Gly  Gly Ser Gly
        995                1000                1005

Ser Gly  Gly Ser Gly Ser Gly  Gly Ser Gly Ser Gly  Gly Ser Gly
       1010                1015                1020

Ser Gly  Gly Ser Gly Ser Gly  Gly Ser Gly Ser Gly  Gly Ser Gly
       1025                1030                1035

Ser Gly  Gly Ser Gly Ser Gly  Gly Ser Gly Ser Gly  Gly Ser Gly
       1040                1045                1050

Ser Gly  Gly Ser Gly Ser Gly  Gly Ser Gly Ser Gly  Gly Ser Gly
       1055                1060                1065

Ser Gly  Gly Ser Gly Ser Gly  Gly Ser Gly Ser Gly  Gly Ser Gly
       1070                1075                1080

Ser Gly  Gly Ser Gly Ser Gly  Gly Ser Gly Ser Gly  Gly Ser Gly
       1085                1090                1095

Ser Gly  Gly Ser Gly Ser Gly  Gly Ser Gly Ser Gly  Gly Ser Gly
       1100                1105                1110

Ser Gly  Gly Ser Gly Ser Gly  Gly Ser Gly Ser Gly  Gly Ser Gly
       1115                1120                1125

Ser Gly  Gly Ser Gly Ser Gly  Gly Ser Gly Ser Gly  Gly Ser Gly
       1130                1135                1140

Ser Gly  Gly Ser Gly Ser Gly  Gly Ser Gly Ser Gly  Gly Ser Gly
       1145                1150                1155

```
Ser Gly Gly Ser Gly Ser Gly  Gly Ser Gly Ser Gly  Gly Ser Gly
    1160            1165              1170

Ser Gly Gly Ser Gly Ser Gly  Gly Ser Gly Ser Gly  Gly Ser Gly
    1175            1180              1185

Ser Gly Gly Ser Gly Ser Gly  Gly Ser Gly Ser Gly  Gly Ser Gly
    1190            1195              1200

Ser Gly Gly Ser Gly Ser Gly  Gly Ser Gly Ser Gly  Gly Ser Gly
    1205            1210              1215

Ser Gly Gly Ser Gly Ser Gly  Gly Ser Gly Ser Gly  Gly Ser Gly
    1220            1225              1230

Ser Gly Gly Ser Gly Ser Gly  Gly Ser Gly Ser Gly  Gly Ser Gly
    1235            1240              1245

Ser Gly Gly Ser Gly Ser Gly  Gly Ser Gly Ser Gly  Gly Ser Gly
    1250            1255              1260

Ser Gly Gly Ser Gly Ser Gly  Gly Ser Gly Ser Gly  Gly Ser Gly
    1265            1270              1275

Ser Gly Gly Ser Gly Ser Gly  Gly Ser Gly Ser Gly  Gly Ser Gly
    1280            1285              1290

Ser Gly Gly Ser Gly Ser Gly  Gly Ser Gly Ser Gly  Gly Ser Gly
    1295            1300              1305

Ser Gly Gly Ser Gly Ser Gly  Gly Ser Gly Ser Gly  Gly Ser Gly
    1310            1315              1320

Ser Gly Gly Ser Gly Ser Gly  Gly Ser Gly Ser Gly  Gly Ser Gly
    1325            1330              1335

Ser Gly Gly Ser Gly Ser Gly  Gly Ser Gly Ser Gly  Gly Ser Gly
    1340            1345              1350

Ser Gly Gly Ser Gly Ser Gly  Gly Ser Gly Ser Gly  Gly Ser Gly
    1355            1360              1365

Ser Gly Gly Ser Gly Ser Gly  Gly Ser Gly Ser Gly  Gly Ser Gly
    1370            1375              1380

Ser Gly Gly Ser Gly Ser Gly  Gly Ser Gly Ser Gly  Gly Ser Gly
    1385            1390              1395

Ser Gly Gly Ser Gly Ser Gly  Gly Ser Gly Ser Gly  Gly Ser Gly
    1400            1405              1410

Ser Gly Gly Ser Gly Ser Gly  Gly Ser Gly Ser Gly  Gly Ser Gly
    1415            1420              1425

Ser Gly Gly Ser Gly Ser Gly  Gly Ser Gly Ser Gly  Gly Ser Gly
    1430            1435              1440

Ser Gly Gly Ser Gly Ser Gly  Gly Ser Gly Ser Gly  Gly Ser Gly
    1445            1450              1455

Ser Gly Gly Ser Gly Ser Gly  Gly Ser Gly Ser Gly  Gly Ser Gly
    1460            1465              1470

Ser Gly Gly Ser Gly Ser Gly  Gly Ser Gly Ser Gly  Gly Ser Gly
    1475            1480              1485

Ser Gly Gly Ser Gly Ser Gly  Gly Ser Gly Ser Gly  Gly Ser Gly
    1490            1495              1500

Ser Gly Gly Ser Gly Ser Gly  Gly Ser Gly Ser Gly  Gly Ser Gly
    1505            1510              1515

Ser Gly Gly Ser Gly Ser Gly  Gly Ser Gly Ser Gly  Gly Ser Gly
    1520            1525              1530

Ser Gly Gly Ser Gly Ser Gly  Gly Ser Gly Ser Gly  Gly Ser Gly
    1535            1540              1545

Ser Gly Gly Ser Gly Ser Gly  Gly Ser Gly Ser Gly  Gly Ser Gly
```

-continued

```
            1550                1555                1560

Ser Gly Gly Ser Gly Ser Gly  Gly Ser Gly Ser Gly  Gly Ser Gly
    1565                1570                1575

Ser Gly Gly Ser Gly Ser Gly  Gly Ser Gly Ser Gly  Gly Ser Gly
    1580                1585                1590

Ser Gly Gly Ser Gly Ser Gly  Gly Ser Gly Ser Gly  Gly Ser Gly
    1595                1600                1605

Ser Gly Gly Ser Gly Ser Gly  Gly Ser Gly Ser Gly  Gly Ser Gly
    1610                1615                1620

Ser Gly Gly Ser Gly Ser Gly  Gly Ser Gly Ser Gly  Gly Ser Gly
    1625                1630                1635

Ser Gly Gly Ser Gly Ser Gly  Gly Ser Gly Ser Gly  Gly Ser Gly
    1640                1645                1650

Ser Gly Gly Ser Gly Ser Gly  Gly Ser Gly Ser Gly  Gly Ser Gly
    1655                1660                1665

Ser Gly Gly Ser Gly Ser Gly  Gly Ser Gly Ser Gly  Gly Ser Gly
    1670                1675                1680

Ser Gly Gly Ser Gly Ser Gly  Gly Ser Gly Ser Gly  Gly Ser Gly
    1685                1690                1695

Ser Gly Gly Ser Gly Ser Gly  Gly Ser Gly Ser Gly  Gly Ser Gly
    1700                1705                1710

Ser Gly Gly Ser Gly Ser Gly  Gly Ser Gly Ser Gly  Gly Ser Gly
    1715                1720                1725

Ser Gly Gly Ser Gly Ser Gly  Gly Ser Gly Ser Gly  Gly Ser Gly
    1730                1735                1740

Ser Gly Gly Ser Gly Ser Gly  Gly Ser Gly Ser Gly  Gly Ser Gly
    1745                1750                1755

Ser Gly Gly Ser Gly Ser Gly  Gly Ser Gly Ser Gly  Gly Ser Gly
    1760                1765                1770

Ser Gly Gly Ser Gly Ser Gly  Gly Ser Gly Ser Gly  Gly Ser Gly
    1775                1780                1785

Ser Gly Gly Ser Gly Ser Gly  Gly Ser Gly Ser Gly  Gly Ser Gly
    1790                1795                1800

Ser Gly Gly Ser Gly Ser Gly  Gly Ser Gly Ser Gly  Gly Ser Gly
    1805                1810                1815

Ser Gly Gly Ser Gly Ser Gly  Gly Ser Gly Ser Gly  Gly Ser Gly
    1820                1825                1830

Ser Gly Gly Ser Gly Ser Gly  Gly Ser Gly Ser Gly  Gly Ser Gly
    1835                1840                1845

Ser Gly Gly Ser Gly Ser Gly  Gly Ser Gly Ser Gly  Gly Ser Gly
    1850                1855                1860

Ser Gly Gly Ser Gly Ser Gly  Gly Ser Gly Ser Gly  Gly Ser Gly
    1865                1870                1875

Ser Gly Gly Ser Gly Ser Gly  Gly Ser Gly Ser Gly  Gly Ser Gly
    1880                1885                1890

Ser Gly Gly Ser Gly Ser Gly  Gly Ser Gly Ser Gly  Gly Ser Gly
    1895                1900                1905

Ser Gly Gly Ser Gly Ser Gly  Gly Ser Gly Ser Gly  Gly Ser Gly
    1910                1915                1920

Ser Gly Gly Ser Gly Ser Gly  Gly Ser Gly Ser Gly  Gly Ser Gly
    1925                1930                1935

Ser Gly Gly Ser Gly Ser Gly  Gly Ser Gly Ser Gly  Gly Ser Gly
    1940                1945                1950
```

Ser Gly Gly Ser Gly Ser Gly Gly Ser Gly Ser Gly Gly Ser Gly
    1955                1960                1965

Ser Gly Gly Ser Gly Ser Gly Gly Ser Gly Ser Gly Gly Ser Gly
    1970                1975                1980

Ser Gly Gly Ser Gly Ser Gly Gly Ser Gly Ser Gly Gly Ser Gly
    1985                1990                1995

Ser Gly
    2000

<210> SEQ ID NO 9
<211> LENGTH: 4000
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (11)..(4000)
<223> OTHER INFORMATION: these nucleotides may be absent

<400> SEQUENCE: 9

Gly Ser Gly Ser Gly Gly Ser Gly Ser Gly Gly Ser Gly Ser Gly Gly
1               5                   10                  15

Ser Gly Ser Gly Gly Ser Gly Ser Gly Gly Ser Gly Ser Gly Gly Ser
            20                  25                  30

Gly Ser Gly Gly Ser Gly Ser Gly Gly Ser Gly Ser Gly Gly Ser Gly
        35                  40                  45

Ser Gly Gly Ser Gly Ser Gly Gly Ser Gly Ser Gly Gly Ser Gly Ser
    50                  55                  60

Gly Gly Ser Gly Ser Gly Gly Ser Gly Ser Gly Gly Ser Gly Ser Gly
65                  70                  75                  80

Gly Ser Gly Ser Gly Gly Ser Gly Ser Gly Gly Ser Gly Ser Gly Gly
                85                  90                  95

Ser Gly Ser Gly Gly Ser Gly Ser Gly Gly Ser Gly Ser Gly Gly Ser
            100                 105                 110

Gly Ser Gly Gly Ser Gly Ser Gly Gly Ser Gly Ser Gly Gly Ser Gly
        115                 120                 125

Ser Gly Gly Ser Gly Ser Gly Gly Ser Gly Ser Gly Gly Ser Gly Ser
    130                 135                 140

Gly Gly Ser Gly Ser Gly Gly Ser Gly Ser Gly Gly Ser Gly Ser Gly
145                 150                 155                 160

Gly Ser Gly Ser Gly Gly Ser Gly Ser Gly Gly Ser Gly Ser Gly Gly
                165                 170                 175

Ser Gly Ser Gly Gly Ser Gly Ser Gly Gly Ser Gly Ser Gly Gly Ser
            180                 185                 190

Gly Ser Gly Gly Ser Gly Ser Gly Gly Ser Gly Ser Gly Gly Ser Gly
        195                 200                 205

Ser Gly Gly Ser Gly Ser Gly Gly Ser Gly Ser Gly Gly Ser Gly Ser
    210                 215                 220

Gly Gly Ser Gly Ser Gly Gly Ser Gly Ser Gly Gly Ser Gly Ser Gly
225                 230                 235                 240

Gly Ser Gly Ser Gly Gly Ser Gly Ser Gly Gly Ser Gly Ser Gly Gly
                245                 250                 255

Ser Gly Ser Gly Gly Ser Gly Ser Gly Gly Ser Gly Ser Gly Gly Ser
            260                 265                 270

Gly Ser Gly Gly Ser Gly Ser Gly Gly Ser Gly Ser Gly Gly Ser Gly

```
            275                 280                 285
Ser Gly Gly Ser Gly Ser Gly Gly Ser Gly Ser Gly Ser Gly Ser
    290                 295                 300
Gly Gly Ser Gly Ser Gly Ser Gly Gly Ser Gly Ser Gly Ser Gly
305                 310                 315                 320
Gly Ser Gly Ser Gly Ser Gly Gly Ser Gly Ser Gly Ser Gly Gly
                325                 330                 335
Ser Gly Ser Gly Ser Gly Gly Ser Gly Ser Gly Ser Gly Gly Ser
            340                 345                 350
Gly Ser Gly Ser Gly Ser Gly Gly Ser Gly Ser Gly Ser Gly Gly
        355                 360                 365
Ser Gly Gly Ser Gly Ser Gly Gly Ser Gly Ser Gly Ser Gly Ser
    370                 375                 380
Gly Gly Ser Gly Ser Gly Ser Gly Gly Ser Gly Ser Gly Ser Gly
385                 390                 395                 400
Gly Ser Gly Ser Gly Ser Gly Ser Gly Ser Gly Ser Gly Ser Gly
                405                 410                 415
Ser Gly Ser Gly Gly Ser Gly Ser Gly Gly Ser Gly Gly Gly Ser
            420                 425                 430
Gly Ser Gly Gly Ser Gly Ser Gly Ser Gly Gly Ser Gly Ser Gly
        435                 440                 445
Ser Gly Gly Ser Gly Ser Gly Gly Ser Gly Ser Gly Ser Gly Ser
    450                 455                 460
Gly Gly Ser Gly Ser Gly Ser Gly Gly Ser Gly Ser Gly Ser Gly
465                 470                 475                 480
Gly Ser Gly Ser Gly Ser Gly Gly Ser Gly Ser Gly Ser Gly Gly
                485                 490                 495
Ser Gly Ser Gly Ser Gly Gly Ser Gly Ser Gly Ser Gly Gly Ser
            500                 505                 510
Gly Ser Gly Ser Gly Ser Gly Gly Ser Gly Ser Gly Ser Gly Gly
        515                 520                 525
Ser Gly Gly Ser Gly Ser Gly Gly Ser Gly Ser Gly Ser Gly Ser
    530                 535                 540
Gly Gly Ser Gly Ser Gly Ser Gly Gly Ser Gly Ser Gly Ser Gly
545                 550                 555                 560
Gly Ser Gly Ser Gly Ser Gly Ser Gly Ser Gly Ser Gly Ser Gly
                565                 570                 575
Ser Gly Ser Gly Gly Ser Gly Ser Gly Gly Ser Gly Gly Gly Ser
            580                 585                 590
Gly Ser Gly Gly Ser Gly Ser Gly Ser Gly Gly Ser Gly Ser Gly
        595                 600                 605
Ser Gly Gly Ser Gly Ser Gly Gly Ser Gly Ser Gly Ser Gly Ser
    610                 615                 620
Gly Gly Ser Gly Ser Gly Ser Gly Gly Ser Gly Ser Gly Ser Gly
625                 630                 635                 640
Gly Ser Gly Ser Gly Ser Gly Gly Ser Gly Ser Gly Ser Gly Gly
                645                 650                 655
Ser Gly Ser Gly Gly Ser Gly Ser Gly Gly Ser Gly Ser Gly Ser
            660                 665                 670
Gly Ser Gly Ser Gly Ser Gly Gly Ser Gly Ser Gly Gly Ser Gly
        675                 680                 685
Ser Gly Gly Ser Gly Ser Gly Gly Ser Gly Ser Gly Gly Ser Gly Ser
    690                 695                 700
```

Gly Gly Ser Gly Ser Gly Ser Gly Ser Gly Ser Gly Ser Gly
705                 710                 715                 720

Gly Ser Gly Ser Gly Ser Gly Ser Gly Ser Gly Ser Gly Gly
            725                 730                 735

Ser Gly Ser Gly Gly Ser Gly Ser Gly Ser Gly Ser Gly Ser
                740                 745                 750

Gly Ser Gly Ser Gly Ser Gly Gly Ser Gly Ser Gly Ser Gly
            755                 760                 765

Ser Gly Gly Ser Gly Ser Gly Ser Gly Ser Gly Gly Ser Gly
770                 775                 780

Gly Gly Ser Gly Ser Gly Gly Ser Gly Ser Gly Gly Ser Gly
785                 790                 795                 800

Gly Ser Gly Ser Gly Gly Ser Gly Ser Gly Ser Gly Ser Gly
            805                 810                 815

Ser Gly Ser Gly Gly Ser Gly Gly Ser Gly Ser Gly Gly Ser
                820                 825                 830

Gly Ser Gly Gly Ser Gly Ser Gly Gly Ser Gly Gly Ser Gly
            835                 840                 845

Ser Gly Gly Ser Gly Ser Gly Gly Ser Gly Ser Gly Gly Ser
                850                 855                 860

Gly Gly Ser Gly Ser Gly Gly Ser Gly Ser Gly Gly Ser Gly
865                 870                 875                 880

Gly Ser Gly Ser Gly Gly Ser Gly Ser Gly Ser Gly Ser Gly
            885                 890                 895

Ser Gly Ser Gly Gly Ser Gly Ser Gly Gly Ser Gly Gly Ser
                900                 905                 910

Gly Ser Gly Gly Ser Gly Ser Gly Gly Ser Gly Gly Ser Gly
            915                 920                 925

Ser Gly Gly Ser Gly Ser Gly Gly Ser Gly Ser Gly Gly Ser
                930                 935                 940

Gly Gly Ser Gly Ser Gly Gly Ser Gly Ser Gly Gly Ser Gly
945                 950                 955                 960

Gly Ser Gly Ser Gly Gly Ser Gly Ser Gly Ser Gly Ser Gly
            965                 970                 975

Ser Gly Ser Gly Gly Ser Gly Ser Gly Gly Ser Gly Gly Ser
                980                 985                 990

Gly Ser Gly Gly Ser Gly Ser Gly Gly Ser Gly Ser Gly Gly
            995                 1000                 1005

Ser Gly Gly Ser Gly Ser Gly Gly Ser Gly Ser Gly Gly Ser Gly
            1010                 1015                 1020

Ser Gly Gly Ser Gly Ser Gly Gly Ser Gly Ser Gly Gly Ser Gly
            1025                 1030                 1035

Ser Gly Gly Ser Gly Ser Gly Gly Ser Gly Ser Gly Gly Ser Gly
            1040                 1045                 1050

Ser Gly Gly Ser Gly Ser Gly Gly Ser Gly Ser Gly Gly Ser Gly
            1055                 1060                 1065

Ser Gly Gly Ser Gly Ser Gly Gly Ser Gly Ser Gly Gly Ser Gly
            1070                 1075                 1080

Ser Gly Gly Ser Gly Ser Gly Gly Ser Gly Ser Gly Gly Ser Gly
            1085                 1090                 1095

Ser Gly Gly Ser Gly Ser Gly Gly Ser Gly Ser Gly Gly Ser Gly
            1100                 1105                 1110

```
Ser Gly Gly Ser Gly Ser Gly  Gly Ser Gly Ser Gly  Gly Ser Gly
    1115                1120                 1125

Ser Gly Gly Ser Gly Ser Gly  Gly Ser Gly Ser Gly  Gly Ser Gly
    1130                1135                 1140

Ser Gly Gly Ser Gly Ser Gly  Gly Ser Gly Ser Gly  Gly Ser Gly
    1145                1150                 1155

Ser Gly Gly Ser Gly Ser Gly  Gly Ser Gly Ser Gly  Gly Ser Gly
    1160                1165                 1170

Ser Gly Gly Ser Gly Ser Gly  Gly Ser Gly Ser Gly  Gly Ser Gly
    1175                1180                 1185

Ser Gly Gly Ser Gly Ser Gly  Gly Ser Gly Ser Gly  Gly Ser Gly
    1190                1195                 1200

Ser Gly Gly Ser Gly Ser Gly  Gly Ser Gly Ser Gly  Gly Ser Gly
    1205                1210                 1215

Ser Gly Gly Ser Gly Ser Gly  Gly Ser Gly Ser Gly  Gly Ser Gly
    1220                1225                 1230

Ser Gly Gly Ser Gly Ser Gly  Gly Ser Gly Ser Gly  Gly Ser Gly
    1235                1240                 1245

Ser Gly Gly Ser Gly Ser Gly  Gly Ser Gly Ser Gly  Gly Ser Gly
    1250                1255                 1260

Ser Gly Gly Ser Gly Ser Gly  Gly Ser Gly Ser Gly  Gly Ser Gly
    1265                1270                 1275

Ser Gly Gly Ser Gly Ser Gly  Gly Ser Gly Ser Gly  Gly Ser Gly
    1280                1285                 1290

Ser Gly Gly Ser Gly Ser Gly  Gly Ser Gly Ser Gly  Gly Ser Gly
    1295                1300                 1305

Ser Gly Gly Ser Gly Ser Gly  Gly Ser Gly Ser Gly  Gly Ser Gly
    1310                1315                 1320

Ser Gly Gly Ser Gly Ser Gly  Gly Ser Gly Ser Gly  Gly Ser Gly
    1325                1330                 1335

Ser Gly Gly Ser Gly Ser Gly  Gly Ser Gly Ser Gly  Gly Ser Gly
    1340                1345                 1350

Ser Gly Gly Ser Gly Ser Gly  Gly Ser Gly Ser Gly  Gly Ser Gly
    1355                1360                 1365

Ser Gly Gly Ser Gly Ser Gly  Gly Ser Gly Ser Gly  Gly Ser Gly
    1370                1375                 1380

Ser Gly Gly Ser Gly Ser Gly  Gly Ser Gly Ser Gly  Gly Ser Gly
    1385                1390                 1395

Ser Gly Gly Ser Gly Ser Gly  Gly Ser Gly Ser Gly  Gly Ser Gly
    1400                1405                 1410

Ser Gly Gly Ser Gly Ser Gly  Gly Ser Gly Ser Gly  Gly Ser Gly
    1415                1420                 1425

Ser Gly Gly Ser Gly Ser Gly  Gly Ser Gly Ser Gly  Gly Ser Gly
    1430                1435                 1440

Ser Gly Gly Ser Gly Ser Gly  Gly Ser Gly Ser Gly  Gly Ser Gly
    1445                1450                 1455

Ser Gly Gly Ser Gly Ser Gly  Gly Ser Gly Ser Gly  Gly Ser Gly
    1460                1465                 1470

Ser Gly Gly Ser Gly Ser Gly  Gly Ser Gly Ser Gly  Gly Ser Gly
    1475                1480                 1485

Ser Gly Gly Ser Gly Ser Gly  Gly Ser Gly Ser Gly  Gly Ser Gly
    1490                1495                 1500

Ser Gly Gly Ser Gly Ser Gly  Gly Ser Gly Ser Gly  Gly Ser Gly
```

-continued

```
       1505                1510                1515
Ser Gly  Gly Ser Gly Ser Gly  Gly Ser Gly Ser Gly  Gly Ser Gly
       1520                1525                1530
Ser Gly  Gly Ser Gly Ser Gly  Gly Ser Gly Ser Gly  Gly Ser Gly
       1535                1540                1545
Ser Gly  Gly Ser Gly Ser Gly  Gly Ser Gly Ser Gly  Gly Ser Gly
       1550                1555                1560
Ser Gly  Gly Ser Gly Ser Gly  Gly Ser Gly Ser Gly  Gly Ser Gly
       1565                1570                1575
Ser Gly  Gly Ser Gly Ser Gly  Gly Ser Gly Ser Gly  Gly Ser Gly
       1580                1585                1590
Ser Gly  Gly Ser Gly Ser Gly  Gly Ser Gly Ser Gly  Gly Ser Gly
       1595                1600                1605
Ser Gly  Gly Ser Gly Ser Gly  Gly Ser Gly Ser Gly  Gly Ser Gly
       1610                1615                1620
Ser Gly  Gly Ser Gly Ser Gly  Gly Ser Gly Ser Gly  Gly Ser Gly
       1625                1630                1635
Ser Gly  Gly Ser Gly Ser Gly  Gly Ser Gly Ser Gly  Gly Ser Gly
       1640                1645                1650
Ser Gly  Gly Ser Gly Ser Gly  Gly Ser Gly Ser Gly  Gly Ser Gly
       1655                1660                1665
Ser Gly  Gly Ser Gly Ser Gly  Gly Ser Gly Ser Gly  Gly Ser Gly
       1670                1675                1680
Ser Gly  Gly Ser Gly Ser Gly  Gly Ser Gly Ser Gly  Gly Ser Gly
       1685                1690                1695
Ser Gly  Gly Ser Gly Ser Gly  Gly Ser Gly Ser Gly  Gly Ser Gly
       1700                1705                1710
Ser Gly  Gly Ser Gly Ser Gly  Gly Ser Gly Ser Gly  Gly Ser Gly
       1715                1720                1725
Ser Gly  Gly Ser Gly Ser Gly  Gly Ser Gly Ser Gly  Gly Ser Gly
       1730                1735                1740
Ser Gly  Gly Ser Gly Ser Gly  Gly Ser Gly Ser Gly  Gly Ser Gly
       1745                1750                1755
Ser Gly  Gly Ser Gly Ser Gly  Gly Ser Gly Ser Gly  Gly Ser Gly
       1760                1765                1770
Ser Gly  Gly Ser Gly Ser Gly  Gly Ser Gly Ser Gly  Gly Ser Gly
       1775                1780                1785
Ser Gly  Gly Ser Gly Ser Gly  Gly Ser Gly Ser Gly  Gly Ser Gly
       1790                1795                1800
Ser Gly  Gly Ser Gly Ser Gly  Gly Ser Gly Ser Gly  Gly Ser Gly
       1805                1810                1815
Ser Gly  Gly Ser Gly Ser Gly  Gly Ser Gly Ser Gly  Gly Ser Gly
       1820                1825                1830
Ser Gly  Gly Ser Gly Ser Gly  Gly Ser Gly Ser Gly  Gly Ser Gly
       1835                1840                1845
Ser Gly  Gly Ser Gly Ser Gly  Gly Ser Gly Ser Gly  Gly Ser Gly
       1850                1855                1860
Ser Gly  Gly Ser Gly Ser Gly  Gly Ser Gly Ser Gly  Gly Ser Gly
       1865                1870                1875
Ser Gly  Gly Ser Gly Ser Gly  Gly Ser Gly Ser Gly  Gly Ser Gly
       1880                1885                1890
Ser Gly  Gly Ser Gly Ser Gly  Gly Ser Gly Ser Gly  Gly Ser Gly
       1895                1900                1905
```

```
Ser Gly Gly Ser Gly Ser Gly  Gly Ser Gly Ser Gly  Gly Ser Gly
    1910            1915              1920

Ser Gly Gly Ser Gly Ser Gly  Gly Ser Gly Ser Gly  Gly Ser Gly
    1925            1930              1935

Ser Gly Gly Ser Gly Ser Gly  Gly Ser Gly Ser Gly  Gly Ser Gly
    1940            1945              1950

Ser Gly Gly Ser Gly Ser Gly  Gly Ser Gly Ser Gly  Gly Ser Gly
    1955            1960              1965

Ser Gly Gly Ser Gly Ser Gly  Gly Ser Gly Ser Gly  Gly Ser Gly
    1970            1975              1980

Ser Gly Gly Ser Gly Ser Gly  Gly Ser Gly Ser Gly  Gly Ser Gly
    1985            1990              1995

Ser Gly Gly Ser Gly Ser Gly  Gly Ser Gly Ser Gly  Gly Ser Gly
    2000            2005              2010

Ser Gly Gly Ser Gly Ser Gly  Gly Ser Gly Ser Gly  Gly Ser Gly
    2015            2020              2025

Ser Gly Gly Ser Gly Ser Gly  Gly Ser Gly Ser Gly  Gly Ser Gly
    2030            2035              2040

Ser Gly Gly Ser Gly Ser Gly  Gly Ser Gly Ser Gly  Gly Ser Gly
    2045            2050              2055

Ser Gly Gly Ser Gly Ser Gly  Gly Ser Gly Ser Gly  Gly Ser Gly
    2060            2065              2070

Ser Gly Gly Ser Gly Ser Gly  Gly Ser Gly Ser Gly  Gly Ser Gly
    2075            2080              2085

Ser Gly Gly Ser Gly Ser Gly  Gly Ser Gly Ser Gly  Gly Ser Gly
    2090            2095              2100

Ser Gly Gly Ser Gly Ser Gly  Gly Ser Gly Ser Gly  Gly Ser Gly
    2105            2110              2115

Ser Gly Gly Ser Gly Ser Gly  Gly Ser Gly Ser Gly  Gly Ser Gly
    2120            2125              2130

Ser Gly Gly Ser Gly Ser Gly  Gly Ser Gly Ser Gly  Gly Ser Gly
    2135            2140              2145

Ser Gly Gly Ser Gly Ser Gly  Gly Ser Gly Ser Gly  Gly Ser Gly
    2150            2155              2160

Ser Gly Gly Ser Gly Ser Gly  Gly Ser Gly Ser Gly  Gly Ser Gly
    2165            2170              2175

Ser Gly Gly Ser Gly Ser Gly  Gly Ser Gly Ser Gly  Gly Ser Gly
    2180            2185              2190

Ser Gly Gly Ser Gly Ser Gly  Gly Ser Gly Ser Gly  Gly Ser Gly
    2195            2200              2205

Ser Gly Gly Ser Gly Ser Gly  Gly Ser Gly Ser Gly  Gly Ser Gly
    2210            2215              2220

Ser Gly Gly Ser Gly Ser Gly  Gly Ser Gly Ser Gly  Gly Ser Gly
    2225            2230              2235

Ser Gly Gly Ser Gly Ser Gly  Gly Ser Gly Ser Gly  Gly Ser Gly
    2240            2245              2250

Ser Gly Gly Ser Gly Ser Gly  Gly Ser Gly Ser Gly  Gly Ser Gly
    2255            2260              2265

Ser Gly Gly Ser Gly Ser Gly  Gly Ser Gly Ser Gly  Gly Ser Gly
    2270            2275              2280

Ser Gly Gly Ser Gly Ser Gly  Gly Ser Gly Ser Gly  Gly Ser Gly
    2285            2290              2295
```

Ser Gly Gly Ser Gly Ser Gly Gly Ser Gly Ser Gly Gly Ser Gly
2300                2305                2310

Ser Gly Gly Ser Gly Ser Gly Gly Ser Gly Ser Gly Gly Ser Gly
2315                2320                2325

Ser Gly Gly Ser Gly Ser Gly Gly Ser Gly Ser Gly Gly Ser Gly
2330                2335                2340

Ser Gly Gly Ser Gly Ser Gly Gly Ser Gly Ser Gly Gly Ser Gly
2345                2350                2355

Ser Gly Gly Ser Gly Ser Gly Gly Ser Gly Ser Gly Gly Ser Gly
2360                2365                2370

Ser Gly Gly Ser Gly Ser Gly Gly Ser Gly Ser Gly Gly Ser Gly
2375                2380                2385

Ser Gly Gly Ser Gly Ser Gly Gly Ser Gly Ser Gly Gly Ser Gly
2390                2395                2400

Ser Gly Gly Ser Gly Ser Gly Gly Ser Gly Ser Gly Gly Ser Gly
2405                2410                2415

Ser Gly Gly Ser Gly Ser Gly Gly Ser Gly Ser Gly Gly Ser Gly
2420                2425                2430

Ser Gly Gly Ser Gly Ser Gly Gly Ser Gly Ser Gly Gly Ser Gly
2435                2440                2445

Ser Gly Gly Ser Gly Ser Gly Gly Ser Gly Ser Gly Gly Ser Gly
2450                2455                2460

Ser Gly Gly Ser Gly Ser Gly Gly Ser Gly Ser Gly Gly Ser Gly
2465                2470                2475

Ser Gly Gly Ser Gly Ser Gly Gly Ser Gly Ser Gly Gly Ser Gly
2480                2485                2490

Ser Gly Gly Ser Gly Ser Gly Gly Ser Gly Ser Gly Gly Ser Gly
2495                2500                2505

Ser Gly Gly Ser Gly Ser Gly Gly Ser Gly Ser Gly Gly Ser Gly
2510                2515                2520

Ser Gly Gly Ser Gly Ser Gly Gly Ser Gly Ser Gly Gly Ser Gly
2525                2530                2535

Ser Gly Gly Ser Gly Ser Gly Gly Ser Gly Ser Gly Gly Ser Gly
2540                2545                2550

Ser Gly Gly Ser Gly Ser Gly Gly Ser Gly Ser Gly Gly Ser Gly
2555                2560                2565

Ser Gly Gly Ser Gly Ser Gly Gly Ser Gly Ser Gly Gly Ser Gly
2570                2575                2580

Ser Gly Gly Ser Gly Ser Gly Gly Ser Gly Ser Gly Gly Ser Gly
2585                2590                2595

Ser Gly Gly Ser Gly Ser Gly Gly Ser Gly Ser Gly Gly Ser Gly
2600                2605                2610

Ser Gly Gly Ser Gly Ser Gly Gly Ser Gly Ser Gly Gly Ser Gly
2615                2620                2625

Ser Gly Gly Ser Gly Ser Gly Gly Ser Gly Ser Gly Gly Ser Gly
2630                2635                2640

Ser Gly Gly Ser Gly Ser Gly Gly Ser Gly Ser Gly Gly Ser Gly
2645                2650                2655

Ser Gly Gly Ser Gly Ser Gly Gly Ser Gly Ser Gly Gly Ser Gly
2660                2665                2670

Ser Gly Gly Ser Gly Ser Gly Gly Ser Gly Ser Gly Gly Ser Gly
2675                2680                2685

Ser Gly Gly Ser Gly Ser Gly Gly Ser Gly Ser Gly Gly Ser Gly 2690                2695                2700

Ser Gly Gly Ser Gly Ser Gly Gly Ser Gly Ser Gly Gly Ser Gly
    2705                2710                2715

Ser Gly Gly Ser Gly Ser Gly Gly Ser Gly Ser Gly Gly Ser Gly
    2720                2725                2730

Ser Gly Gly Ser Gly Ser Gly Gly Ser Gly Ser Gly Gly Ser Gly
    2735                2740                2745

Ser Gly Gly Ser Gly Ser Gly Gly Ser Gly Ser Gly Gly Ser Gly
    2750                2755                2760

Ser Gly Gly Ser Gly Ser Gly Gly Ser Gly Ser Gly Gly Ser Gly
    2765                2770                2775

Ser Gly Gly Ser Gly Ser Gly Gly Ser Gly Ser Gly Gly Ser Gly
    2780                2785                2790

Ser Gly Gly Ser Gly Ser Gly Gly Ser Gly Ser Gly Gly Ser Gly
    2795                2800                2805

Ser Gly Gly Ser Gly Ser Gly Gly Ser Gly Ser Gly Gly Ser Gly
    2810                2815                2820

Ser Gly Gly Ser Gly Ser Gly Gly Ser Gly Ser Gly Gly Ser Gly
    2825                2830                2835

Ser Gly Gly Ser Gly Ser Gly Gly Ser Gly Ser Gly Gly Ser Gly
    2840                2845                2850

Ser Gly Gly Ser Gly Ser Gly Gly Ser Gly Ser Gly Gly Ser Gly
    2855                2860                2865

Ser Gly Gly Ser Gly Ser Gly Gly Ser Gly Ser Gly Gly Ser Gly
    2870                2875                2880

Ser Gly Gly Ser Gly Ser Gly Gly Ser Gly Ser Gly Gly Ser Gly
    2885                2890                2895

Ser Gly Gly Ser Gly Ser Gly Gly Ser Gly Ser Gly Gly Ser Gly
    2900                2905                2910

Ser Gly Gly Ser Gly Ser Gly Gly Ser Gly Ser Gly Gly Ser Gly
    2915                2920                2925

Ser Gly Gly Ser Gly Ser Gly Gly Ser Gly Ser Gly Gly Ser Gly
    2930                2935                2940

Ser Gly Gly Ser Gly Ser Gly Gly Ser Gly Ser Gly Gly Ser Gly
    2945                2950                2955

Ser Gly Gly Ser Gly Ser Gly Gly Ser Gly Ser Gly Gly Ser Gly
    2960                2965                2970

Ser Gly Gly Ser Gly Ser Gly Gly Ser Gly Ser Gly Gly Ser Gly
    2975                2980                2985

Ser Gly Gly Ser Gly Ser Gly Gly Ser Gly Ser Gly Gly Ser Gly
    2990                2995                3000

Ser Gly Gly Ser Gly Ser Gly Gly Ser Gly Ser Gly Gly Ser Gly
    3005                3010                3015

Ser Gly Gly Ser Gly Ser Gly Gly Ser Gly Ser Gly Gly Ser Gly
    3020                3025                3030

Ser Gly Gly Ser Gly Ser Gly Gly Ser Gly Ser Gly Gly Ser Gly
    3035                3040                3045

Ser Gly Gly Ser Gly Ser Gly Gly Ser Gly Ser Gly Gly Ser Gly
    3050                3055                3060

Ser Gly Gly Ser Gly Ser Gly Gly Ser Gly Ser Gly Gly Ser Gly
    3065                3070                3075

Ser Gly Gly Ser Gly Ser Gly Gly Ser Gly Ser Gly Gly Ser Gly
    3080                3085                3090

-continued

```
Ser Gly Gly Ser Gly Ser Gly  Gly Ser Gly Ser Gly  Gly Ser Gly
    3095            3100              3105

Ser Gly Gly Ser Gly Ser Gly  Gly Ser Gly Ser Gly  Gly Ser Gly
    3110            3115              3120

Ser Gly Gly Ser Gly Ser Gly  Gly Ser Gly Ser Gly  Gly Ser Gly
    3125            3130              3135

Ser Gly Gly Ser Gly Ser Gly  Gly Ser Gly Ser Gly  Gly Ser Gly
    3140            3145              3150

Ser Gly Gly Ser Gly Ser Gly  Gly Ser Gly Ser Gly  Gly Ser Gly
    3155            3160              3165

Ser Gly Gly Ser Gly Ser Gly  Gly Ser Gly Ser Gly  Gly Ser Gly
    3170            3175              3180

Ser Gly Gly Ser Gly Ser Gly  Gly Ser Gly Ser Gly  Gly Ser Gly
    3185            3190              3195

Ser Gly Gly Ser Gly Ser Gly  Gly Ser Gly Ser Gly  Gly Ser Gly
    3200            3205              3210

Ser Gly Gly Ser Gly Ser Gly  Gly Ser Gly Ser Gly  Gly Ser Gly
    3215            3220              3225

Ser Gly Gly Ser Gly Ser Gly  Gly Ser Gly Ser Gly  Gly Ser Gly
    3230            3235              3240

Ser Gly Gly Ser Gly Ser Gly  Gly Ser Gly Ser Gly  Gly Ser Gly
    3245            3250              3255

Ser Gly Gly Ser Gly Ser Gly  Gly Ser Gly Ser Gly  Gly Ser Gly
    3260            3265              3270

Ser Gly Gly Ser Gly Ser Gly  Gly Ser Gly Ser Gly  Gly Ser Gly
    3275            3280              3285

Ser Gly Gly Ser Gly Ser Gly  Gly Ser Gly Ser Gly  Gly Ser Gly
    3290            3295              3300

Ser Gly Gly Ser Gly Ser Gly  Gly Ser Gly Ser Gly  Gly Ser Gly
    3305            3310              3315

Ser Gly Gly Ser Gly Ser Gly  Gly Ser Gly Ser Gly  Gly Ser Gly
    3320            3325              3330

Ser Gly Gly Ser Gly Ser Gly  Gly Ser Gly Ser Gly  Gly Ser Gly
    3335            3340              3345

Ser Gly Gly Ser Gly Ser Gly  Gly Ser Gly Ser Gly  Gly Ser Gly
    3350            3355              3360

Ser Gly Gly Ser Gly Ser Gly  Gly Ser Gly Ser Gly  Gly Ser Gly
    3365            3370              3375

Ser Gly Gly Ser Gly Ser Gly  Gly Ser Gly Ser Gly  Gly Ser Gly
    3380            3385              3390

Ser Gly Gly Ser Gly Ser Gly  Gly Ser Gly Ser Gly  Gly Ser Gly
    3395            3400              3405

Ser Gly Gly Ser Gly Ser Gly  Gly Ser Gly Ser Gly  Gly Ser Gly
    3410            3415              3420

Ser Gly Gly Ser Gly Ser Gly  Gly Ser Gly Ser Gly  Gly Ser Gly
    3425            3430              3435

Ser Gly Gly Ser Gly Ser Gly  Gly Ser Gly Ser Gly  Gly Ser Gly
    3440            3445              3450

Ser Gly Gly Ser Gly Ser Gly  Gly Ser Gly Ser Gly  Gly Ser Gly
    3455            3460              3465

Ser Gly Gly Ser Gly Ser Gly  Gly Ser Gly Ser Gly  Gly Ser Gly
    3470            3475              3480
```

-continued

```
Ser Gly Gly Ser Gly Ser Gly  Gly Ser Gly Ser Gly  Gly Ser Gly
    3485            3490              3495

Ser Gly Gly Ser Gly Ser Gly  Gly Ser Gly Ser Gly  Gly Ser Gly
    3500            3505              3510

Ser Gly Gly Ser Gly Ser Gly  Gly Ser Gly Ser Gly  Gly Ser Gly
    3515            3520              3525

Ser Gly Gly Ser Gly Ser Gly  Gly Ser Gly Ser Gly  Gly Ser Gly
    3530            3535              3540

Ser Gly Gly Ser Gly Ser Gly  Gly Ser Gly Ser Gly  Gly Ser Gly
    3545            3550              3555

Ser Gly Gly Ser Gly Ser Gly  Gly Ser Gly Ser Gly  Gly Ser Gly
    3560            3565              3570

Ser Gly Gly Ser Gly Ser Gly  Gly Ser Gly Ser Gly  Gly Ser Gly
    3575            3580              3585

Ser Gly Gly Ser Gly Ser Gly  Gly Ser Gly Ser Gly  Gly Ser Gly
    3590            3595              3600

Ser Gly Gly Ser Gly Ser Gly  Gly Ser Gly Ser Gly  Gly Ser Gly
    3605            3610              3615

Ser Gly Gly Ser Gly Ser Gly  Gly Ser Gly Ser Gly  Gly Ser Gly
    3620            3625              3630

Ser Gly Gly Ser Gly Ser Gly  Gly Ser Gly Ser Gly  Gly Ser Gly
    3635            3640              3645

Ser Gly Gly Ser Gly Ser Gly  Gly Ser Gly Ser Gly  Gly Ser Gly
    3650            3655              3660

Ser Gly Gly Ser Gly Ser Gly  Gly Ser Gly Ser Gly  Gly Ser Gly
    3665            3670              3675

Ser Gly Gly Ser Gly Ser Gly  Gly Ser Gly Ser Gly  Gly Ser Gly
    3680            3685              3690

Ser Gly Gly Ser Gly Ser Gly  Gly Ser Gly Ser Gly  Gly Ser Gly
    3695            3700              3705

Ser Gly Gly Ser Gly Ser Gly  Gly Ser Gly Ser Gly  Gly Ser Gly
    3710            3715              3720

Ser Gly Gly Ser Gly Ser Gly  Gly Ser Gly Ser Gly  Gly Ser Gly
    3725            3730              3735

Ser Gly Gly Ser Gly Ser Gly  Gly Ser Gly Ser Gly  Gly Ser Gly
    3740            3745              3750

Ser Gly Gly Ser Gly Ser Gly  Gly Ser Gly Ser Gly  Gly Ser Gly
    3755            3760              3765

Ser Gly Gly Ser Gly Ser Gly  Gly Ser Gly Ser Gly  Gly Ser Gly
    3770            3775              3780

Ser Gly Gly Ser Gly Ser Gly  Gly Ser Gly Ser Gly  Gly Ser Gly
    3785            3790              3795

Ser Gly Gly Ser Gly Ser Gly  Gly Ser Gly Ser Gly  Gly Ser Gly
    3800            3805              3810

Ser Gly Gly Ser Gly Ser Gly  Gly Ser Gly Ser Gly  Gly Ser Gly
    3815            3820              3825

Ser Gly Gly Ser Gly Ser Gly  Gly Ser Gly Ser Gly  Gly Ser Gly
    3830            3835              3840

Ser Gly Gly Ser Gly Ser Gly  Gly Ser Gly Ser Gly  Gly Ser Gly
    3845            3850              3855

Ser Gly Gly Ser Gly Ser Gly  Gly Ser Gly Ser Gly  Gly Ser Gly
    3860            3865              3870

Ser Gly Gly Ser Gly Ser Gly  Gly Ser Gly Ser Gly  Gly Ser Gly
```

-continued

```
                   3875                3880                3885
Ser Gly  Gly Ser Gly Ser Gly  Gly Ser Gly Ser Gly  Gly Ser Gly
    3890                3895                3900
Ser Gly  Gly Ser Gly Ser Gly  Gly Ser Gly Ser Gly  Gly Ser Gly
    3905                3910                3915
Ser Gly  Gly Ser Gly Ser Gly  Gly Ser Gly Ser Gly  Gly Ser Gly
    3920                3925                3930
Ser Gly  Gly Ser Gly Ser Gly  Gly Ser Gly Ser Gly  Gly Ser Gly
    3935                3940                3945
Ser Gly  Gly Ser Gly Ser Gly  Gly Ser Gly Ser Gly  Gly Ser Gly
    3950                3955                3960
Ser Gly  Gly Ser Gly Ser Gly  Gly Ser Gly Ser Gly  Gly Ser Gly
    3965                3970                3975
Ser Gly  Gly Ser Gly Ser Gly  Gly Ser Gly Ser Gly  Gly Ser Gly
    3980                3985                3990
Ser Gly  Gly Ser Gly Ser Gly
    3995                4000
```